(12) United States Patent
Cheever et al.

(10) Patent No.: US 7,247,703 B2
(45) Date of Patent: Jul. 24, 2007

(54) IMMUNE REACTIVITY TO HER-2/NEU PROTEIN FOR DIAGNOSIS AND TREATMENT OF MALIGNANCIES IN WHICH THE HER-2/NEU ONCOGENE IS ASSOCIATED

(75) Inventors: Martin A Cheever, Mercer Island, WA (US); Mary L Disis, Renton, WA (US)

(73) Assignee: University of Washington, Seattle, WA (US)

(*) Notice: Subject to any disclaimer, the term of this patent is extended or adjusted under 35 U.S.C. 154(b) by 534 days.

(21) Appl. No.: 10/647,005

(22) Filed: Aug. 21, 2003

(65) Prior Publication Data
US 2004/0082758 A1 Apr. 29, 2004

Related U.S. Application Data

(63) Continuation of application No. 09/354,533, filed on Jul. 15, 1999, now Pat. No. 6,664,370, which is a continuation of application No. 08/466,680, filed on Jun. 6, 1995, now Pat. No. 6,075,122, which is a continuation of application No. 08/414,417, filed on Mar. 31, 1995, now Pat. No. 5,801,005, which is a continuation-in-part of application No. 08/106,112, filed on Aug. 12, 1993, now abandoned, which is a continuation-in-part of application No. 08/033,644, filed on Mar. 17, 1993, now abandoned.

(51) Int. Cl.
C07K 7/08 (2006.01)
C07K 7/06 (2006.01)
A61K 38/08 (2006.01)
A61K 38/10 (2006.01)

(52) U.S. Cl. .............. 530/328; 530/326; 530/300; 530/350; 530/403; 530/402; 424/184.1; 424/185.1; 424/277.1; 514/2; 514/14; 514/15; 930/10

(58) Field of Classification Search .............. 530/328, 530/326, 300, 350, 403, 402; 424/184.1, 424/185.1, 277.1; 514/2, 14, 15; 930/10
See application file for complete search history.

(56) References Cited

U.S. PATENT DOCUMENTS

| | | | |
|---|---|---|---|
| 3,766,162 A | 10/1973 | Spector | 260/112 R |
| 3,791,932 A | 2/1974 | Schuurs et al. | 195/103.5 R |
| 3,817,837 A | 6/1974 | Rubenstein et al. | 195/103.5 R |
| 3,850,752 A | 11/1974 | Schuurs et al. | 195/103.5 R |
| 3,901,654 A | 8/1975 | Gross | 23/230 B |
| 3,935,074 A | 1/1976 | Rubenstein et al. | 195/103.5 R |
| 3,984,533 A | 10/1976 | Uzgiris | 424/12 |
| 3,996,345 A | 12/1976 | Ullman et al. | 424/12 |
| 4,034,074 A | 7/1977 | Miles | 424/1 |
| 4,098,876 A | 7/1978 | Piasio et al. | 424/1 |
| 4,233,402 A | 11/1980 | Maggio et al. | 435/7 |
| 4,452,901 A | 6/1984 | Gordon et al. | 436/506 |
| 5,320,947 A | 6/1994 | Cheever et al. | 435/29 |
| 5,401,638 A | 3/1995 | Carney et al. | 435/7.23 |
| 5,840,839 A * | 11/1998 | Wang et al. | 530/325 |
| 5,958,784 A | 9/1999 | Benner | 436/86 |
| 5,985,553 A | 11/1999 | King et al. | 435/6 |
| 6,514,942 B1 * | 2/2003 | Ioannides et al. | 514/15 |

FOREIGN PATENT DOCUMENTS

WO  WO 90/14357  11/1990
WO  WO 91/02062  2/1991

OTHER PUBLICATIONS

Disis, M.L. et al., "Immunity to the HER-2/Neu Oncogenic Protein", *Ciba Foundation Symposium*, Amsterdam, NL, 187:198-211, 1994.
Disis, M.L. et al., "Immunization to Oncogenic HER-2/neu Protein With Peptide Based Vaccines", *Proc. Amer. Assn. for Cancer Research* 36:251 (abstract 1498) Mar. 1995.
Alper et al., "The Presence of c-erbB-2 Gene Product-related Protein in Culture Medium Conditioned by Breast Cancer Cell Line SK-BR-3," *Cell Growth & Differentiation* 1:591-599, 1990.
Bargmann et al., "The neu oncogene encodes an epidermal growth factor receptor-related protein," *Nature* 319:226-230, 1986.
Baselga et al., "Phase II Study of Weekly Intravenous Recombinant Humanized Anti-p185(HER2) Monoclonal Antibody in Patients With HER2/neu-Overexpressing Metastatic Breast Cancer," *Journal of Clinical Oncology* 14(3): 737-744, 1996.
Ben-Mahrez et al., "Circulating Antibodies Against C-myc Oncogene Product In Sera Of Colorectal Cancer Patients," *Int. J. Cancer* 46: 35-38, 1990.
Bishop and Orosz, "Limiting Dilution Analysis For Alloreactive, TCGF-Secretory T Cells. Two Related LDA Methods That Discriminate Between Unstimulated Precursor T Cells and In Vivo-Alloactivated T Cells," *Transplantation* 47(4): 671-677, 1989.
Bodmer, W., "T-Cell Immune Responses to Cancer—A New Look," *Human Immunology* 30:259-261, 1991.
Bowen-Pope et al., "Production of platelet-derived growth factor-like molecules and reduced expression of platelet-derived growth factor receptors accompany transformation by a wide spectrum of agents," *Proc. Natl. Acad. Sci. USA* 81: 2396-2400, 1984.

(Continued)

*Primary Examiner*—Larry R. Helms
*Assistant Examiner*—Anne L. Holleran
(74) *Attorney, Agent, or Firm*—Seed IP Law Group PLLC

(57) ABSTRACT

Methods for the detection, monitoring and treatment of malignancies in which the HER-2/neu oncogene is associated are disclosed. Detection of specific T cell activation (e.g., by measuring the proliferation of T cells) in response to in vitro exposure to the HER-2/neu protein, or detection of immunocomplexes formed between the HER-2/neu protein and antibodies in body fluid, allows the diagnosis of the presence of a malignancy in which the HER-2/neu oncogene is associated. The present invention also discloses methods and compositions, including peptides, for treating such malignancies.

5 Claims, 20 Drawing Sheets

OTHER PUBLICATIONS

Brooks et al., "Human lymphocyte markers defined by antibodies derived from somatic cell hybrids," *Clin. Exp. Immunol. 39*: 477-485, 1980.

Brown et al., "Protein Antigens of Normal and Malignant Human Cells Identified by Immunoprecipitation with Monoclonal Antibodies," *Journal of Biological Chemistry 255*(11): 4980-4983, 1980.

Burnette et al., "Western Blotting: Electropheretic Transfer of Proteins from Sodium Dodecyl Sulfate-Polyacrylamide Gels to Unmodified Nitrocellulose and Radiographic Detection with Antibody Radioiodinated Protein A," *Analytical Biochemistry 112*: 195-203, 1981.

Coussens et al., "Tyrosine Kinase Receptor with Extensive Homology to EGF Receptor Shares Chromosomal Location with neu Oncogene," *Science 230:* 1132-1139, 1985.

Dhut et al, "BCR-ABL and BCR Proteins: Biochemical Characterization and Localization," *Leukemia 4*(11): 745-750, 1990.

Disis et al., "Existent T-Cell and Antibody Immunity to HER-2/neu Protein in Patients With Breast Cancer," *Cancer Res. 54*: 16-20, 1994.

Falk et al., "Allele-specific motifs revealed by sequencing of self-peptides eluted from MHC molecules," *Nature 351*: 290-296, 1991.

Feller and de la Cruz, "Identifying antigenic T-Cell sites," *Nature 349*: 720-721, 1991.

Fisk et al., "Oligopeptide Induction of a Cytotoxic T Lymphocyte Response to HER-2/Neu Proto-oncogene in Vitro," *Cellular Immunology 157*:415-427, 1994.

Flanagan and Leder, "neu protooncogene fused to an immunoglobulin heavy chain gene requires immunoglobulin light chain for cell surface expression and oncogenic transformation," *Proc. Natl. Acad. Sci. USA 85*: 8057-8061, 1998.

Igelhart et al., "Increased erbB-2 Gene Copies and Expression in Multiple Stages of Breast Cancer," *Cancer Research 50:* 6701-6707, 1990.

Ioannides et al., "Antigens Rocognized by T cells in Ovarian Cancer," in Abstracts of the Fourth International Conference of Anticancer Research, Oct. 21-25, 1992, Rethymnon, Crete, Greece, p. 1870.

Ioannides et al., "CTL Clones Isolated from Ovarian Tumor Infiltrating Lymphocytes can Recognize Peptides with Sequences Corresponding to the HER2/neu Gene Product," *FASEB Journal 6*: A1404, Abstract No. 2711, 1992.

Ioannides et al., "Cytotoxic T Cells Isolated From Ovarian Malignant Ascites Recognize a Peptide Derived From the HER-2/neu Proto-oncogene," *Cell. Immunol. 151*: 225-234, 1993.

Ionnides et al., "Cytotoxic T-Cell Clones Isolated from Ovarian Tumour Infiltrating Lymphocytes Recognize Common Determinants on Non-Ovarian Tumour Clones," *Scand. J. Immunol. 37*: 413-424, 1993.

Ioannides et al., "T-Cell Recognition of Oncogene Products: A New Strategy for Immunotherapy," *Molecular Carcinogenesis 6:* 77-82, 1992.

Ioannides, Abstracts Fourth International Conference of Anticancer Research Oct. 21-25, 1992, p. 1870.

Ioannides, "Antigens and vaccines of female genital cancers (Meeting abstract)," Cancerlit Database Abstract No. ICDB/93690682, 1992.

Ioannides, et al., "Cytotoxic T Cells Isolated From Ovarian Malignant Ascites Recognize a Peptide Derived From the HER-2/neu Proto-oncogene," *Cell Immunol. 151*:225-234, 1993.

Ioannides, Society for Biological Therapy 1992 Annual Meeting, p. 27 Oct. 29-Nov. 1, 1992.

Kallioniemi et al., "ERBB2 amplification in breast cancer analyzed by fluorescence in situ hybridization," *Proc. Natl. Acad. Sci. 89*: 5321-5325, 1992.

Kerns et al., "c-erbB-2 Expression In Breast Cancer Detected by Immunoblotting and Immunohistochemistry," *Journal of Histochemistry and Cytochemistry 38*(12): 1823-1830, 1990.

Laemmli, U., "Cleavage of Structural Proteins during the Assembly of the Head of Bacteriophage T4," *Nature 227*: 680-685, 1970.

Leitzel et al., "Elevated Soluble c-erbB2 Antigen Levels in the Serum and Effusions of a Proportion of Breast Cancer Patients," *Journal of Clinical Oncology 10*(9): 1436-1443, 1992.

Lichtenstein et al., "Effects of .beta.-2 Microglobulin Anti-sense oligonucleotides on Sensitivity of HER2/neu Oncogene-Expressing and Nonexpressin Target Cells to Lymphocyte-Mediated Lysis," *Cellular Immunology 141*: 219-232, 1992.

Lippman, M., "Potential Contributions of Breast Cancer Biology to Management of Breast Cancer," *Advances in Oncology 8*(3): 26-28, 1992.

Lippman, M., "Potential Contributions of Breast Cancer Biology to Management of Breast Cancer", *Advances in Oncology 8*(3): 26-28, 1992.

Maguire and Greene, "The neu (c-erbB-2) Oncogene," *Seminars in Oncology 16*(2): 148-155, 1989.

Margalit et al., "Prediction of Immunodominant Helper T Cell Antigenic Sites From The Primary Sequence," *Journal of Immunology 138*(7): 2213-2229, 1987.

McGlynn et al., "Large-scale purfication and characterisation of a recombinant epidermal growth-factor receptor protein-tyrosine kinase. Modulation of activity by multiple factors," *Eur. J. Biochem. 207*: 265-275, 1992.

McKenzie et al., "Induction of Antitumor Immunity by Immunization with a Vaccinia Virus Vector Expressing and Oncogene-encoded Product," in Vaccines 88, Cold Spring Harbor Laboratory, 1988, pp. 19-23.

Mietzner et al., "Purification and Characterization of the Major Iron-Regulated Protein Expressed By Pathogenic Neisseriae," *Journal of Experimental Medicine 165*: 1041-1057, 1987.

Mori et al., "In Vitro and in vivo Release of Soluble erbB-2 Protein from Human Carcinoma Cells," *Japanese Journal of Cancer Research 81*: 489-494, 1990.

Paik et al., "Pathologic Findings From the National Surgical Adjuvant Breast and Bowel Project: Prognostic Significance of erbB-2 Protein Overexpression in Primary Breast Cancer," *Journal of Clinical Oncology 8*(1): 103-112, 1990.

Parker et al., "Sequence Motifs Important For Peptide Binding To The Human MHC Class 1 Molecule, HLA-A2," *Journal of Immunology 149*(11): 3580-3587, 1992.

Press et al., "Expression of the HER-2/neu proto-oncogene in normal human adult and fetal tissues," *Oncogene 5*: 953-962, 1990.

Raines and Ross, "Platelet-derived Growth Factor. 1. High Yields Purification and Evidence for Multiple Forms," *Journal of Biological Chemistry 257*(9): 5154-5159, 1982.

Riberdy and Cresswell, "The Antigen-Processing Mutant T2 Suggests a Role for MHC-Linked Genes in Class II Antigen Presentation," *Journal of Immunology 148*(8):2586-2590, 1992.

Rothbard and Taylor, "A sequence pattern common to T cell epitopes," *EMBO Journal 7*(1): 93-100, 1988.

Semba et al., "A v-erbB-related protooncogene, c-erbB-2, is distinct from the c-erbB-1/epidermal growth factor-receptor gene and is amplified in human salivary gland adenocarcinoma," *Proc. Natl. Acad. Sci. USA 82*: 6497-6501, 1985.

Spies et al., "A gene in the human major histocompatibility complex class II region controlling the class I antigen presentation pathway," *Nature 348*: 744-747, 1990.

Stern et al., "Oncogene Activation of p185(*neu*) Stimulates Tyrosine Phosphorylation In Vivo," Molecular and Cellular Biology 8(9): 3969-3973, 1988.

Trowsdale et al., "Sequence encoded in the class II region of the MHC related to the 'ABC' superfamily of transporters," Nature 348: 741-744, 1990.

Weiner et al., "A point mutation in the neu oncogene mimics ligand induction of receptor aggregation," *Nature 339*: 230-231, 1989.

Wide, L., "Solid Phase Antigen-Antibody Systems," in Radioimmunoassay Methods, Kirkham and Hunter (eds.), 1973, pp. 405-412.

Wisdom, G.B., "Enzyme-Immunoassay," *Clin. Chem.* 22(8): 1243-1255, 1976.

Yamamoto et al., "Similarity of protein encoded by the c-erb-B-2 gene to epidermal growth factor receptor," *Nature 319*: 230-234, 1986.

Zabrecky et al., "The Extracellular Domain of p185/neu Is Released from the Surface of Human Breast Carcinoma Cells, SK-BR-3," *Journal of Biological Chemistry* 266(3): 1716-1720, 1991.

* cited by examiner

```
              5   10   15   20   25   30   35   40   45   50   55   60   65   70   75
MELAALCRWGLLLALLPPGAASTQVCTGTDMKLRLPASPETHLDMLRHLYQGCQVVQGNLELTYLPTNASLSFLQ 80   85   90   95  100  105  110  115  120  125  130  135  140  145  150
DIQEVQGYVLIAHNQVRQVPLQRLRIVRGTQLFEDNYALAVLDNGDPLNNTTPVTGASPGGLRELQLRSLTEILK 155  160  165  170  175  180  185  190  195  200  205  210  215  220  225
GGVLIQRNPQLCYQDTILWKDIFHKNNQLALTLIDTNRSRACHPCSPMCKGSRCWGESSEDCQSLTRTVCAGGCA 230  235  240  245  250  255  260  265  270  275  280  285  290  295  300
RCKGPLPTDCCHEQCAAGCTGPKHSDCLACLHFNHSGICELHCPALVTYNTDTFESMPNPEGRYTFGASCVTACP 305  310  315  320  325  330  335  340  345  350  355  360  365  370  375
YNYLSTDVGSCTLVCPLHNQEVTAEDGTQRCEKCSKPCARVCYGLGMEHLREVRAVTSANIQEFAGCKKIFGSLA 380  385  390  395  400  405  410  415  420  425  430  435  440  445  450
FLPESFDGDPASNTAPLQPEQLQVFETLEEITGYLYISAWPDSLPDLSVFQNLQVIRGRILHNGAYSLTLQGLGI 455  460  465  470  475  480  485  490  495  500  505  510  515  520  525
SWLGLRSLRELGSGLALIHHNTHLCFVHTVPWDQLFRNPHQALLHTANRPEDECVGEGLACHQLCARCHCWGPGP 530  535  540  545  550  555  560  565  570  575  580  585  590  595  600
TQCVNCSQFLRGQECVEECRVLQGLPREYVNARHCLPCHPECQPQNGSVTCFGPEADQCVACAHYKDPPFCVARC 605  610  615  620  625  630  635  640  645  650  655  660  665  670  675
PSGVKPDLSYMPIWKFPDEEGACQPCPINCTHSCVDLDDKGCPAEQRASPLTSIISAVVGILLVVVLGVVFGILI 680  685  690  695  700  705  710  715  720  725  730  735  740  745  750
KRRQQKIRKYTMRRLLQETELVEPLTPSGAMPNQAQMRILKETELRKVKVLGSGAFGTVYKGIWIPDGENVKIPV 755  760  765  770  775  780  785  790  795  800  805  810  815  820  825
AIKVLRENTSPKANKEILDEAYVMAGVGSPYVSRLLGICLTSTVQLVTQLMPYGCLLDHVRENRGRLGSQDLLNW 830  835  840  845  850  855  860  865  870  875  880  885  890  895  900
CMQIAKGMSYLEDVRLVHRDLAARNVLVKSPNHVKITDFGLARLLDIDETEYHADGGKVPIKWMALESILRRRFT 905  910  915  920  925  930  935  940  945  950  955  960  965  970  975
HQSDVWSYGVTVWELMTFGAKPYDGIPAREIPDLLEKGERLPQPPICTIDVYMIMVKCWMIDSECRPRFRELVSE 980  985  990  995 1000 1005 1010 1015 1020 1025 1030 1035 1040 1045 1050
FSRMARDPQRFVVIQNEDLGPASPLDSTFYRSLLEDDDMGDLVDAEEYLVPQQGFFCPDPAPGAGGMVHHRHRSS 1055 1060 1065 1070 1075 1080 1085 1090 1095 1100 1105 1110 1115 1120 1125
STRSGGGDLTLGLEPSEEEAPRSPLAPSEGAGSDVFDGDLGMGAAKGLQSLPTHDPSPLQRYSEDPTVPLPSETD 1130 1135 1140 1145 1150 1155 1160 1165 1170 1175 1180 1185 1190 1195 1200
GYVAPLTCSPQPEYVNQPDVRPQPPSPREGPLPAARPAGATLERPKTLSPGKNGVVKDVFAFGGAVENPEYLTPQ 1205 1210 1215 1220 1225 1230 1235 1240 1245 1250 1255
GGAAPQPHPPPAFSPAFDNLYYWDQDPPERGAPPSTFKGTPTAENPEYLGLDVPV
```

FIG. 1

SEQUENCE LISTING

```
(1) GENERAL INFORMATION:

(iii) NUMBER OF SEQUENCES: 69

(2) INFORMATION FOR SEQ ID NO: 1:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 1:

His Leu Tyr Gln Gly Cys Gln Val Val
1               5

(2) INFORMATION FOR SEQ ID NO: 2:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 2:

Pro Leu Gln Pro Glu Gln Leu Gln Val
1               5

(2) INFORMATION FOR SEQ ID NO: 3:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 3:

Pro Leu Thr Ser Ile Ile Ser Ala Val
1               5

(2) INFORMATION FOR SEQ ID NO: 4:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 4:

Ile Leu Leu Val Val Val Leu Gly Val
1               5

(2) INFORMATION FOR SEQ ID NO: 5:

(i) SEQUENCE CHARACTERISTICS:
        (A) LENGTH: 9 amino acids
        (B) TYPE: amino acid
        (D) TOPOLOGY: linear
```

```
        (xi) SEQUENCE DESCRIPTION: SEQ ID NO: 5:

Leu Leu Val Val Val Leu Gly Val Val
1               5

(2) INFORMATION FOR SEQ ID NO: 6:

(i) SEQUENCE CHARACTERISTICS:
            (A) LENGTH: 9 amino acids
            (B) TYPE: amino acid
            (D) TOPOLOGY: linear (xi) SEQUENCE DESCRIPTION: SEQ ID NO: 6:

Arg Leu Leu Gln Glu Thr Glu Leu Val
1               5

(2) INFORMATION FOR SEQ ID NO: 7:

(i) SEQUENCE CHARACTERISTICS:
            (A) LENGTH: 9 amino acids
            (B) TYPE: amino acid
            (D) TOPOLOGY: linear (xi) SEQUENCE DESCRIPTION: SEQ ID NO: 7:

Cys Leu Thr Ser Thr Val Gln Leu Val
1               5

(2) INFORMATION FOR SEQ ID NO: 8:

(i) SEQUENCE CHARACTERISTICS:
            (A) LENGTH: 9 amino acids
            (B) TYPE: amino acid
            (D) TOPOLOGY: linear (xi) SEQUENCE DESCRIPTION: SEQ ID NO: 8:

Asp Leu Ala Ala Arg Asn Val Leu Val
1               5

(2) INFORMATION FOR SEQ ID NO: 9:

(i) SEQUENCE CHARACTERISTICS:
            (A) LENGTH: 9 amino acids
            (B) TYPE: amino acid
            (D) TOPOLOGY: linear (xi) SEQUENCE DESCRIPTION: SEQ ID NO: 9:

Val Leu Val Lys Ser Pro Asn His Val
1               5

(2) INFORMATION FOR SEQ ID NO: 10:

(i) SEQUENCE CHARACTERISTICS:
            (A) LENGTH: 9 amino acids
            (B) TYPE: amino acid
            (D) TOPOLOGY: linear (xi) SEQUENCE DESCRIPTION: SEQ ID NO: 10:

Thr Leu Ser Pro Gly Lys Asn Gly Val
1               5

(2) INFORMATION FOR SEQ ID NO: 11:

(i) SEQUENCE CHARACTERISTICS:
            (A) LENGTH: 9 amino acids
            (B) TYPE: amino acid
            (D) TOPOLOGY: linear
```

(xi) SEQUENCE DESCRIPTION: SEQ ID NO: 11:

Val Leu Gly Val Val Phe Gly Ile Leu
1               5

(2) INFORMATION FOR SEQ ID NO: 12:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 12:

Leu Ile Lys Arg Arg Gln Gln Lys Ile
1               5

(2) INFORMATION FOR SEQ ID NO: 13:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 13:

Lys Ile Pro Val Ala Ile Lys Val Leu
1               5

(2) INFORMATION FOR SEQ ID NO: 14:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 14:

Ile Leu Asp Glu Ala Tyr Val Met Ala
1               5

(2) INFORMATION FOR SEQ ID NO: 15:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 15:

Gln Leu Met Pro Tyr Gly Cys Leu Leu
1               5

(2) INFORMATION FOR SEQ ID NO: 16:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 16:

Gln Ile Ala Lys Gly Met Ser Tyr Leu
1               5

(2) INFORMATION FOR SEQ ID NO: 17:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 17:

```
Leu Leu Asn Trp Cys Met Gln Ile Ala
1               5
```

(2) INFORMATION FOR SEQ ID NO: 18:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 18:

```
Arg Leu Val His Arg Asp Leu Ala Ala
1               5
```

(2) INFORMATION FOR SEQ ID NO: 19:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 19:

```
Asp Ile Asp Glu Thr Glu Tyr His Ala
1               5
```

(2) INFORMATION FOR SEQ ID NO: 20:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 20:

```
Asp Leu Leu Glu Lys Gly Glu Arg Leu
1               5
```

(2) INFORMATION FOR SEQ ID NO: 21:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 21:

```
Thr Ile Asp Val Tyr Met Leu Met Val
1               5
```

(2) INFORMATION FOR SEQ ID NO: 22:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 22:

```
Met Ile Met Val Lys Cys Trp Met Ile
1               5
```

(2) INFORMATION FOR SEQ ID NO: 23:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 23:

```
Asp Leu Val Asp Ala Glu Glu Tyr Leu
1               5
```

(2) INFORMATION FOR SEQ ID NO: 24:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 24:

```
Gly Leu Glu Pro Ser Glu Glu Glu Ala
1               5
```

(2) INFORMATION FOR SEQ ID NO: 25:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 25:

```
Tyr Leu Thr Pro Gln Gly Gly Ala Ala
1               5
```

(2) INFORMATION FOR SEQ ID NO: 26:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (xi) SEQUENCE DESCRIPTION: SEQ ID NO: 26:

```
Gln Leu Phe Glu Asp Asn Tyr Ala Leu
1               5
```

(2) INFORMATION FOR SEQ ID NO: 27:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (xi) SEQUENCE DESCRIPTION: SEQ ID NO: 27:

```
Lys Ile Phe Gly Ser Leu Ala Phe Leu
1               5
```

(2) INFORMATION FOR SEQ ID NO: 28:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (xi) SEQUENCE DESCRIPTION: SEQ ID NO: 28:

```
Ile Leu Asp Glu Ala Tyr Val Met Ala Gly Val
1               5                   10
```

(2) INFORMATION FOR SEQ ID NO: 29:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear

```
        (xi) SEQUENCE DESCRIPTION: SEQ ID NO: 29:

Val Met Ala Gly Val Gly Ser Pro Tyr Val
1               5                   10

(2) INFORMATION FOR SEQ ID NO: 30:

(i) SEQUENCE CHARACTERISTICS:
         (A) LENGTH: 15 amino acids
         (B) TYPE: amino acid
         (D) TOPOLOGY: linear (xi) SEQUENCE DESCRIPTION: SEQ ID NO: 30:

His Leu Asp Met Leu Arg His Leu Tyr Gln Gly Cys Gln Val Val
1               5                   10                  15

(2) INFORMATION FOR SEQ ID NO: 31:

(i) SEQUENCE CHARACTERISTICS:
         (A) LENGTH: 15 amino acids
         (B) TYPE: amino acid
         (D) TOPOLOGY: linear (xi) SEQUENCE DESCRIPTION: SEQ ID NO: 31:

Pro Leu Gln Arg Leu Arg Ile Val Arg Gly Thr Gln Leu Phe Glu
1               5                   10                  15

(2) INFORMATION FOR SEQ ID NO: 32:

(i) SEQUENCE CHARACTERISTICS:
         (A) LENGTH: 15 amino acids
         (B) TYPE: amino acid
         (D) TOPOLOGY: linear (xi) SEQUENCE DESCRIPTION: SEQ ID NO: 32:

Leu Arg Ser Leu Thr Glu Ile Leu Lys Gly Gly Val Leu Ile Gln
1               5                   10                  15

(2) INFORMATION FOR SEQ ID NO: 33:

(i) SEQUENCE CHARACTERISTICS:
         (A) LENGTH: 15 amino acids
         (B) TYPE: amino acid
         (D) TOPOLOGY: linear (xi) SEQUENCE DESCRIPTION: SEQ ID NO: 33:

Val Thr Tyr Asn Thr Asp Thr Phe Glu Ser Met Pro Asn Pro Glu
1               5                   10                  15

(2) INFORMATION FOR SEQ ID NO: 34:

(i) SEQUENCE CHARACTERISTICS:
         (A) LENGTH: 15 amino acids
         (B) TYPE: amino acid
         (D) TOPOLOGY: linear (xi) SEQUENCE DESCRIPTION: SEQ ID NO: 34:

His Leu Arg Glu Val Arg Ala Val Thr Ser Ala Asn Ile Gln Glu
1               5                   10                  15

(2) INFORMATION FOR SEQ ID NO: 35:

(i) SEQUENCE CHARACTERISTICS:
         (A) LENGTH: 15 amino acids
         (B) TYPE: amino acid
         (D) TOPOLOGY: linear
```

(xi) SEQUENCE DESCRIPTION: SEQ ID NO: 35:

Val Arg Ala Val Thr Ser Ala Asn Ile Gln Glu Phe Ala Gly Cys
1               5                   10                  15

(2) INFORMATION FOR SEQ ID NO: 36:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 36:

Asn Ile Gln Glu Phe Ala Gly Cys Lys Lys Ile Phe Gly Ser Leu
1               5                   10                  15

(2) INFORMATION FOR SEQ ID NO: 37:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 37:

Gln Val Phe Glu Thr Leu Glu Glu Ile Thr Gly Tyr Leu Tyr Ile
1               5                   10                  15

(2) INFORMATION FOR SEQ ID NO: 38:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 38:

Gln Glu Cys Val Glu Glu Cys Arg Val Leu Gln Gly Leu Pro Arg
1               5                   10                  15

(2) INFORMATION FOR SEQ ID NO: 39:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 39:

Val Val Val Leu Gly Val Val Phe Gly Ile Leu Ile Lys Arg Arg
1               5                   10                  15

(2) INFORMATION FOR SEQ ID NO: 40:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 40:

Lys Tyr Thr Met Arg Arg Leu Leu Gln Glu Thr Glu Leu Val Glu
1               5                   10                  15

(2) INFORMATION FOR SEQ ID NO: 41:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 41:

```
Gly Ala Met Pro Asn Gln Ala Gln Met Arg Ile Leu Lys Glu Thr
1               5                   10                  15
```

(2) INFORMATION FOR SEQ ID NO: 42:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 42:

```
Val Lys Val Leu Gly Ser Gly Ala Phe Gly Thr Val Tyr Lys Gly
1               5                   10                  15
```

(2) INFORMATION FOR SEQ ID NO: 43:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 43:

```
Ser Pro Lys Ala Asn Lys Glu Ile Leu Asp Glu Ala Tyr Val Met
1               5                   10                  15
```

(2) INFORMATION FOR SEQ ID NO: 44:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 44:

```
Gly Val Gly Ser Pro Tyr Val Ser Arg Leu Leu Gly Ile Cys Leu
1               5                   10                  15
```

(2) INFORMATION FOR SEQ ID NO: 45:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 45:

```
Ser Arg Leu Leu Gly Ile Cys Leu Thr Ser Thr Val Gln Leu Val
1               5                   10                  15
```

(2) INFORMATION FOR SEQ ID NO: 46:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 46:

```
Gly Ser Gln Asp Leu Leu Asn Trp Cys Met Gln Ile Ala Lys Gly
1               5                   10                  15
```

(2) INFORMATION FOR SEQ ID NO: 47:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 47:

```
Val Lys Ile Thr Asp Phe Gly Leu Ala Arg Leu Leu Asp Ile Asp
1               5                  10                 15
```

(2) INFORMATION FOR SEQ ID NO: 48:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 48:

```
Thr Val Trp Glu Leu Met Thr Phe Gly Ala Lys Pro Tyr Asp Gly
1               5                  10                 15
```

(2) INFORMATION FOR SEQ ID NO: 49:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 49:

```
Pro Ala Arg Glu Ile Pro Asp Leu Leu Glu Lys Gly Glu Arg Leu
1               5                  10                 15
```

(2) INFORMATION FOR SEQ ID NO: 50:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 50:

```
Arg Phe Arg Glu Leu Val Ser Glu Phe Ser Arg Met Ala Arg Asp
1               5                  10                 15
```

(2) INFORMATION FOR SEQ ID NO: 51:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 51:

```
Glu Asp Asp Asp Met Gly Asp Leu Val Asp Ala Glu Glu Tyr Leu
1               5                  10                 15
```

(2) INFORMATION FOR SEQ ID NO: 52:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 52:

```
Gly Met Gly Ala Ala Lys Gly Leu Gln Ser Leu Pro Thr His Asp
1               5                  10                 15
```

(2) INFORMATION FOR SEQ ID NO: 53:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 53:

```
Thr Cys Ser Pro Gln Pro Glu Tyr Val Asn Gln Pro Asp Val Arg
```

```
1               5                  10                 15
```

(2) INFORMATION FOR SEQ ID NO: 54:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 54:

```
Thr Leu Glu Arg Pro Lys Thr Leu Ser Pro Gly Lys Asn Gly Val
1               5                  10                 15
```

(2) INFORMATION FOR SEQ ID NO: 55:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 55:

```
Gly Gly Ala Val Glu Asn Pro Glu Tyr Leu Thr Pro Gln Gly Gly
1               5                  10                 15
```

(2) INFORMATION FOR SEQ ID NO: 56:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (xi) SEQUENCE DESCRIPTION: SEQ ID NO: 56:

```
Asn Gln Glu Val Thr Ala Glu Asp Gly Thr Gln Arg Cys Glu Lys
1               5                  10                 15
```

(2) INFORMATION FOR SEQ ID NO: 57:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (xi) SEQUENCE DESCRIPTION: SEQ ID NO: 57:

```
Gln Val Ile Arg Gly Arg Ile Leu His Asn Gly Ala Tyr Ser Leu
1               5                  10                 15
```

(2) INFORMATION FOR SEQ ID NO: 58:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (xi) SEQUENCE DESCRIPTION: SEQ ID NO: 58:

```
Leu Gln Val Phe Glu Thr Leu Glu Glu Ile Thr Gly Tyr Leu Tyr
1               5                  10                 15
```

(2) INFORMATION FOR SEQ ID NO: 59:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (xi) SEQUENCE DESCRIPTION: SEQ ID NO: 59:

Ala Ser Pro Leu Thr Ser Ile Ile Ser Ala Val Val Gly Ile Leu
1               5                  10                  15

(2) INFORMATION FOR SEQ ID NO: 60:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (xi) SEQUENCE DESCRIPTION: SEQ ID NO: 60:

Thr Gln Arg Cys Glu Lys Cys Ser Lys Pro Cys Ala Arg Val Cys Ty
1               5                  10                  15

Gly Leu (2) INFORMATION FOR SEQ ID NO: 61:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (xi) SEQUENCE DESCRIPTION: SEQ ID NO: 61:

Arg Leu Arg Ile Val Arg Gly Thr Gln Leu Phe Glu Asp Asn Tyr Al
1               5                  10                  15

Leu (2) INFORMATION FOR SEQ ID NO: 62:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (xi) SEQUENCE DESCRIPTION: SEQ ID NO: 62:

Lys Ile Phe Gly Ser Leu Ala Phe Leu Pro Glu Ser Phe Asp Gly As
1               5                  10                  15

(2) INFORMATION FOR SEQ ID NO: 63:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (xi) SEQUENCE DESCRIPTION: SEQ ID NO: 63:

Arg Arg Leu Leu Gln Glu Thr Glu Leu Val Glu Pro Leu Thr Pro Se
1               5                  10                  15

(2) INFORMATION FOR SEQ ID NO: 64:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (xi) SEQUENCE DESCRIPTION: SEQ ID NO: 64:

Glu Leu Val Ser Glu Phe Ser Arg Met Ala Arg Asp Pro Gln
1               5                  10

(2) INFORMATION FOR SEQ ID NO: 65:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO: 65:

Thr Ala Glu Asn Pro Glu Tyr Leu Gly Leu Asp Val Pro Val
1               5                   10

(2) INFORMATION FOR SEQ ID NO: 66:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO: 66:

Leu Ala Arg Leu Leu Asp Ile Asp Glu Thr Glu Tyr Ala Asp
1               5                   10

(2) INFORMATION FOR SEQ ID NO: 67:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (xi) SEQUENCE DESCRIPTION: SEQ ID NO: 67:

Arg Ile Ile Arg Gly Arg Ile Leu His Asp Gly Ala Tyr Ser Leu
1               5                   10                  15

(2) INFORMATION FOR SEQ ID NO: 68:

(i) SEQUENCE CHARACTERISTICS:
        (A) LENGTH: 1255 amino acids
        (B) TYPE: amino acid
        (D) TOPOLOGY: linear (xi) SEQUENCE DESCRIPTION: SEQ ID NO: 68:

Met Glu Leu Ala Ala Leu Cys Arg Trp Gly Leu Leu Leu Ala Leu Le
1               5                   10                  15

Pro Pro Gly Ala Ala Ser Thr Gln Val Cys Thr Gly Thr Asp Met Ly
                20                  25                  30

Leu Arg Leu Pro Ala Ser Pro Glu Thr His Leu Asp Met Leu Arg Hi
            35                  40                  45

Leu Tyr Gln Gly Cys Gln Val Val Gln Gly Asn Leu Glu Leu Thr Ty
        50                  55                  60

Leu Pro Thr Asn Ala Ser Leu Ser Phe Leu Gln Asp Ile Gln Glu Va
65                  70                  75                  80

Gln Gly Tyr Val Leu Ile Ala His Asn Gln Val Arg Gln Val Pro Le
                85                  90                  95

Gln Arg Leu Arg Ile Val Arg Gly Thr Gln Leu Phe Glu Asp Asn Ty
            100                 105                 110

Ala Leu Ala Val Leu Asp Asn Gly Asp Pro Leu Asn Asn Thr Thr Pr
        115                 120                 125

Val Thr Gly Ala Ser Pro Gly Gly Leu Arg Glu Leu Gln Leu Arg Se
    130                 135                 140

Leu Thr Glu Ile Leu Lys Gly Gly Val Leu Ile Gln Arg Asn Pro Gl
145                 150                 155                 160

-continued

```
Leu Cys Tyr Gln Asp Thr Ile Leu Trp Lys Asp Ile Phe His Lys As
                165                 170                 175
Asn Gln Leu Ala Leu Thr Leu Ile Asp Thr Asn Arg Ser Arg Ala Cy
            180                 185                 190
His Pro Cys Ser Pro Met Cys Lys Gly Ser Arg Cys Trp Gly Glu Se
        195                 200                 205
Ser Glu Asp Cys Gln Ser Leu Thr Arg Thr Val Cys Ala Gly Gly Cy
    210                 215                 220
Ala Arg Cys Lys Gly Pro Leu Pro Thr Asp Cys Cys His Glu Gln Cy
225                 230                 235                 240
Ala Ala Gly Cys Thr Gly Pro Lys His Ser Asp Cys Leu Ala Cys Le
            245                 250                 255
His Phe Asn His Ser Gly Ile Cys Glu Leu His Cys Pro Ala Leu Va
        260                 265                 270
Thr Tyr Asn Thr Asp Thr Phe Glu Ser Met Pro Asn Pro Glu Gly Ar
    275                 280                 285
Tyr Thr Phe Gly Ala Ser Cys Val Thr Ala Cys Pro Tyr Asn Tyr Le
    290                 295                 300
Ser Thr Asp Val Gly Ser Cys Thr Leu Val Cys Pro Leu His Asn Gl
305                 310                 315                 320
Glu Val Thr Ala Glu Asp Gly Thr Gln Arg Cys Glu Lys Cys Ser Ly
            325                 330                 335
Pro Cys Ala Arg Val Cys Tyr Gly Leu Gly Met Glu His Leu Arg Gl
        340                 345                 350
Val Arg Ala Val Thr Ser Ala Asn Ile Gln Glu Phe Ala Gly Cys Ly
    355                 360                 365
Lys Ile Phe Gly Ser Leu Ala Phe Leu Pro Glu Ser Phe Asp Gly As
    370                 375                 380
Pro Ala Ser Asn Thr Ala Pro Leu Gln Pro Glu Gln Leu Gln Val Ph
385                 390                 395                 400
Glu Thr Leu Glu Glu Ile Thr Gly Tyr Leu Tyr Ile Ser Ala Trp Pr
            405                 410                 415
Asp Ser Leu Pro Asp Leu Ser Val Phe Gln Asn Leu Gln Val Ile Ar
        420                 425                 430
Gly Arg Ile Leu His Asn Gly Ala Tyr Ser Leu Thr Leu Gln Gly Le
    435                 440                 445
Gly Ile Ser Trp Leu Gly Leu Arg Ser Leu Arg Glu Leu Gly Ser Gl
    450                 455                 460
Leu Ala Leu Ile His His Asn Thr His Leu Cys Phe Val His Thr Va
465                 470                 475                 480
Pro Trp Asp Gln Leu Phe Arg Asn Pro His Gln Ala Leu Leu His Th
            485                 490                 495
Ala Asn Arg Pro Glu Asp Glu Cys Val Gly Glu Gly Leu Ala Cys Hi
        500                 505                 510
Gln Leu Cys Ala Arg Cys His Cys Trp Gly Pro Gly Pro Thr Gln Cy
    515                 520                 525
Val Asn Cys Ser Gln Phe Leu Arg Gly Gln Glu Cys Val Glu Glu Cy
    530                 535                 540
Arg Val Leu Gln Gly Leu Pro Arg Glu Tyr Val Asn Ala Arg His Cy
545                 550                 555                 560
Leu Pro Cys His Pro Glu Cys Gln Pro Gln Asn Gly Ser Val Thr Cy
            565                 570                 575
```

-continued

Phe Gly Pro Glu Ala Asp Gln Cys Val Ala Cys Ala His Tyr Lys As
           580                 585                 590

Pro Pro Phe Cys Val Ala Arg Cys Pro Ser Gly Val Lys Pro Asp Le
           595                 600                 605

Ser Tyr Met Pro Ile Trp Lys Phe Pro Asp Glu Gly Ala Cys Gl
           610                 615                 620

Pro Cys Pro Ile Asn Cys Thr His Ser Cys Val Asp Leu Asp Asp Ly
625                 630                 635                 640

Gly Cys Pro Ala Glu Gln Arg Ala Ser Pro Leu Thr Ser Ile Ile Se
                645                 650                 655

Ala Val Val Gly Ile Leu Leu Val Val Leu Gly Val Val Phe Gl
            660                 665                 670

Ile Leu Ile Lys Arg Arg Gln Gln Lys Ile Arg Lys Tyr Thr Met Ar
            675                 680                 685

Arg Leu Leu Gln Glu Thr Glu Leu Val Glu Pro Leu Thr Pro Ser Gl
            690                 695                 700

Ala Met Pro Asn Gln Ala Gln Met Arg Ile Leu Lys Glu Thr Glu Le
705                 710                 715                 720

Arg Lys Val Lys Val Leu Gly Ser Gly Ala Phe Gly Thr Val Tyr Ly
                725                 730                 735

Gly Ile Trp Ile Pro Asp Gly Glu Asn Val Lys Ile Pro Val Ala Il
            740                 745                 750

Lys Val Leu Arg Glu Asn Thr Ser Pro Lys Ala Asn Lys Glu Ile Le
            755                 760                 765

Asp Glu Ala Tyr Val Met Ala Gly Val Gly Ser Pro Tyr Val Ser Ar
            770                 775                 780

Leu Leu Gly Ile Cys Leu Thr Ser Thr Val Gln Leu Val Thr Gln Le
785                 790                 795                 800

Met Pro Tyr Gly Cys Leu Leu Asp His Val Arg Glu Asn Arg Gly Ar
            805                 810                 815

Leu Gly Ser Gln Asp Leu Leu Asn Trp Cys Met Gln Ile Ala Lys Gl
            820                 825                 830

Met Ser Tyr Leu Glu Asp Val Arg Leu Val His Arg Asp Leu Ala Al
            835                 840                 845

Arg Asn Val Leu Val Lys Ser Pro Asn His Val Lys Ile Thr Asp Ph
850                 855                 860

Gly Leu Ala Arg Leu Leu Asp Ile Asp Glu Thr Glu Tyr His Ala As
865                 870                 875                 880

Gly Gly Lys Val Pro Ile Lys Trp Met Ala Leu Glu Ser Ile Leu Ar
                885                 890                 895

Arg Arg Phe Thr His Gln Ser Asp Val Trp Ser Tyr Gly Val Thr Va
            900                 905                 910

Trp Glu Leu Met Thr Phe Gly Ala Lys Pro Tyr Asp Gly Ile Pro Al
            915                 920                 925

Arg Glu Ile Pro Asp Leu Leu Glu Lys Gly Glu Arg Leu Pro Gln Pr
            930                 935                 940

Pro Ile Cys Thr Ile Asp Val Tyr Met Ile Met Val Lys Cys Trp Me
945                 950                 955                 960

Ile Asp Ser Glu Cys Arg Pro Arg Phe Arg Glu Leu Val Ser Glu Ph
                965                 970                 975

Ser Arg Met Ala Arg Asp Pro Gln Arg Phe Val Val Ile Gln Asn Gl
            980                 985                 990

Asp Leu Gly Pro Ala Ser Pro Leu Asp Ser Thr Phe Tyr Arg Ser Le

```
                995                 1000                1005
Leu Glu Asp Asp Met Gly Asp Leu Val Asp Ala Glu Glu Tyr Le
    1010                1015                1020

Val Pro Gln Gln Gly Phe Phe Cys Pro Asp Pro Ala Pro Gly Ala Gl
1025                1030                1035                1040

Gly Met Val His His Arg His Arg Ser Ser Thr Arg Ser Gly Gl
                1045                1050                1055

Gly Asp Leu Thr Leu Gly Leu Glu Pro Ser Glu Glu Ala Pro Ar
            1060                1065                1070

Ser Pro Leu Ala Pro Ser Glu Gly Ala Gly Ser Asp Val Phe Asp Gl
    1075                1080                1085

Asp Leu Gly Met Gly Ala Ala Lys Gly Leu Gln Ser Leu Pro Thr Hi
    1090                1095                1100

Asp Pro Ser Pro Leu Gln Arg Tyr Ser Glu Asp Pro Thr Val Pro Le
1105                1110                1115                1120

Pro Ser Glu Thr Asp Gly Tyr Val Ala Pro Leu Thr Cys Ser Pro Gl
                1125                1130                1135

Pro Glu Tyr Val Asn Gln Pro Asp Val Arg Pro Gln Pro Pro Ser Pr
            1140                1145                1150

Arg Glu Gly Pro Leu Pro Ala Ala Arg Pro Ala Gly Ala Thr Leu Gl
        1155                1160                1165

Arg Pro Lys Thr Leu Ser Pro Gly Lys Asn Gly Val Val Lys Asp Va
    1170                1175                1180

Phe Ala Phe Gly Gly Ala Val Glu Asn Pro Glu Tyr Leu Thr Pro Gl
1185                1190                1195                1200

Gly Gly Ala Ala Pro Gln Pro His Pro Pro Ala Phe Ser Pro Al
                1205                1210                1215

Phe Asp Asn Leu Tyr Tyr Trp Asp Gln Asp Pro Pro Glu Arg Gly Al
            1220                1225                1230

Pro Pro Ser Thr Phe Lys Gly Thr Pro Thr Ala Glu Asn Pro Glu Ty
        1235                1240                1245

Leu Gly Leu Asp Val Pro Val
    1250                1255

(2) INFORMATION FOR SEQ ID NO: 69:

(i) SEQUENCE CHARACTERISTICS:
        (A) LENGTH: 580 amino acids
        (B) TYPE: amino acid
        (C) STRANDEDNESS: <Unknown>
        (D) TOPOLOGY: linear (xi) SEQUENCE DESCRIPTION: SEQ ID NO: 69:

Lys Arg Arg Gln Gln Lys Ile Arg Lys Tyr Thr Met Arg Arg Leu Le
1               5                   10                  15

Gln Glu Thr Glu Leu Val Glu Pro Leu Thr Pro Ser Gly Ala Met Pr
            20                  25                  30

Asn Gln Ala Gln Met Arg Ile Leu Lys Glu Thr Glu Leu Arg Lys Va
        35                  40                  45

Lys Val Leu Gly Ser Gly Ala Phe Gly Thr Val Tyr Lys Gly Ile Tr
    50                  55                  60

Ile Pro Asp Gly Glu Asn Val Lys Ile Pro Val Ala Ile Lys Val Le
65                  70                  75                  80

Arg Glu Asn Thr Ser Pro Lys Ala Asn Lys Glu Ile Leu Asp Glu Al
            85                  90                  95
```

```
Tyr Val Met Ala Gly Val Gly Ser Pro Tyr Val Ser Arg Leu Leu Gl
                100                 105                 110

Ile Cys Leu Thr Ser Thr Val Gln Leu Val Thr Gln Leu Met Pro Ty
            115                 120                 125

Gly Cys Leu Leu Asp His Val Arg Glu Asn Arg Gly Arg Leu Gly Se
            130                 135                 140

Gln Asp Leu Leu Asn Trp Cys Met Gln Ile Ala Lys Gly Met Ser Ty
145                 150                 155                 160

Leu Glu Asp Val Arg Leu Val His Arg Asp Leu Ala Ala Arg Asn Va
                165                 170                 175

Leu Val Lys Ser Pro Asn His Val Lys Ile Thr Asp Phe Gly Leu Al
            180                 185                 190

Arg Leu Leu Asp Ile Asp Glu Thr Glu Tyr His Ala Asp Gly Gly Ly
            195                 200                 205

Val Pro Ile Lys Trp Met Ala Leu Glu Ser Ile Leu Arg Arg Arg Ph
            210                 215                 220

Thr His Gln Ser Asp Val Trp Ser Tyr Gly Val Thr Val Trp Glu Le
225                 230                 235                 240

Met Thr Phe Gly Ala Lys Pro Tyr Asp Gly Ile Pro Ala Arg Glu Il
            245                 250                 255

Pro Asp Leu Leu Glu Lys Gly Glu Arg Leu Pro Gln Pro Pro Ile Cy
            260                 265                 270

Thr Ile Asp Val Tyr Met Ile Met Val Lys Cys Trp Met Ile Asp Se
            275                 280                 285

Glu Cys Arg Pro Arg Phe Arg Glu Leu Val Ser Glu Phe Ser Arg Me
            290                 295                 300

Ala Arg Asp Pro Gln Arg Phe Val Val Ile Gln Asn Glu Asp Leu Gl
305                 310                 315                 320

Pro Ala Ser Pro Leu Asp Ser Thr Phe Tyr Arg Ser Leu Leu Glu As
            325                 330                 335

Asp Asp Met Gly Asp Leu Val Asp Ala Glu Glu Tyr Leu Val Pro Gl
            340                 345                 350

Gln Gly Phe Phe Cys Pro Asp Pro Ala Pro Gly Ala Gly Gly Met Va
            355                 360                 365

His His Arg His Arg Ser Ser Ser Thr Arg Ser Gly Gly Gly Asp Le
            370                 375                 380

Thr Leu Gly Leu Glu Pro Ser Glu Glu Glu Ala Pro Arg Ser Pro Le
385                 390                 395                 400

Ala Pro Ser Glu Gly Ala Gly Ser Asp Val Phe Asp Gly Asp Leu Gl
            405                 410                 415

Met Gly Ala Ala Lys Gly Leu Gln Ser Leu Pro Thr His Asp Pro Se
            420                 425                 430

Pro Leu Gln Arg Tyr Ser Glu Asp Pro Thr Val Pro Leu Pro Ser Gl
            435                 440                 445

Thr Asp Gly Tyr Val Ala Pro Leu Thr Cys Ser Pro Gln Pro Glu Ty
            450                 455                 460

Val Asn Gln Pro Asp Val Arg Pro Gln Pro Pro Ser Pro Arg Glu Gl
465                 470                 475                 480

Pro Leu Pro Ala Ala Arg Pro Ala Gly Ala Thr Leu Glu Arg Pro Ly
            485                 490                 495

Thr Leu Ser Pro Gly Lys Asn Gly Val Val Lys Asp Val Phe Ala Ph
            500                 505                 510

Gly Gly Ala Val Glu Asn Pro Glu Tyr Leu Thr Pro Gln Gly Gly Al
```

```
                  515                 520                    525
Ala Pro Gln Pro His Pro Pro Pro Ala Phe Ser Pro Ala Phe Asp As
        530                     535                 540

Leu Tyr Tyr Trp Asp Gln Asp Pro Pro Glu Arg Gly Ala Pro Pro Se
545                 550                     555                 560

Thr Phe Lys Gly Thr Pro Thr Ala Glu Asn Pro Glu Tyr Leu Gly Le
                565                     570                 575

Asp Val Pro Val
            580
```

IMMUNE REACTIVITY TO HER-2/NEU PROTEIN FOR DIAGNOSIS AND TREATMENT OF MALIGNANCIES IN WHICH THE HER-2/NEU ONCOGENE IS ASSOCIATED

CROSS REFERENCES TO RELATED APPLICATIONS

This application is a continuation of U.S. patent application Ser. No. 09/354,533, filed Jul. 15, 1999 now U.S. Pat. No. 6,664,370 and allowed; which application is a continuation of U.S. patent application Ser. No. 08/466,680, filed Jun. 6, 1995, which issued as U.S. Pat. No. 6,075,122; which application is a continuation of U.S. patent application Ser. No. 08/414,417, filed Mar. 31, 1995 which issued as U.S. Pat. No. 5,801,005; which application is a continuation-in-part of U.S. patent application Ser. No. 08/106,112, filed Aug. 12, 1993 and abandoned; which application is a continuation-in-part of U.S. patent application Ser. No. 08/033,644, filed Mar. 17, 1993 and abandoned; which applications are incorporated by reference herein in their entirety.

BACKGROUND OF THE INVENTION

1. Field of the Invention

The present invention is generally directed toward the detection, monitoring, and treatment of malignancies, in which the HER-2/neu oncogene is associated, through the use of a cancer patient's own immune reactivity to the HER-2/neu protein expressed by the HER-2/neu gene.

2. Description of the Related Art

Despite enormous investments of financial and human resources, cancer remains one of the major causes of death. For example, cancer is the leading cause of death in women between the ages of 35 and 74. Breast cancer is the most common malignancy in women and the incidence for developing breast cancer is on the rise. One in nine women will be diagnosed with the disease. Standard approaches to cure breast cancer have centered around a combination of surgery, radiation and chemotherapy. These approaches have resulted in some dramatic successes in certain malignancies. However, breast cancer is most often incurable, when diagnosed beyond a certain stage. Alternative approaches to early diagnosis and therapy are necessary.

A common characteristic of malignancies is uncontrolled cell growth. Cancer cells appear to have undergone a process of transformation from the normal phenotype to a malignant phenotype capable of autonomous growth. Amplification and overexpression of somatic cell genes is considered to be a common primary event that results in the transformation of normal cells to malignant cells. The malignant phenotypic characteristics encoded by the oncogenic genes are passed on during cell division to the progeny of the transformed cells.

Ongoing research involving oncogenes has identified at least forty oncogenes operative in malignant cells and responsible for, or associated with, transformation. Oncogenes have been classified into different groups based on the putative function or location of their gene products (such as the protein expressed by the oncogene).

Oncogenes are believed to be essential for certain aspects of normal cellular physiology. In this regard, the HER-2/neu oncogene is a member of the tyrosine protein kinase family of oncogenes and shares a high degree of homology with the epidermal growth factor receptor. HER-2/neu presumably plays a role in cell growth and/or differentiation. HER-2/neu appears to induce malignancies through quantitative mechanisms that result from increased or deregulated expression of an essentially normal gene product.

HER-2/neu (p185) is the protein product of the HER-2/neu oncogene. The HER-2/neu gene is amplified and the HER-2/neu protein is overexpressed in a variety of cancers including breast, ovarian, colon, lung and prostate cancer. HER-2/neu is related to malignant transformation. It is found in 50%-60% of ductal in situ carcinoma and 20%-40% of all breast cancers, as well as a substantial fraction of adenocarcinomas arising in the ovaries, prostate, colon and lung. HER-2/neu is intimately associated not only with the malignant phenotype, but also with the aggressiveness of the malignancy, being found in one-fourth of all invasive breast cancers. HER-2/neu overexpression is correlated with a poor prognosis in both breast and ovarian cancer. HER-2/neu is a transmembrane protein with a relative molecular mass of 185 kd that is approximately 1255 amino acids (aa) in length. It has an extracellular binding domain (ECD) of approximately 645 aa, with 40% homology to epidermal growth factor receptor (EGFR), a highly hydrophobic transmembrane anchor domain (TMD), and a carboxyterminal cytoplasmic domain (CD) of approximately 580 aa with 80% homology to EGFR.

An approach to developing a diagnostic assay for malignancies, in which the HER-2/neu oncogene is associated, has been to attempt to quantify the protein expression product of the HER-2/neu oncogene in tissue or body fluids. However, there have been problems in the development of diagnostic assays based on direct detection of HER-2/neu protein.

Due to the difficulties in the current approaches to diagnosis and therapy of cancers in which the HER-2/neu oncogene is associated, there is a need in the art for improved methods and compositions. The present invention fills this need, and further provides other related advantages.

SUMMARY OF THE INVENTION

Briefly stated, the present invention provides a variety of methods for the detection of a malignancy in a warm-blooded animal, wherein a HER-2/neu oncogene is associated with the malignancy. The methods may be used on a one time basis when a malignancy is suspected or on a periodic basis, e.g., to monitor an individual with an elevated risk of acquiring or reacquiring a malignancy. In one embodiment, the method comprises the steps of: (a) isolating $CD4^+T$ cells from a warm-blooded animal; (b) incubating the T cells with HER-2/neu protein; and (c) detecting the presence or absence of specific activation of the T cells, thereby determining the presence or absence of the malignancy. In another embodiment, the method comprises the steps of: (a) isolating $CD8^+T$ cells from a warm-blooded animal; (b) incubating the T cells with HER-2/neu protein; and (c) detecting the presence or absence of specific activation of the T cells, thereby determining the presence or absence of the malignancy. In another embodiment, the method comprises the steps of: (a) contacting a body fluid, suspected of containing antibodies specific for HER-2/neu protein, with HER-2/neu protein; (b) incubating the body fluid under conditions and for a time sufficient to allow immunocomplexes to form; and (c) detecting the presence or absence of immunocomplexes formed between the HER-2/neu protein and antibodies in the body fluid specific for the HER-2/neu protein, thereby determining the presence or absence of the malignancy.

In another aspect, the present invention provides methods for monitoring the effectiveness of cancer therapy in a warm-blooded animal with a malignancy, wherein a HER-2/neu oncogene is associated with the malignancy. Uses of such methods include the early detection of relapse. In one embodiment, the method comprises the steps of: (a) contacting a first body fluid sample, taken from the warm-blooded animal prior to initiation of therapy, with HER-2/neu protein; (b) incubating the body fluid under conditions and for a time sufficient to allow immunocomplexes to form; (c) detecting immunocomplexes formed between the HER-2/neu protein and antibodies in the body fluid specific for the HER-2/neu protein; (d) repeating steps (a), (b), and (c) on a second body fluid sample taken from the animal subsequent to the initiation of therapy; and (e) comparing the number of immunocomplexes detected in the first and second body fluid samples, thereby monitoring the effectiveness of the therapy in the animal.

The present invention is also directed toward methods for treating a malignancy in a warm-blooded animal, wherein a HER-2/neu oncogene is associated with the malignancy. In one embodiment, the method comprises the steps of: (a) isolating CD4$^+$T cells from a warm-blooded animal; (b) incubating the T cells in the presence of HER-2/neu protein, such that the T cells proliferate; and (c) administering to the warm-blooded animal an effective amount of the proliferated T cells. In another embodiment, the method comprises the steps of: (a) isolating CD8$^+$T cells from a warm-blooded animal; (b) incubating the T cells in the presence of HER-2/neu protein, such that the T cells proliferate; and (c) administering to the warm-blooded animal an effective amount of the proliferated T cells. In another embodiment, the method comprises the steps of: (a) isolating CD4$^+$T cells from a warm-blooded animal; (b) incubating the T cells in the presence of HER-2/neu protein, such that the T cells proliferate; (c) cloning one or more cells that proliferated in the presence of HER-2/neu protein; and (d) administering to the warm-blooded animal an effective amount of the cloned T cells. In another embodiment, the method comprises the steps of: (a) isolating CD8$^+$T cells from a warm-blooded animal; (b) incubating the T cells in the presence of HER-2/neu protein, such that the T cells proliferate; (c) cloning one or more cells that proliferated in the presence of HER-2/neu protein; and (d) administering to the warm-blooded animal an effective amount of the cloned T cells. In yet another embodiment, the method comprises immunizing the animal with a HER-2/neu peptide recognized by T cells, the peptide not being the extracellular domain of the protein expression product of a HER-2/neu oncogene.

Within a related aspect, the present invention provides anti-cancer therapeutic compositions comprising T cells proliferated in the presence of HER-2/neu protein, in combination with a pharmaceutically acceptable carrier or diluent. In addition, a variety of peptides designated for CD8$^+$T cell responses are provided which include peptides consisting essentially of:

(Seq. ID No. 1)
His-Leu-Tyr-Gln-Gly-Cys-Gln-Val-Val;

(Seq. ID No. 2)
Pro-Leu-Gln-Pro-Glu-Gln-Leu-Gln-Val;

(Seq. ID No. 3)
Pro-Leu-Thr-Ser-Ile-Ile-Ser-Ala-Val;

-continued (Seq. ID No. 4)
Ile-Leu-Leu-Val-Val-Val-Leu-Gly-Val;

(Seq. ID No. 5)
Leu-Leu-Val-Val-Val-Leu-Gly-Val-Val;

(Seq. ID No. 6)
Arg-Leu-Leu-Gln-Glu-Thr-Glu-Leu-Val;

(Seq. ID No. 7)
Cys-Leu-Thr-Ser-Thr-Val-Gln-Leu-Val;

(Seq. ID No. 8)
Asp-Leu-Ala-Ala-Arg-Asn-Val-Leu-Val;

(Seq. ID No. 9)
Val-Leu-Val-Lys-Ser-Pro-Asn-His-Val;

(Seq. ID No. 10)
Thr-Leu-Ser-Pro-Gly-Lys-Asn-Gly-Val;

(Seq. ID No. 11)
Val-Leu-Gly-Val-Val-Phe-Gly-Ile-Leu;

(Seq. ID No. 12)
Leu-Ile-Lys-Arg-Arg-Gln-Gln-Lys-Ile;

(Seq. ID No. 13)
Lys-Ile-Pro-Val-Ala-Ile-Lys-Val-Leu;

(Seq. ID No. 14)
lIe-Leu-Asp-Glu-Ala-Tyr-Val-Met-Ala;

(Seq. ID No. 15)
Gln-Leu-Met-Pro-Tyr-Gly-Cys-Leu-Leu;

(Seq. ID No. 16)
Gln-Ile-Ala-Lys-Gly-Met-Ser-Tyr-Leu;

(Seq. ID No. 17)
Leu-Leu-Asn-Trp-Cys-Met-Gln-Ile-Ala;

(Seq. ID No. 18)
Arg-Leu-Val-His-Arg-Asp-Leu-Ala-Ala;

(Seq. ID No. 19)
Asp-Ile-Asp-Glu-Thr-Glu-Tyr-His-Ala;

(Seq. ID No. 20)
Asp-Leu-Leu-Glu-Lys-Gly-Glu-Arg-Leu;

(Seq. ID No. 21)
Thr-Ile-Asp-Val-Tyr-Met-Leu-Met-Val;

(Seq. ID No. 22)
Met-Ile-Met-Val-Lys-Cys-Trp-Met-Ile;

(Seq. ID No. 23)
Asp-Leu-Val-Asp-Ala-Glu-Glu-Tyr-Leu;

(Seq. ID No. 24)
Gly-Leu-Glu-Pro-Ser-Glu-Glu-Glu-Ala;

or (Seq. ID No. 25)
Tyr-Leu-Thr-Pro-Gln-Gly-Gly-Ala-Ala.

Similarly, a variety of peptides designated for CD4+T cell responses are provided which include peptides consisting essentially of:

His-Leu-Asp-Met-Leu-Arg-His-Leu-Tyr-Gln-Gly-Cys-Gln-Val-Val; (Seq. ID No. 30)

Pro-Leu-Gln-Arg-Leu-Arg-Ile-Val-Arg-Gly-Thr-Gln-Leu-Phe-Glu; (Seq. ID No. 31)

Leu-Arg-Ser-Leu-Thr-Glu-Ile-Leu-Lys-Gly-Gly-Val-Leu-Ile-Gln; (Seq. ID No. 32)

Val-Thr-Tyr-Asn-Thr-Asp-Thr-Phe-Glu-Ser-Met-Pro-Asn-Pro-Glu; (Seq. ID No. 33)

His-Leu-Arg-Glu-Val-Arg-Ala-Val-Thr-Ser-Ala-Asn-Ile-Gln-Glu; (Seq. ID No. 34)

Val-Arg-Ala-Val-Thr-Ser-Ala-Asn-Ile-Gln-Glu-Phe-Ala-Gly-Cys; (Seq. ID No. 35)

Asn-Ile-Gln-Glu-Phe-Ala-Gly-Cys-Lys-Lys-Ile-Phe-Gly-Ser-Leu; (Seq. ID No. 36)

Gln-Val-Phe-Glu-Thr-Leu-Glu-Glu-Ile-Thr-Gly-Tyr-Leu-Tyr-Ile; (Seq. ID No. 37)

Gln-Glu-Cys-Val-Glu-Glu-Cys-Arg-Val-Leu-Gln-Gly-Leu-Pro-Arg; (Seq. ID No. 38)

Val-Val-Val-Leu-Gly-Val-Val-Phe-Gly-Ile-Leu-Ile-Lys-Arg-Arg; (Seq. ID No. 39)

Lys-Tyr-Thr-Met-Arg-Arg-Leu-Leu-Gln-Glu-Thr-Glu-Leu-Val-Glu; (Seq. ID No. 40)

Gly-Ala-Met-Pro-Asn-Gln-Ala-Gln-Met-Arg-Ile-Leu-Lys-Glu-Thr; (Seq. ID No. 41)

Val-Lys-Val-Leu-Gly-Ser-Gly-Ala-Phe-Gly-Thr-Val-Tyr-Lys-Gly; (Seq. ID No. 42)

Ser-Pro-Lys-Ala-Asn-Lys-Glu-Ile-Leu-Asp-Glu-Ala-Tyr-Val-Met; (Seq. ID No. 43)

Gly-Val-Gly-Ser-Pro-Tyr-Val-Ser-Arg-Leu-Leu-Gly-Ile-Cys-Leu; (Seq. ID No. 44)

Ser-Arg-Leu-Leu-Gly-Ile-Cys-Leu-Thr-Ser-Thr-Val-Gln-Leu-Val; (Seq. ID No. 45)

Gly-Ser-Gln-Asp-Leu-Leu-Asn-Trp-Cys-Met-Gln-Ile-Ala-Lys-Gly; (Seq. ID No. 46)

Val-Lys-Ile-Thr-Asp-Phe-Gly-Leu-Ala-Arg-Leu-Leu-Asp-Ile-Asp; (Seq. ID No. 47)

Thr-Val-Trp-Glu-Leu-Met-Thr-Phe-Gly-Ala-Lys-Pro-Tyr-Asp-Gly; (Seq. ID No. 48)

Pro-Ala-Arg-Glu-Ile-Pro-Asp-Leu-Leu-Glu-Lys-Gly-Glu-Arg-Leu; (Seq. ID No. 49)

Arg-Phe-Arg-Glu-Leu-Val-Ser-Glu-Phe-Ser-Arg-Met-Ala-Arg-Asp; (Seq. ID No. 50)

Glu-Asp-Asp-Asp-Met-Gly-Asp-Leu-Val-Asp-Ala-Glu-Glu-Tyr-Leu; (Seq. ID No. 51)

Gly-Met-Gly-Ala-Ala-Lys-Gly-Leu-Gln-Ser-Leu-Pro-Thr-His-Asp; (Seq. ID No. 52)

Thr-Cys-Ser-Pro-Gln-Pro-Glu-Tyr-Val-Asn-Gln-Pro-Asp-Val-Arg; (Seq. ID No. 53)

Thr-Leu-Glu-Arg-Pro-Lys-Thr-Leu-Ser-Pro-Gly-Lys-Asn-Gly-Val; (Seq. ID No. 54)

Gly-Gly-Ala-Val-Glu-Asn-Pro-Glu-Tyr-Leu-Thr-Pro-Gln-Gly-Gly; (Seq. ID No. 55)

Asn-Gln-Glu-Val-Thr-Ala-Glu-Asp-Gly-Thr-Gln-Arg-Cys-Glu-Lys; (Seq. ID No. 56)

Gln-Val-Ile-Arg-Gly-Arg-Ile-Leu-His-Asn-Gly-Ala-Tyr-Ser-Leu; (Seq. ID No. 57)

Leu-Gln-Val-Phe-Glu-Thr-Leu-Glu-Glu-Ile-Thr-Gly-Tyr-Leu-Tyr; (Seq. ID No. 58)

Ala-Ser-Pro-Leu-Thr-Ser-Ile-Ile-Ser-Ala-Val-Val-Gly-Ile-Leu; (Seq. ID No. 59)

Thr-Gln-Arg-Cys-Glu-Lys-Cys-Ser-Lys-Pro-Cys-Ala-Arg-Val-Cys-Tyr-Gly-Leu; (Seq. ID No. 60)

Arg-Leu-Arg-Ile-Val-Arg-Gly-Thr-Gln-Leu-Phe-Glu-Asp-Asn-Tyr-Ala-Leu; (Seq. ID No. 61)

Lys-Ile-Phe-Gly-Ser-Leu-Ala-Phe-Leu-Pro-Glu-Ser-Phe-Asp-Gly-Asp; (Seq. ID No. 62)

Arg-Arg-Leu-Leu-Gln-Glu-Thr-Glu-Leu-Val-Glu-Pro-Leu-Thr-Pro-Ser; or (Seq. ID No. 63)

Glu-Leu-Val-Ser-Glu-Phe-Ser-Arg-Met-Ala-Arg-Asp-Pro-Gln. (Seq. ID No. 64)

Additional peptides are provided and include a peptide consisting essentially of the amino acid sequence of FIG. 1 from lysine, amino acid 676, to valine, amino acid 1255.

These and other aspects of the present invention will become evident upon reference to the following detailed description and attached drawings.

BRIEF DESCRIPTION OF THE DRAWINGS

FIG. 1 shows that $p185^{HER-2/neu}$ protein (SEQ ID NO: 68) contains multiple segments with amino acid sequences appropriate for binding to class II MHC molecules. Each outlined amino acid represents the center point of an 11-mer peptide with alpha-helical periodicity and amphipathicity. Each underlined amino acid segment represents an epitope corresponding to Rothbard and Taylor motifs.

DETAILED DESCRIPTION OF THE INVENTION

Figure 2:
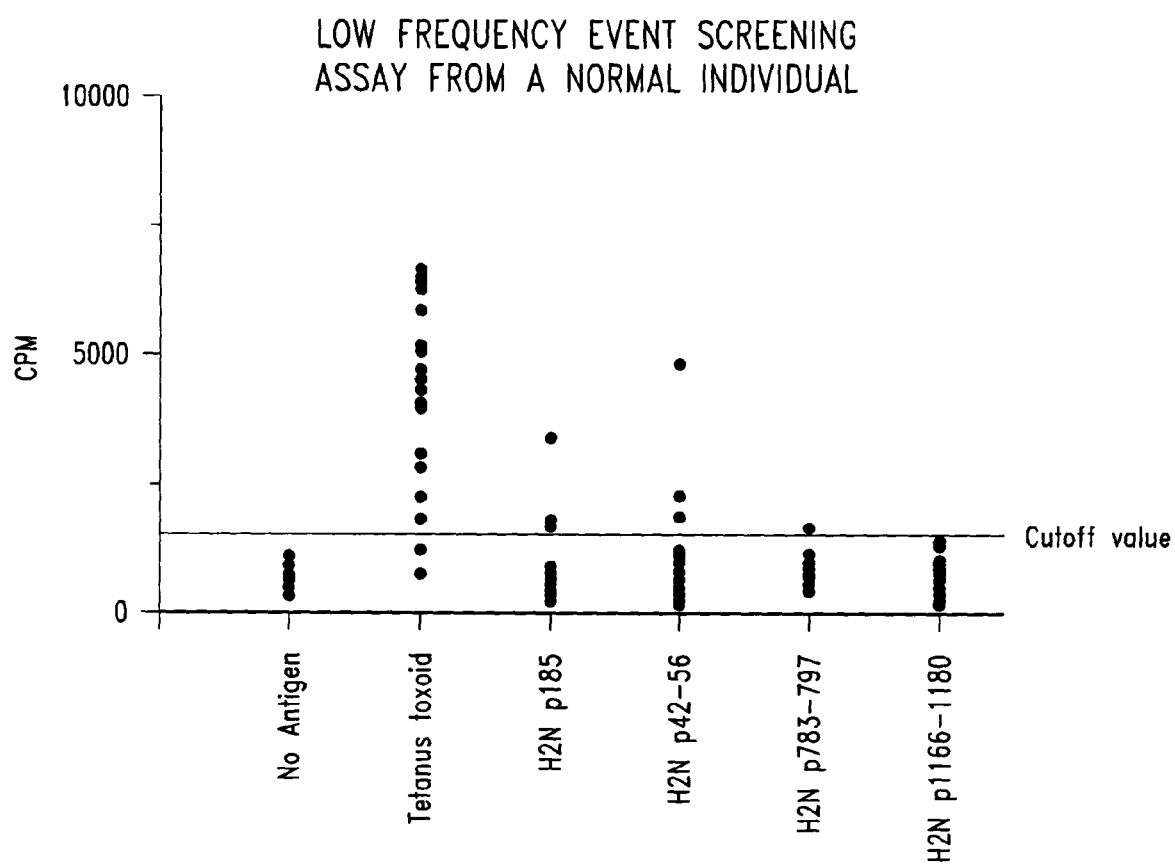
FIG. 2 graphically illustrates the results of a low frequency event screening from a normal individual indicating that a $CD4^+T$ cell response can be detected against $p185^{HER-2/neu}$ and peptides derived from its amino acid sequence. The graph represents the data from one normal individual analyzed with the low frequency screening assayed described further below. Positive responses to the intact protein and two peptides were detected.
Figure 3A:
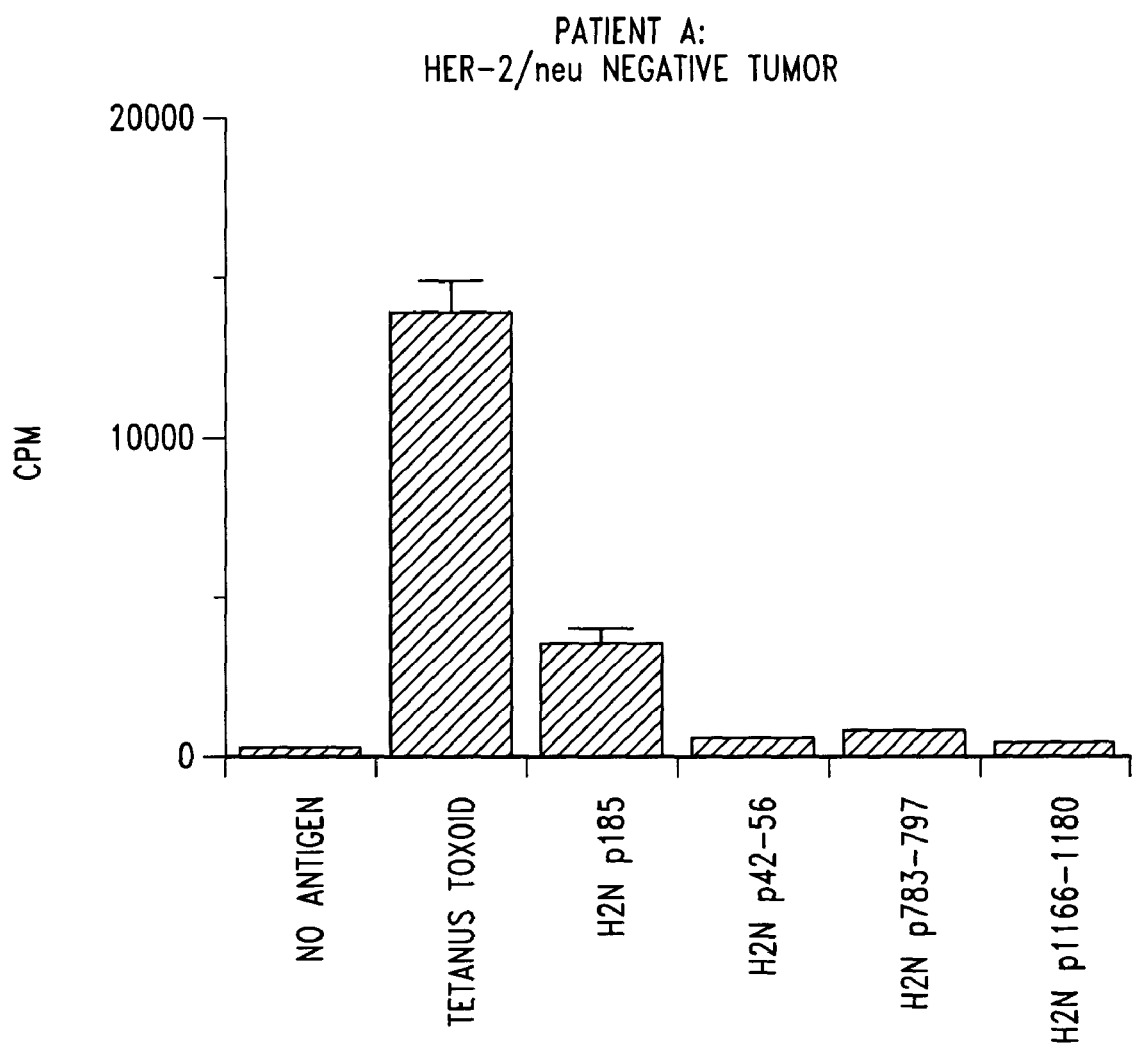
FIG. 3 (panels A-D) graphically illustrates that $CD4^+T$ cells reactive to $p185^{HER-2/neu}$ protein and peptides can be detected in high frequency from patients with HER-2/neu positive breast cancer and can also be detected in some patients with tumors that test negatively for expression of $p185^{HER-2/neu}$ protein. All four breast cancer patients represented here, patient A (panel A), patient B (panel B), patient C (panel C), and patient D (panel D), were premenopausal women. Patient A had a primary tumor that tested negatively for overexpression of $p185^{HER-2/neu}$. The other three patients had HER-2/neu positive tumors. A proliferation assay was performed using purified peripheral blood mononuclear cells (PBMC) as described below, with each experimental group done in 24 well replicate. Two×$10^5$ PBMC/well were incubated with no antigen, tetanus toxoid (5 µg/ml), $p185^{HER-2/neu}$ (50 µg/ml), or HER-2/neu derived peptides (50 µg/ml) as described further below. After 4 days, wells were pulsed with 1 µCi of tritiated thymidine ($^3$H-TdR) for 6-8 hours and then counted. The data represents the mean of 24 determinations of the c.p.m. with standard error bars expressed.
Figure 3B:
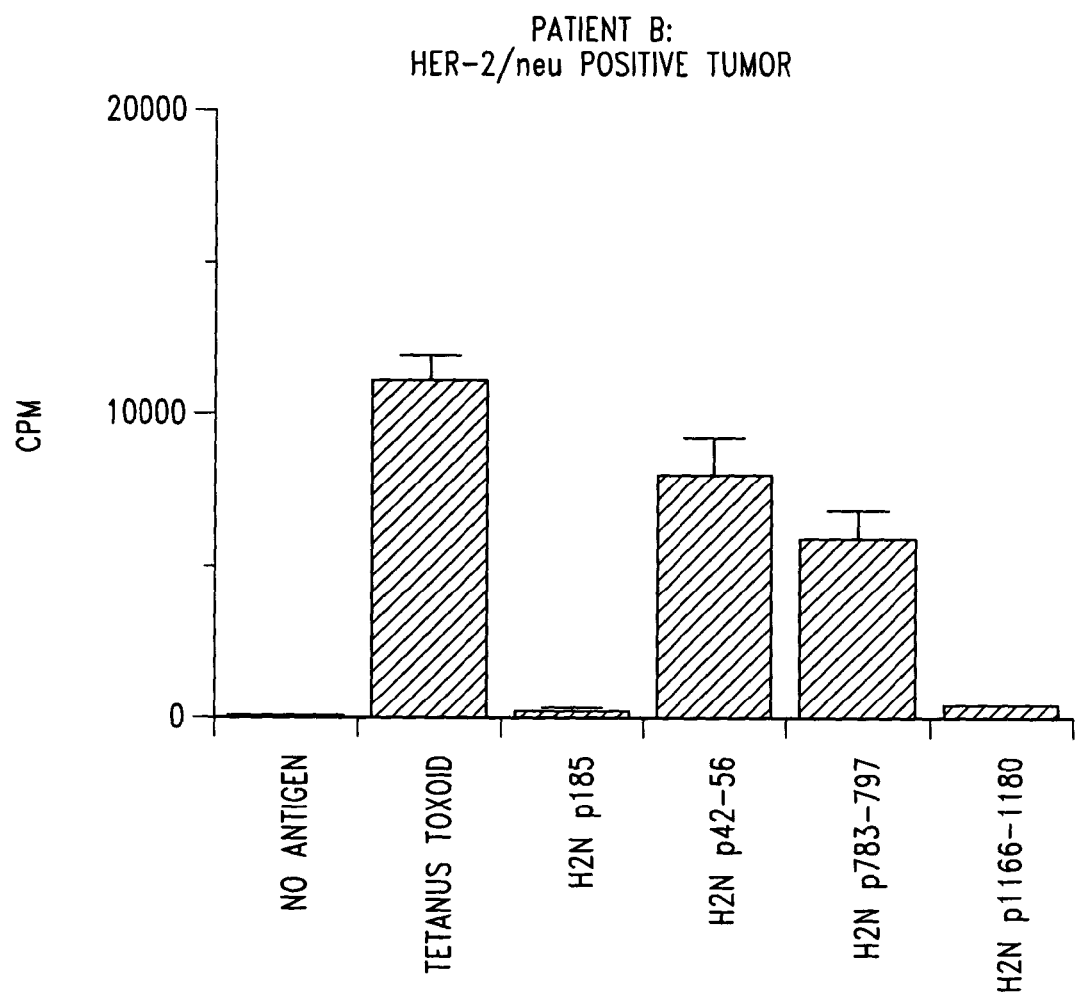
Figure 3C:
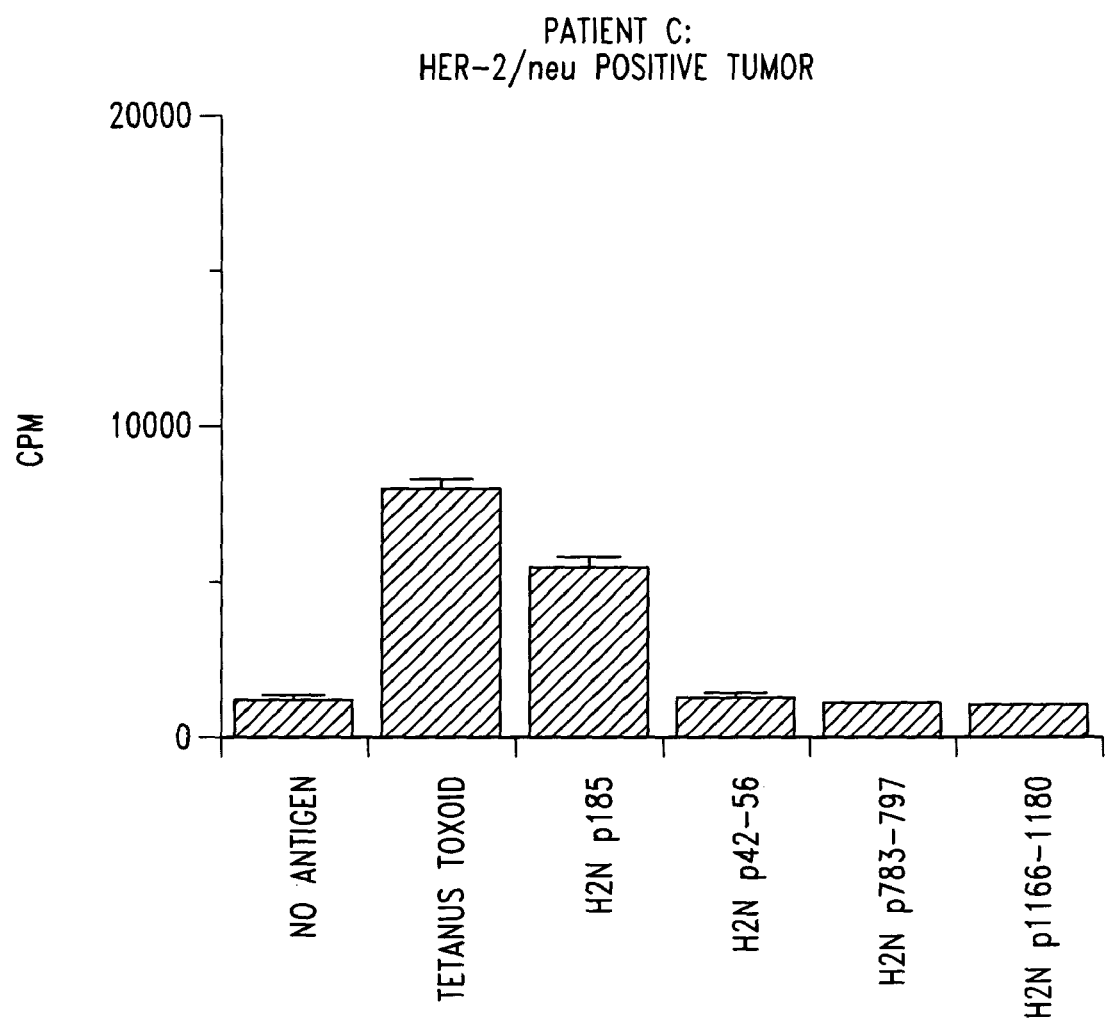
Figure 3D:
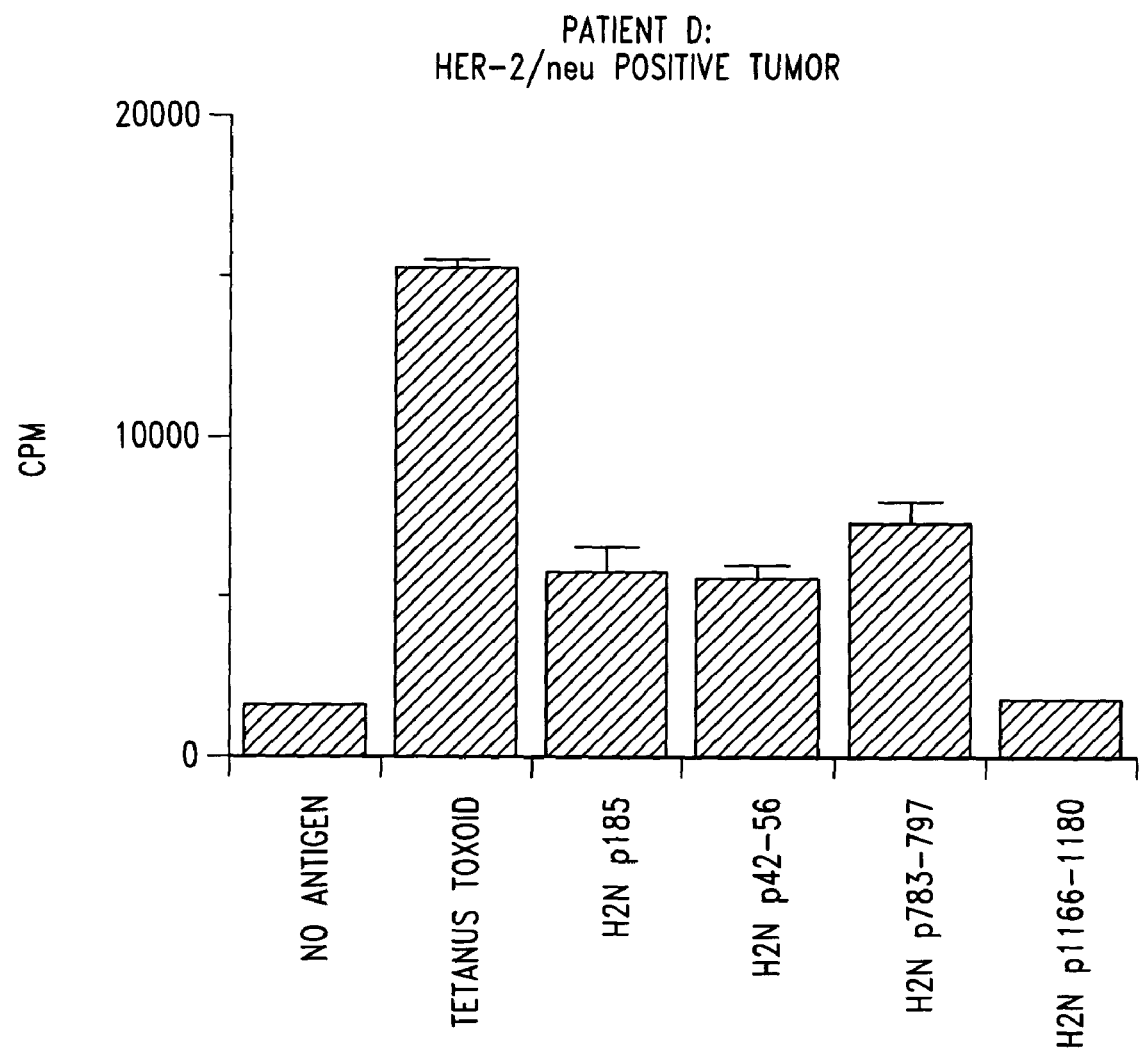

Prior to setting forth the invention, it may be helpful to an understanding thereof to set forth definitions of certain terms to be used hereinafter.

HER-2/neu Protein—as used herein, refers to the p185 protein (also known as c-erbB2) and peptides thereof which are recognized by helper T cells or cytotoxic T cells; and may be naturally derived, synthetically produced, genetically engineered, or a functional equivalent thereof, e.g., where one or more amino acids are replaced by other amino acid(s) or non-amino acid(s) which do not substantially affect function.

Proliferation of T cells—as used herein, includes the multiplication of T cells as well as the stimulation of T cells leading to multiplication, i.e., the initiation of events leading to mitosis and mitosis itself. Methods for detecting proliferation of T cells are discussed below.

As noted above, the present invention is directed toward methods and compositions for the diagnosis, monitoring and treatment of malignancies in a warm-blooded animal, wherein an amplified HER-2/neu gene is associated with the malignancies. Association of an amplified HER-2/neu gene with a malignancy does not require that the protein expression product of the gene be present on the tumor. For example, overexpression of the protein expression product may be involved with initiation of a tumor, but the protein expression may subsequently be lost. An effective autochthonous immune response may convert a HER-2/neu positive tumor to HER-2/neu negative, but existent immunity will be present and allow diagnosis.

More specifically, the disclosure of the present invention, in one aspect, shows that the protein expression product of the HER-2/neu gene can be recognized by thymus-dependent lymphocytes (hereinafter "T cells") and, therefore, the autochthonous immune T cell response can be utilized to diagnose, monitor and treat malignancies in which such a protein is or has been overexpressed. The disclosure of the present invention also shows, in another aspect, that sera of patients with a malignancy, in which an amplified HER-2/neu oncogene is associated, contain antibodies to HER-2/neu protein. The autochthonous antibody response can be used to diagnose, monitor and treat malignancies in which such a protein is overexpressed.

It is well known that the two major arms of the immune system are: (1) cell-mediated immunity with immune T cells and (2) humoral immunity with antibodies. Further, the immune system normally functions to recognize and destroy any foreign or aberrant cells in the body. Since the HER-2/neu protein is expressed by some normal cells, tolerance and/or anergy (i.e., diminished reactivity to a specific antigen) is expected. Thus, it is surprising that, as disclosed within the present invention, both T cell and antibody responses to HER-2/neu are detected.

In general, CD4+T cell populations are considered to function as helpers/inducers through the release of lymphokines when stimulated by a specific antigen; however, a subset of CD4+ cells can act as cytotoxic T lymphocytes (CTL). Similarly, CD8+T cells are considered to function by directly lysing antigenic targets; however, under a variety of circumstances they can secrete lymphokines to provide helper or DTH function. Despite the potential of overlapping function, the phenotypic CD4 and CD8 markers are linked to the recognition of peptides bound to class II or class I MHC antigens. The recognition of antigen in the context of class II or class I MHC mandates that CD4+ and CD8+T cells respond to different antigens or the same antigen presented under different circumstances. The binding of immunogenic peptides to class II MHC antigens most commonly occurs for antigens ingested by antigen presenting cells. Therefore, CD4+T cells generally recognize antigens that have been external to the tumor cells. By contrast, under normal circumstances, binding of peptides to class I MHC occurs only for proteins present in the cytosol and synthesized by the target itself, proteins in the external environment are excluded. An exception to this is the binding of exogenous peptides with a precise class I binding motif which are present outside the cell in high concentration. Thus, CD4+ and CD8+T cells have broadly different functions and tend to recognize different antigens as a reflection of where the antigens normally reside.

As disclosed within the present invention, the protein product expressed by the HER-2/neu oncogene is recognized by T cells. Such a protein expression product "turns over" within cells, i.e., undergoes a cycle wherein a synthesized protein functions and then eventually is degraded and replaced by a newly synthesized molecule. During the protein life cycle, peptide fragments from the protein bind to major histocompatibility complex (MHC) antigens. By display of a peptide bound to MHC antigen on the cell surface and recognition by host T cells of the combination of peptide plus self MHC antigen, a malignant cell will be immunogenic to T cells. The exquisite specificity of the T cell receptor enables individual T cells to discriminate between protein fragments which differ by a single amino acid residue.

During the immune response to a peptide, T cells expressing a T cell receptor with high affinity binding of the peptide-MHC complex will bind to the peptide-MHC complex and thereby become activated and induced to proliferate. In the first encounter with a peptide, small numbers of immune T cells will secrete lymphokines, proliferate and differentiate into effector and memory T cells. The primary immune response will occur in vivo but has been difficult to detect in vitro. Subsequent encounter with the same antigen by the memory T cell will lead to a faster and more intense immune response. The secondary response will occur either in vivo or in vitro. The in vitro response is easily gauged by measuring the degree of proliferation, the degree of cytokine production, or the generation of cytolytic activity of the T cell population re-exposed in the antigen. Substantial proliferation of the T cell population in response to a particular antigen is considered to be indicative of prior exposure or priming to the antigen.

Within one aspect of the present invention, a malignancy in which a HER-2/neu oncogene is associated may be detected. Representative examples of such malignancies include breast, ovarian, colon, lung and prostate cancers. An immune response to the HER-2/neu protein, once generated, can be long-lived and can be detected long after immunization, regardless of whether the protein is present or absent in the body at the time of testing. In one embodiment, prior exposure of a warm-blooded animal, such as humans, to the HER-2/neu protein can be detected by examining for the presence or absence of specific activation of CD4+ or CD8+T cells. More specifically, T cells isolated from an individual by routine techniques (such as by Ficoll/Hypaque density gradient centrifugation of peripheral blood lymphocytes) are incubated with HER-2/neu protein. For example, T cells may be incubated in vitro for 2-9 days (typically 4 days) at 37° C. with HER-2/neu protein (typically, 5 µg/ml of whole protein or 25 µg/ml of an appropriate peptide or graded numbers of cells synthesizing HER-2/neu protein). It may be desirable to incubate another aliquot of a T cell sample in the absence of HER-2/neu protein to serve as a control.

Specific activation of CD4+ or CD8+T cells may be detected in a variety of ways. Methods for detecting specific T cell activation include detecting the proliferation of T cells, the production of cytokines (e.g., lymphokines), or the generation of cytolytic activity (i.e., generation of cytotoxic T cells specific for HER-2/neu protein). For CD4+T cells, a preferred method for detecting specific T cell activation is the detection of the proliferation of T cells. For CD8+T cells, a preferred method for detecting specific T cell activation is the detection of the generation of cytolytic activity.

Detection of the proliferation of T cells may be accomplished by a variety of known techniques. For example, T cell proliferation can be detected by measuring the rate of DNA synthesis. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to intact $p185^{HER-2/neu}$ protein or peptide may be quantified.

Intact $p185^{HER-2/neu}$ protein or peptides thereof which are recognized by cytotoxic T cells may be used within the present invention. The peptides may be naturally derived or produced based upon an identified sequence. The peptides for CD8+T cell responses are generally 8-10 amino acids in length and the peptides for CD4+T cell responses are longer, e.g., 15-18 amino acids in length. Peptides for CD8+T cell responses vary according to each individual's class I MHC molecules. An example of peptides appropriate for CD8+T cell responses (elicited by peptides presented by HLA-A2.1 class I MHC molecules) are peptides which are 8-10 amino acids in length and contain a leucine at position 2 and/or a leucine or valine at position 9. Examples of peptides (designated by one letter abbreviations for amino acids and followed in parentheses by which residues of p185 they correspond) suitable within the present invention for CD8+T cell responses in individuals that are HLA-A2.1 include peptides consisting essentially of: HLYQGCQVV (p48-56) (Seq. ID No. 1); OLFEDNYAL (p106-114) (Seq. ID No. 26); KIFGSLAFL (p369-377) (Seq. ID No. 27); PLQPEQLQV (p391-399) (Seq. ID No. 2); PLTSIISAV (p650-658) (Seq. ID No. 3); ILLVVVLGV (p661-669) (Seq.

ID No. 4); LLVVVLGW (p662-670) (Seq. ID No. 5); RLLQETELV (p689-697) (Seq. ID No. 6); ILDEAYVMAGV (p767-777) (Seq. ID No. 28); VMAGVGSPYV (p773-782) (Seq. ID No. 29); CLTSTVQLV (p789-797) (Seq. ID No. 7); DLAARNVLV (p845-853) (Seq. ID No. 8); VLVKSPNHV (p851-859) (Seq. ID No. 9); TLSPGKNGV (p1172-1180) (Seq. ID No. 10); VLGVVFGIL (p666-674) (Seq. ID No. 11); LIKRRQQKI (p674-682) (Seq. ID No. 12); KIPVAIKVL (p747-755) (Seq. ID No. 13); ILDEAYVMA (p767-775) (Seq. ID No. 14); QLMPYGCLL (p799-807) (Seq. ID No. 15); QIAKGMSYL (p829-836) (Seq. ID No. 16); LLNWCMQIA (p822-830) (Seq. ID No. 17); RLVHRDLAA (p840-848) (Seq. ID No. 18); DIDETEYHA (p871-879) (Seq. ID No. 19); DLLEKGERL (p933-941) (Seq. ID No. 20); TIDVYMLMV (p948-956) (Seq. ID No. 21); MIMVKCWMI (p953-961) (Seq. ID No. 22); DLVDAEEYL (p1016-1024) (Seq. ID No. 23); GLEPSEEEA (p1062-1070) (Seq. ID No. 24); or YLTPQGGAA (p1196-1204) (Seq. ID No. 25).

Peptides for CD4$^+$T cell responses vary according to each individual's class II MHC molecules. Examples of peptides suitable within the present invention for CD4$^+$T cell responses include peptides consisting essentially of: HLDMLRHLYQGCQVV (p42-56) (Seq. ID No. 30); PLQRLRIVRGTQLFE (p95-109) (Seq. ID No. 31); RLRIVRGTQLFEDNYAL (p98-114) (Seq. ID No. 61); LRSLTEILKGGVLIQ (p142-156) (Seq. ID No. 32); VTYNTDTFESMPNPE (p272-286) (Seq. ID No. 33); NQEVTAEDGTQRCEK (p319-333) (Seq. ID No. 56); TQRCEKCSKPCARVCYGL (p328-345) (Seq. ID No. 60); HLREVRAVTSANIQE (p349-363) (Seq. ID No. 34); VRAVTSANIQEFAGC (p353-367) (Seq. ID No. 35); NIQEFAGCKKIFGSL (p360-374) (Seq. ID No. 36); KIFGSLAFLPESFDGD (p369-384) (Seq. ID No. 62); LQVFETLEEITGYLY (p397-411) (Seq. ID No. 58); QVFETLEEITGYLYI (p398-412) (Seq. ID No. 37); QVIRGRILHNGAYSL (p429-443) (Seq. ID No. 57); QECVEECRVLQGLPR (p538-552) (Seq. ID No. 38); ASPLTSIISAVVGIL (p648-662) (Seq. ID No. 59); VVVLGVVFGILIKRR (p664-678) (Seq. ID No. 39); KYTMRRLLQETELVE (p684-698) (Seq. ID No. 40); RRLLQETELVEPLTPS (p688-703) (Seq. ID No. 63); GAMPNQAQMRILKET (p704-718) (Seq. ID No. 41); VKVLGSGAFGTVYKG (p723-737) (Seq. ID No. 42); SPKANKEILDEAYVM (p760-774) (Seq. ID No. 43); GVGSPYVSRLLGICL (p776-790) (Seq. ID No. 44); SRLLGICLTSTVQLV (p783-797) (Seq. ID No. 45); GSQDLLNWCMQIAKG (p818-832) (Seq. ID No. 46); VKITDFGLARLLDID (p859-873) (Seq. ID No. 47); TVWELMTFGAKPYDG (p911-925) (Seq. ID No. 48); PAREIPDLLEKGERL (p927-941) (Seq. ID No. 49); RFRELVSEFSRMARD (p968-982) (Seq. ID No. 50); ELVSEFSRMARDPQ (p971-984) (Seq. ID No. 64); EDDDMGDLVDAEEYL (p1010-1024) (Seq. ID No. 51); GMGAAKGLQSLPTHD (p1091-1105) (Seq. ID No. 52); TCSPQPEYVNQPDVR (p1132-1146) (Seq. ID No. 53); TLERPKTLSPGKNGV (p1166-1180) (Seq. ID No. 54); or GGAVENPEYLTPQGG (p1188-1202) (Seq. ID No. 55).

It will be evident to those of ordinary skill in the art that other peptides may be produced for use within the present invention, both for the HLA-A2.1 class I MHC molecule as well as for the other class I and class II molecules. A variety of techniques are well known for isolating or constructing peptides. Suitable peptides are readily identified based upon the disclosure provided herein. Additional suitable peptides include those which are longer in length. For example, another peptide has an amino acid sequence corresponding to that disclosed in FIG. 1 beginning at about the lysine residue at amino acid position 676 and extending to about the valine residue at amino acid position 1255. Such a peptide may be extended (e.g., by the addition of one or more amino acid residues selected, for example, from position 675 to about position 646 of FIG. 1) and/or truncated (e.g., by the deletion of one or more amino acid residues from the carboxyl terminus which is position 1255 of FIG. 1). Alternatively, suitable peptides may be variations on other preferred peptides disclosed herein. For example, variations on the peptide designated herein as p650-658 include the extension and/or truncation by the addition or deletion, respectively, of one or more amino acid residues beginning at either position 650 or position 658 or both positions. As an example, four amino acids are removed from the amino terminus of p650-658 and four amino acids, such as the four adjacent to position 658, are added to its carboxyl terminus. Although this particular peptide variation results in a peptide with the same number of total amino acids (nine), a peptide variation on a preferred peptide need not be identical in length. Variations in amino acid sequence that yield peptides having substantially the same desired biological activity are within the scope of the present invention.

For therapeutic purposes, CD4$^+$ or CD8$^+$T cells that proliferate in the presence of HER-2/neu protein can be expanded in number either in vitro or in vivo. Proliferation of such T cells in vitro may be accomplished in a variety of ways. For example, the T cells can be re-exposed to HER-2/neu protein. It may be desirable to repeat the exposure of T cells to the HER-2/neu protein to induce proliferation. It may be further desirable to include T cell growth factors, such as interleukin-2, and/or stimulator cells which synthesize HER-2/neu protein. The addition of stimulator cells is preferred where generating CD8$^+$T cell responses. HER-2/neu protein-specific T cells can be grown to large numbers in vitro with retention of specificity in response to intermittent restimulation with the immunizing HER-2/neu protein. Briefly, for the primary in vitro stimulation (IVS), large numbers of lymphocytes (e.g., greater than $4 \times 10^7$) are placed in flasks with media containing human serum. HER-2/neu protein (e.g., peptide at 10 μg/ml) is added directly as well as 5 μg/ml tetanus toxoid. The flasks are incubated at 37° C. for 7 days. For the second IVS, at the end of the 7 days, $T_7$ cells are harvested and placed in new flasks with $2-3 \times 10^7$ irradiated peripheral blood mononuclear cells. HER-2/neu protein (e.g., peptide at 10 μg/ml is added directly). The flasks are incubated at 37° C. for 7 days. On day 2 and day 4 after the second IVS, 2-5 units of interleukin-2 (IL-2) is added. For the third IVS, the T cells are placed in wells (e.g., 24 well plates). The T cells are stimulated with the individual's own EBV transformed B cells coated with the peptide. IL-2 is added on days 2 and 4 of each cycle. As soon as the cells are shown to be specific cytotoxic T cells, they are changed to a 10 day stimulation cycle with higher IL-2 (20 units) on days 2, 4 and 6 to expand them.

Alternatively, one or more T cells that proliferate in the presence of HER-2/neu protein can be expanded in number by cloning. Methods for cloning cells are well known in the art. For example, T cell lines may be established in vitro and cloned by limiting dilution. Responder T cells are purified from the peripheral blood of sensitized patients by density gradient centrifugation and sheep red cell rosetting and established in culture by stimulating with the nominal antigen in the presence of irradiated autologous filler cells. In order to generate CD4$^+$T cell lines, HER-2/neu protein is used as the antigenic stimulus and autologous peripheral blood lymphocytes (PBL) or lymphoblastoid cell lines (LCL) immortalized by infection with Epstein Barr virus are used as antigen presenting cells. In order to generate $CD8^+T$ cell lines, autologous antigen-presenting cells transfected with an expression vector which produces relevant HER-2/neu protein may be used as stimulator cells. Established T cell lines are cloned 2-4 days following antigen stimulation by plating stimulated T cells at a frequency of 0.5 cells per well in 96-well flat-bottom plates with $1\times10^6$ irradiated PBL or LCL cells and recombinant interleukin-2 (rIL2) (50 U/ml). Wells with established clonal growth are identified at approximately 2-3 weeks after initial plating and restimulated with appropriate antigen in the presence of autologous antigen-presenting cells, then subsequently expanded by the addition of low doses of rIL2(10 U/ml) 2-3 days following antigen stimulation. T cell clones are maintained in 24-well plates by periodic restimulation with antigen and rIL2 approximately every two weeks.

Regardless of how an individual's T cells are proliferated in vitro, the T cells may be administered to the individual as an anti-cancer composition in an amount effective for therapeutic attack against a tumor. Thus, a patient's own T cells (autochthonous T cells) can be used as reagents to mediate specific tumor therapy. Typically, about $1\times10^9$ to $1\times10^{11}$ T cells/$M^2$ will be administered intravenously or intracavitary, e.g., in pleural or peritoneal cavities, or in the bed of a resected tumor. It will be evident to those skilled in the art that the number and frequency of administration will be dependent upon the response of the patient. Pharmaceutically suitable carriers or diluents for T cells include physiological saline or sera. It will be recognized by one skilled in the art that the composition should be prepared in sterile form.

T cells may also be proliferated in vivo. For example, immunization of an individual with a HER-2/neu peptide (i.e., as a vaccine) can induce continued expansion in the number of T cells necessary for therapeutic attack against a tumor in which the HER-2/neu oncogene is associated. Typically, about 0.01 μg/kg to about 100 mg/kg body weight will be administered by the intradermal, subcutaneous or intravenous route. A preferred dosage is about 1 μg/kg to about 1 mg/kg, with about 5 μg/kg to about 200 μg/kg particularly preferred. It will be evident to those skilled in the art that the number and frequency of administration will be dependent upon the response of the patient. It may be desirable to administer the HER-2/neu peptide repetitively. It will be evident to those skilled in this art that more than one HER-2/neu peptide may be administered, either simultaneously or sequentially. For example, a combination of about 8-15 peptides may be used for immunization. Preferred peptides for immunization are those that include all or a portion of the amino acid sequence shown in FIG. 1 beginning at about the lysine residue at amino acid position 676 and extending to about the valine residue at amino acid position 1255. One or more peptides from other portions of the amino acid sequence shown in FIG. 1 may be added to one or more of the preferred peptides. Neither intact p185$^{HER-2/neu}$ protein nor a peptide having the amino acid sequence of its entire extracellular domain (i.e., a peptide having an amino acid sequence of the entire amino acid sequence shown in FIG. 1 up to amino acid position 650, plus or minus about one to five positions, and with or without the first 21 amino acid positions) are used alone for immunization.

In addition to the HER-2/neu peptide (which functions as an antigen), it may be desirable to include other components in the vaccine, such as a vehicle for antigen delivery and immunostimulatory substances designed to enhance the protein's immunogenicity. Examples of vehicles for antigen delivery include aluminum salts, water-in-oil emulsions, biodegradable oil vehicles, oil-in-water emulsions, biodegradable microcapsules, and liposomes. Examples of immunostimulatory substances (adjuvants) include N-acetylmuramyl-L-alanine-D-isoglutamine (MDP), lipopolysaccharides (LPS), glucan, IL-12, GM-CSF, gamma interferon and IL-15. It will be evident to those skilled in this art that a HER-2/neu peptide may be prepared synthetically or that a portion of the protein (naturally-derived or synthetic) may be used. When a peptide is used without additional sequences, it may be desirable to couple the peptide hapten to a carrier substance, such as keyhole limpet hemocyanin.

The present invention also discloses that HER-2/neu protein, in addition to being immunogenic to T cells, appears to stimulate B-cells to produce antibodies capable of recognizing HER-2/neu protein. Detection of such antibodies provides another way to diagnose a malignancy in which a HER-2/neu oncogene is associated with the malignancy. Antibodies specific (i.e., which exhibit a binding affinity of about $10^7$ liters/mole or better) for HER-2/neu protein may be found in a variety of body fluids including sera and ascites. Briefly, a body fluid sample is isolated from a warm-blooded animal, such as a human, for whom it is desired to determine whether antibodies specific for HER-2/neu are present. The body fluid is incubated with HER-2/neu protein under conditions and for a time sufficient to permit immunocomplexes to form between the protein and antibodies specific for the protein. For example, a body fluid and HER-2/neu protein may be incubated at 4° C. for 24-48 hours. Following the incubation, the reaction mixture is tested for the presence of immunocomplexes. Detection of one or more immunocomplexes formed between HER-2/neu protein and antibodies specific for HER-2/neu protein may be accomplished by a variety of known techniques, such as radioimmunoassays (RIA) and enzyme linked immunosorbent assays (ELISA).

Suitable immunoassays include the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh, 1970); the "western blot" method of Gordon et al. (U.S. Pat. No. 4,452,901); immunoprecipitation of labeled ligand (Brown et al., *J. Biol. Chem*. 255:4980-4983, 1980); enzyme-linked immunosorbent assays as described by, for example, Raines and Ross (*J. Biol. Chem*. 257:5154-5160, 1982); immunocytochemical techniques, including the use of fluorochromes (Brooks et al., *Clin. Exp. Immunol*. 39: 477, 1980); and neutralization of activity [Bowen-Pope et al., *Proc. Natl. Acad. Sci. USA* 81:2396-2400 (1984)], all of which are hereby incorporated by reference. In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876, all of which are herein incorporated by reference.

For detection purposes, HER-2/neu protein ("antigen") may either be labeled or unlabeled. When unlabeled, the antigen find use in agglutination assays. In addition, unlabeled antigen can be used in combination with labeled molecules that are reactive with immunocomplexes, or in combination with labeled antibodies (second antibodies) that are reactive with the antibody directed against HER-2/ neu protein, such as antibodies specific for immunoglobulin. Alternatively, the antigen can be directly labeled. Where it is labeled, the reporter group can include radioisotopes, fluorophores, enzymes, luminescers, or dye particles. These and other labels are well known in the art and are described, for example, in the following U.S. Pat. Nos. 3,766,162; 3,791,932; 3,817,837; 3,996,345; and 4,233,402.

Typically in an ELISA assay, antigen is adsorbed to the surface of a microtiter well. Residual protein-binding sites on the surface are then blocked with an appropriate agent, such as bovine serum albumin (BSA), heat-inactivated normal goat serum (NGS), or BLOTTO (buffered solution of nonfat dry milk which also contains a preservative, salts, and an antifoaming agent). The well is then incubated with a sample suspected of containing specific antibody. The sample can be applied neat, or, more often, it can be diluted, usually in a buffered solution which contains a small amount (0.1%-5.0% by weight) of protein, such as BSA, NGS, or BLOTTO. After incubating for a sufficient length of time to allow specific binding to occur, the well is washed to remove unbound protein and then incubated with an anti-species specific immunoglobulin antibody labeled with a reporter group. The reporter group can be chosen from a variety of enzymes, including horseradish peroxidase, beta-galactosidase, alkaline phosphatase, and glucose oxidase. Sufficient time is allowed for specific binding to occur, then the well is again washed to remove unbound conjugate, and the substrate for the enzyme is added. Color is allowed to develop and the optical density of the contents of the well is determined visually or instrumentally.

In one preferred embodiment of this aspect of the present invention, a reporter group is bound to HER-2/neu protein. The step of detecting immunocomplexes involves removing substantially any unbound HER-2/neu protein and then detecting the presence or absence of the reporter group.

In another preferred embodiment, a reporter group is bound to a second antibody capable of binding to the antibodies specific for HER-2/neu protein. The step of detecting immunocomplexes involves (a) removing substantially any unbound antibody, (b) adding the second antibody, (c) removing substantially any unbound second antibody and then (d) detecting the presence or absence of the reporter group. Where the antibody specific for HER-2/neu protein is derived from a human, the second antibody is an anti-human antibody.

In a third preferred embodiment for detecting immunocomplexes, a reporter group is bound to a molecule capable of binding to the immunocomplexes. The step of detecting involves (a) adding the molecule, (b) removing substantially any unbound molecule, and then (c) detecting the presence or absence of the reporter group. An example of a molecule capable of binding to the immunocomplexes is protein A.

It will be evident to one skilled in the art that a variety of methods for detecting the immunocomplexes may be employed within the present invention. Reporter groups suitable for use in any of the methods include radioisotopes, fluorophores, enzymes, luminescers, and dye particles.

In a related aspect of the present invention, detection of immunocomplexes formed between HER-2/neu protein and antibodies in body fluid which are specific for HER-2/neu protein may be used to monitor the effectiveness of cancer therapy for a malignancy in which the HER-2/neu oncogene is associated. Samples of body fluid taken from an individual prior to and subsequent to initiation of therapy may be analyzed for the immunocomplexes by the methodologies described above. Briefly, the number of immunocomplexes detected in both samples are compared. A substantial change in the number of immunocomplexes in the second sample (post-therapy initiation) relative to the first sample (pre-therapy) reflects successful therapy.

The following examples are offered by way of illustration and not by way of limitation.

EXAMPLES

Example 1

CD4+T Cells Responsive to p185(HER-2/neu) Protein and Peptides can be Detected in Higher Frequency in Patients with Breast Cancer than Normal Individuals A. p185(HER-2/neu) Protein Contains Multiple Segments with Amino Acid Sequences Appropriate for Binding to Class II MHC Molecules Soluble proteins are classically processed in the class II MHC pathway. $p185^{HER-2/neu}$ protein is a transmembrane protein present at the cell surface. When overexpressed, it has been found to be soluble and in the extracellular environment both in vitro and in vivo. In vitro studies of human breast cancer cell lines found the extracellular domain of $p185^{HER-2/neu}$ in culture media of rapidly growing cells (Alper et al., *Cell Growth and Differentiation* 1:591-599, 1990; Zabrecky et al., *J. Biol. Chem.* 266:1716-1720, 1991). In vivo studies identified circulating portions of the protein in the sera of patients with breast cancer (Leitzel et al., *J. Clin. Oncol.* 10:1436-1443, 1992; Mori et al., *Jpn. J. Cancer Res.* 81:489-494, 1990).

Peptide segments of the parental HER-2/neu protein with a motif with theoretical potential to bind to class II MHC molecules were identified herein. Locating potential T cell epitopes was aided by computer analysis. A protein sequence analysis package, T Sites, that incorporates several computer algorithms designed to distinguish potential sites for T cell recognition was used (Feller and de la Cruz, *Nature* 349:720-721, 1991). Two searching algorithms were used: (1) the AMPHI algorithm described by Margalit (Feller and de la Cruz, *Nature* 349:720-721, 1991; Margalit et al., *J. Immunol.* 138:2213-2229, 1987) identified epitope motifs according to alpha-helical periodicity and amphipathicity; (2) the Rothbard and Taylor algorithm identified epitope motifs according to charge and polarity pattern (Rothbard and Taylor, *EMBO* 7:93-100, 1988). Segments with both motifs are most appropriate for binding to class II MHC molecules, with the caveat that each particular MHC molecule has a particular binding motif. Using this analysis, more than 40 potential T cell epitopes in the HER-2/neu protein corresponding to the AMPHI and the Rothbard motifs that would have the potential for binding to class II MHC molecules were identified (FIG. 1).

Peptides, each 15 amino acids in length, that encompass both the AMPHI and Rothbard motifs were constructed. The optimal peptide length for class II MHC binding depends upon the particular MHC molecule and may be shorter than 15 amino acids. However, class II MHC responses to exogenous peptides allow for endocytosis and intracellular processing of longer peptides. One of the synthetic peptides (p42-56), HLDMLRHLYQGCQVV (Seq. ID No. 30), is located in the extracellular domain and has 33% homology to epidermal growth factor receptor (EGFR). Two other synthetic peptides, SRLLGICLTSTVQLV (p783-797) (Seq. ID No. 45) and TLERPKTLSPGKNGV (p1166-1180) (Seq. ID No. 54) are both located in the intracellular domain and have 87% and 7% homology to EGFR respectively. The peptides as well as partially purified whole protein (p185$^{HER-2/neu}$) were used in subsequent defined experiments to detect CD4+T cell proliferation responses (Section C below).

B. p185(HER-2/neu) Protein can be Obtained and Purified from the Human Breast Adenocarcinoma Cell Line SKBR3

Purified p185 for T cell proliferation studies and antibody detection studies was obtained from the cell line SKBR3. SKBR3 has been reported on extensively in the literature as a commonly used standard cell line with increased HER-2/neu gene copy number and HER-2/neu protein overexpression. In one study, SKBR3 cells were found to contain a mean HER-2/neu oncogene copy number of 43 copies/cell compared with 2.5 copies/cell for MCF-7, a breast cancer cell line considered to be a standard cell line without HER-2/neu gene amplification (Kallionieme et al., *Proc. Nat. Acad. Sci. USA* 89:5321-5325, 1992). SKBR3 is reported to be one of the highest known expressors of p185$^{HER-2/neu}$ protein by immunohistochemistry, 4+ compared to 1+ in MCF-7 (Kerns et al., *J. Histochem. & Cytochem.* 38:1823-1830, 1990). The same HER-2/neu bands as described in the literature were validated in the present experiments by Western analysis. Bands detected included p185, p105 (extracellular domain), and several smaller bands that presumably represent fragments of phosphorylated protein (Alper et al., *Cell Growth and Differentiation* 1:591-599, 1990; Zabrecky et al., *J. Biol. Chem.* 266:1716-1720, 1991; Stern et al., *Mol. Cell. Biol.* 8:3969-3973, 1988).

The antibodies used for detecting the HER-2/neu protein immunoblotting were commercially prepared by Oncogene Science (Manhasset, N.Y.). The antibody most commonly used in the present experiments was c-neu Ab-3; derived by immunization of BALB/c mice with a peptide sequence, TAENPEYLGLDVPV (Seq. ID No. 65), from the carboxyl domain of human c-neu gene product, and fusion of mouse splenocytes with SP2/0 myeloma cells. A second antibody, c-neu AB-1, gave very faint bands when compared with c-neu Ab-3. This antibody was a polyclonal rabbit affinity purified antibody against the peptide sequence, LARLL-DIDETEYAD (Seq. ID No. 66), from the kinase domain of the human c-neu gene product.

Transmembrane p185$^{HER-2/neu}$ protein was purified from the cell membrane fraction of SKBR3 by modifications of described methods for other membrane-associated proteins (Dhut et al, *Leukemia* 4:745-750, 1990; Mietzner et al., *J. Exp. Med.* 165:1041-1057, 1987). Three×10$^6$ SKBR3 cells were harvested and suspended in phosphate buffered saline (PBS) with the following protease inhibitors; 1 mM PMSF, 1 mM benzamidine, 5 µg/ml aprotinin. All procedures were done on ice or at 4° C. The cells were then disrupted by sonication at 75W for a total of 1 minute using a high intensity sonifier equipped with a microtip (Branson Instruments, Inc., Stamford, Conn.). The resulting suspension was then centrifuged for 1 hour at 35,000 rpm to sediment membranes from cytosolic fraction. The membrane pellet was washed in ice cold PBS with protease inhibitors and the cycle of sonication/centrifugation was repeated twice. All cytosolic (supernatant) and membranous fractions were tested for the presence of p185$^{HER-2/neu}$ by Western analysis. The protein was noted to be strongly concentrated in the membrane fraction.

Protein concentration of one of these enriched membrane pellets was determined to be 2625 µg/ml (Protein BioRad assay). p185$^{HER-2/neu}$ is an estimated 8% of membrane protein in SKBR3 (Leitzel et al., *J. Clin. Oncol.* 10:1436-1443, 1992); therefore, an estimated 210 µg of p185$^{HER-2/neu}$ were present in the membrane pellet from 3×10$^6$ SKBR3 cells.

If desired, the membrane preparation may be further enriched for p185$^{HER-2/neu}$, e.g., by immunoprecipitation. Briefly, 1 µg of c-neu 3 antibody and 15 µl protein A agarose were added to the sonicated membrane pellet. The mixture was incubated at 4° C. on a rocker for 24 hours. The immunoprecipitate was collected by centrifugation in a micro-centrifuge at 2500 rpm for 15 minutes at 4° C., and the resulting pellet was washed several times with PBS, 1% Trition X-100, 0.5% sodium deoxycholate, and 0.1% sodium dodecyl sulfate. Silver stain and Western analysis showed increased concentration of p185$^{HER-2/neu}$ protein and decreases in extraneous membrane proteins when compared to membrane enriched pellets alone.

C. CD4+T Cells Reactive to p185(HER-2/neu) Protein can be Elicited from PBL of Normal Individuals by Using an Assay Designed for Detecting Low Frequency Lymphocyte Precursors Three assays were used for the detection of CD4$^+$ responses: a standard proliferation assay, a screening method for low frequency events, and a limiting dilution assay (LDA). Conventional proliferative assays are capable of readily detecting primed responses. The proliferative response stimulation index provides a rough correlation with precursor frequency of antigen-reactive T cells. Any specific proliferative response detected from PBL is considered to be a primed response.

To provide a more quantitative interpretation of CD4$^+$T cell responses, the assay system developed for detecting low lymphocyte precursor frequency responses (described below) is used. This assay is simple and cost-effective. In circumstances in which more precision is needed, the precursor frequency is validated by limiting dilution assays (Bishop and Orosz, *Transplantation* 47:671-677, 1989).

Responses greater than detected in normal individuals are defined as a primed response and imply existent immunity. Low responses, detectable only by LDA conditions are considered to be unprimed responses. An absent response by LDA or a response lower than that defined by the normal population analysis is considered to be tolerance/anergy.

In general, primed CD4$^+$T cell responses can be detected in conventional proliferative assays, whereas unprimed responses are not detectable in the same assays. Detection of small numbers of unprimed T cells is limited by confounding background thymidine uptake including the autologous mixed lymphocyte response (AMLR) to self MHC antigen plus responses to processed self serum proteins and exogenously added serum proteins.

To elicit and detect unprimed T cells, an assay system for low frequency responses based on Poisson sampling statistics was used (In: *Pinnacles*, Chiron Corporation, 1:1-2, 1991). This type of analysis applies specifically to low frequency events in that, if the precursor frequency is less than the number of cells in one replicate culture, many replicates are required to detect a statistically significant number of positives. Theoretically, the analysis will correct for autologous responses by setting up a known positive control (such as PHA or tetanus toxoid) and known negative control (no antigen) and evaluating all data points from lowest to highest irrespective of the experimental group to which they belong. A cutoff value is calculated based on the equation cutoff=M+(F+SD), where M=arithmetic mean, F=3.29, a factor from tables of standardized normal distribution chosen so not more than 0.1% of the "true negatives" of a normally distributed background will be above the cutoff, and SD=standard deviation. In this screening assay, wells above the cutoff are considered true positives that potentially contain a lymphocyte that is specifically proliferating to the antigen of interest. Although estimations of lymphocyte precursor frequency is possible using this method, precise determination requires formal LDA analysis.

Analysis of PBL from normal individuals for HER-2/neu peptide and protein-specific T cells revealed the presence of a low level frequency of proliferative responses. A representative assay is described in FIG. 2. Seven normal subjects were analyzed, 4 males and 3 females. Of the seven individuals evaluated, 57% had a response to whole protein and 29% had a response to at least one individual peptide. The two individuals that responded to peptide also had responses to parental protein. Three males and one female had detectable responses to the whole protein. Two males responded to one of the four peptides. Similar methods can be used to elicit HER-2/neu reactive T cells from patients with HER-2/neu positive malignancies, but no prior priming in vivo. Alternatively, the methods can be used to assess the efficacy of priming to HER-2/neu in vivo and the procurement of immune T cells to be expanded for therapy.

D. CD4+T Cells Reactive to p185(HER-2/neu) and Peptide can be Detected in the Peripheral Blood of Patients with HER-2/neu Positive Breast Cancer in Levels Consistent with a Primed Response Four breast cancer patients with known HER-2/neu tumor status have been evaluated in a standard proliferation assay. Three patients had tumors which overexpressed the HER-2/neu protein. Proliferation to antigen was consistent with a primed response (FIG. 3) (i.e., proliferation was detectable in a standard proliferation assay with a Stimulation Index (S.I.) greater than 2). One patient was HER-2/neu negative and had a response towards intact HER-2/neu, but no response to HER-2/neu-derived peptides. The patients tested and chosen had different stages of disease and were in different stages of treatment. Five normal individuals' responses were analyzed in the same fashion, and none had an S.I. greater than 2 to any HER-2/neu protein or peptide (Table 1).

TABLE 1

| Patient | HER-2/neu Status | TetanusT oxoid | p185 | p42–56 | p783–797 | p1166–1180 |
|---|---|---|---|---|---|---|
| (a) Breast Cancer patients ||||||| 
| A | Negative | 52 | 13 | 2 | 2 | 2 |
| B | Positive | 36 | <2 | 26 | 19 | 2 |
| C | Positive | 7 | 4 | <2 | <2 | <2 |
| D | Positive | 10 | 4 | 4 | 5 | <2 |

| Normal | TetanusT oxoid | p185 | p42–56 | p783–797 | p1166–1180 |
|---|---|---|---|---|---|
| (b) Normal Individuals |||||| 
| 1 | 6 | 2 | 2 | <2 | <2 |
| 2 | 7 | <2 | 2 | <2 | <2 |
| 3 | 7 | <2 | <2 | <2 | <2 |
| 4 | 10 | 2 | ND | ND | <2 |
| 5 | 11 | 2 | ND | ND | 2 |

Example 2

CD8+CTL Specific for HER-2/neu Peptides can be Generated from PBL of Normal Individuals by Primary in Vitro Immunization to Synthetic Peptides Derived from the Normal Amino Acid Sequence of p185(HER-2/neu) Protein A. p185(HER-2/neu) Protein Contains Multiple Segments with an Amino Acid Sequence Motif Appropriate for Binding the Class I MHC Molecule HLA-A2.1

CD8+T cells recognize peptide bound to class I MHC molecules. In general, peptide determinants are derived from endogenously synthesized proteins. The rules which determine the ability of a protein to be processed and complexed with class I MHC molecules are not completely understood. Recently, however, it has been determined that peptides binding to particular MHC molecules share discernible sequence motifs (Falk et al., Nature 351:290-296, 1991). A peptide motif for binding in the groove of HLA-A2.1 has been defined by Edman degradation of peptides stripped from HLA-A2.1 molecules of a cultured cell line (Table 2, from Falk et al., supra). The method identified the typical or average HLA-A2.1 binding peptide as being 9 amino acids in length with dominant anchor residues occurring at positions 2 (L) and 9 (V). Commonly occurring strong binding residues have been identified at positions 2 (M), 4 (E,K), 6 (V), and 8 (K). The identified motif represents the average of many binding peptides.

TABLE 2

The HLA-A2.1 Restricted Motif

| | Amino Acid Position ||||||||| Point Assignment |
|---|---|---|---|---|---|---|---|---|---|---|
| | 1 | 2 | 3 | 4 | 5 | 6 | 7 | 8 | 9 | |
| Dominant Binding Anchor Residue | | L | | | | | V | | | +3 |
| Strong Binding Residue | | M | K | E | | V | | K | | +2 |
| Weak Binding Residue | I | A | G | I | I | A | E | L | | +1 |
| | L | Y | P | K | L | Y | S | | | |
| | F | F | D | Y | T | H | | | | |
| | K | P | T | N | | | | | | |
| | M | M | | G | | | | | | |
| | Y | S | | V | | | | | | |
| | | | | H | | | | | | |

The derived peptide motif as currently defined is not particularly stringent. Some HLA-A2.1 binding peptides do not contain both dominant anchor residues and the amino acids flanking the dominant anchor residues play major roles in allowing or disallowing binding. Not every peptide with the current described binding motif will bind, and some peptides without the motif will bind. However, the current motif is valid enough to allow identification of some peptides capable of binding.

According to the current motif, the p185$^{HER-2/neu}$ protein contains a substantial number of peptides with amino acid sequences possibly appropriate for binding to the class I MHC antigen HLA-A2.1. Evaluation of the 1255 aa structure of p185$^{HER-2/neu}$ revealed at least 19 peptide segments of 9 aa in length that contained at least one of the dominant anchor residues. Of note, the current HLA-A2.1 motif places 6 amino acids between the dominant anchor amino acids at residues 2 and 9. Recent studies show that alterations in secondary structure of peptides can sometimes allow for additional intervening residues, and thus longer binding peptides. In the present experiment, 9-mer peptides were evaluated. The 10 peptides with both dominant residues were considered. The arbitrary scoring system awarded +3 for a dominant anchor residue, +2 for a strong binding residue, and +1 for a weak binding residue. Emphasis was placed on presence or absence of dominant anchor residues as they appear to be of prime importance for peptide binding to HLA-A2 (Parker et al., *J. Immunol.* 148:3580-3587, 1992). Four peptides were synthesized (Table 3). One is located in the extracellular domain of the protein and three are located in the intracellular domain. Homology to EGFR ranges from 11% to 89% (Bargmann et al., *Nature* 319:226-230, 1986).

TABLE 3 p185$^{HER-2/neu}$ Peptides Constructed for Binding in HLA-A2.1 Motif

| p185$^{HER-2/neu}$ Peptides | Amino Acid Position | | | | | | | | | Score | Location | Homology to EGFR |
|---|---|---|---|---|---|---|---|---|---|---|---|---|
| | 1 | 2 | 3 | 4 | 5 | 6 | 7 | 8 | 9 | | | |
| p 48–56$^{HER-2/neu}$ (Seq. ID No. 1) | H | L | Y | Q | G | C | Q | V | V | 8* | Extracellular | 33% |
| p 789–797$^{HER-2/neu}$ (Seq. ID No. 7) | C | L | T | S | T | V | Q | L | V | 9* | Intracellular | 89% |
| p 851–859$^{HER-2/neu}$ (Seq. ID No. 9) | V | L | V | K | S | P | N | H | V | 9* | Intracellular | 78% |
| p 1172–1180$^{HER-2/neu}$ (Seq. ID No. 10) | T | L | S | P | G | K | N | G | V | 9* | Intracellular | 11% |

*Peptide contains both dominant anchor residues

B. Four of Four Peptides with a Motif Theoretically Appropriate for Binding to HLA-A2.1 can be Shown to Actually Bind to HLA-A2.1 in a Class I MHC Molecule Stabilization Assay Having identified and synthesized peptides with a theoretical likelihood of binding to HLA-A2.1, the constructed peptides were evaluated as to whether in fact they could bind, the sine quo non of cytotoxic T lymphocytes (CTL) generation. Of the four peptides constructed, all could be shown to bind to HLA-A2 in an assay utilizing the mutant cell line T2. T2 is a human T-B cell hybrid that has a large homozygous deletion within the MHC gene region (Riberdy and Cresswell, *J. Immunol.* 148:2586-2590, 1992; Trousdale et al., *Nature* 348:741-744, 1990; Spies et al., *Nature* 348:744-747, 1990). The use of T2 to determine HLA-A2.1 binding peptides has been well defined. T2 does not appropriately process endogenous antigen for presentation with class I MHC molecules. Consequently, cell surface expression of class I MHC molecules is markedly reduced. However, provision of exogenous peptides which bind to and stabilize class I MHC in the presence of B2 microglobulin results in increased levels of class I at cell surface which can be easily detected by immunofluorescent staining. T2 without exogenous peptide has low expression of HLA-A2 (30%-50%). When incubated with peptides able to bind A2, the level of class I MHC stabilizes on the cell surface and can be measured by immunofluorescent staining. Thus, the T2 line fails to present internal proteins in the class I pathway, but can bind exogenous peptides, providing that the exogenous peptides have the appropriate HLA-A2.1 binding motif.

In this experiment, 1×10$^6$ T2 cells were incubated with individual peptides at a concentration of 25 µg/ml for 18 hours at 37° C. Binding of peptides to HLA-A2 was determined by immunofluorescent staining with a mouse monoclonal HLA-A2 antibody followed by rabbit antimouse IgG-FITC conjugate. The peptides which bound HLA-A2 increased class I surface expression to 60%-85% (10-15 percentage points over baseline).

C. CD8$^+$CTL Specific for HER-2/neu p48-56 and p789-797 can be Generated by Primary in Vitro Immunization In general, detection of T cell responses in vitro implies prior priming has occurred in vivo. It has been difficult and rare to generate CTL in vitro from unprimed populations.

Conditions for detecting immunity to standard recall antigens were used and no peptide-specific CTL could be detected. A set of conditions were derived which have allowed priming to 4 of 4 of the binding peptides tested to date. The conditions were derived by empiric experimentation but are consistent with the current paradigm. Conditions include: (1) large numbers of T cells; (2) a concurrent stimulated primed CD4$^+$T cell response; (3) IL-2 added late to culture in very small amounts; and (4) multiple restimulations.

Initial experiments examined response to p48-56 which is normally present in the extracellular domain and p789-797 which is normally present in the intracellular domain, both of which were found to bind to HLA-A2.1. Four of four peptides with a motif theoretically appropriate for binding to HLA-A2.1 are shown to actually bind to HLA-A2.1 in a class I MHC molecule stabilization assay (Table 4). T2 cells were incubated for 18 hours with the depicted synthetic p185$^{HER-2/neu}$ peptides. Cells were then washed and stained with antihuman HLA-A2 antibody (3%), a second step FITC-conjugated antibody (3%) was then added. The % increase of class I on cell surface as measured by increased fluorescent intensity of cells incubated with peptide compared to cells incubated in medium alone is indicated.

TABLE 4

| p185$^{HER-2/neu}$ Peptides | % Increase of class I stabilization on T2 |
|---|---|
| p 48–56 | 20% |
| p 789–797 | 20% |
| p 851–859 | 12% |
| p 1172–1180 | 10% |

After leukapheresis of a normal homozygous HLA-A2 individual, bulk cultures of lymphocytes (3×10$^7$) were incubated with peptide in a concentration of 10 µg peptide/ml. An individual homozygous for HLA-A2.1 was used on the presumption that a double dose of the MHC/peptide complex would allow more effective priming. Large numbers of lymphocytes were used to overcome the presumed low frequency of precursors. Generation of CD8+CTL responses has long been known to require concurrent stimulation of CD4+T cell responses to provide help/amplification. Both peptides used were chosen for class I MHC binding, and presumably could not stimulate CD4+ helper T cells. To provide T cell help, low concentrations (5 µg/ml) of tetanus toxoid were added to culture along with peptide. So as not to overwhelm or dominate the culture with the tetanus toxoid response, titrations of tetanus toxoid had previously been assessed in a standard proliferation assay with the donor's lymphocytes and the concentration of tetanus toxoid that provided the lowest detectable stimulation index was used.

Figure 4A:
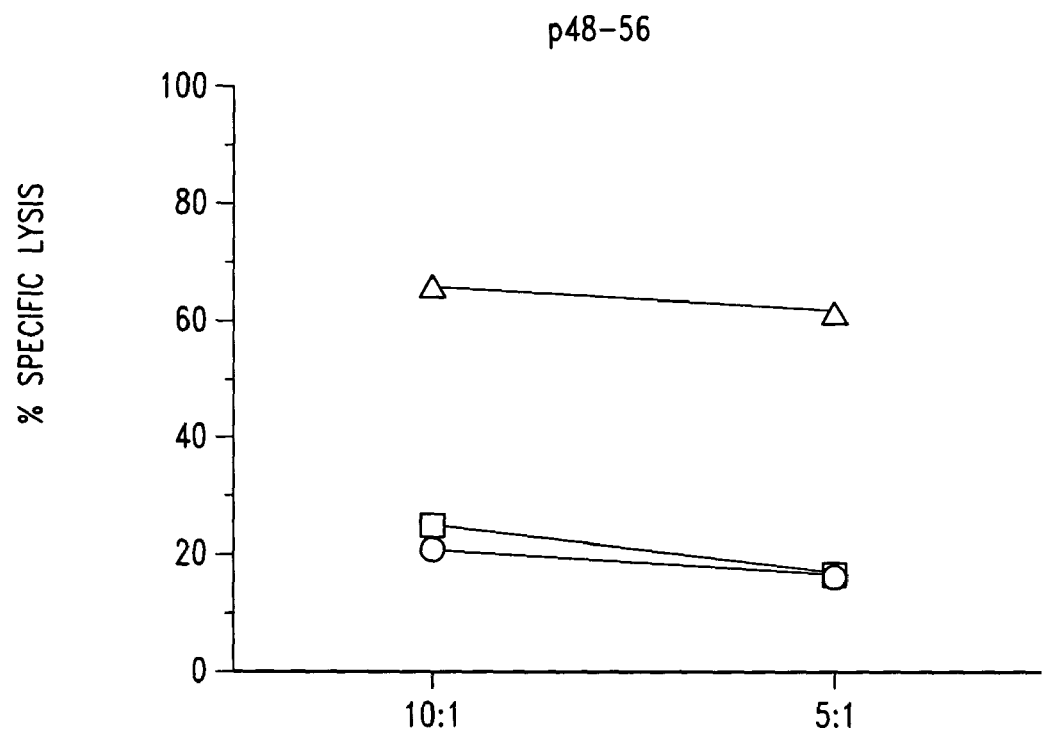
FIG. 4 (panels A and B) graphically illustrates that $CD8^+$ CTL specific for HER-2/neu peptides 48-56 and 789-797 can be generated by in vitro immunization. Three×$10^7$ PBMC from a homozygous HLA-A2 normal donor were incubated with p48-56 or $p789-797^{HER-2/neu}$ peptides at concentrations of 10 µg/ml. The lymphocytes were tested for lytic activity after 10 in vitro sensitizations (IVS). Data is depicted after the tenth IVS with p48-56 (panel A) or with p789-797 (panel B). Target cells consisted of $^{51}$Cr-labeled autologous EBV transformed B lymphocytes which had been incubated with p48-56 or $p789-797^{HER-2/neu}$ or an irrelevant peptide for 2 hours prior to use. A four hour chromium release assay (CRA) was performed. The results represent the percent specific lysis at the indicated effector: target (E:T) ratio. Target controls of $^{51}$Cr-labeled K562 and Daudi cells were also included to evaluate NK and LAK activity. The execution of the CRA is as described. The results represent the percent specific lysis at the indicated effector:target (E:T) ratio.
Figure 4B:
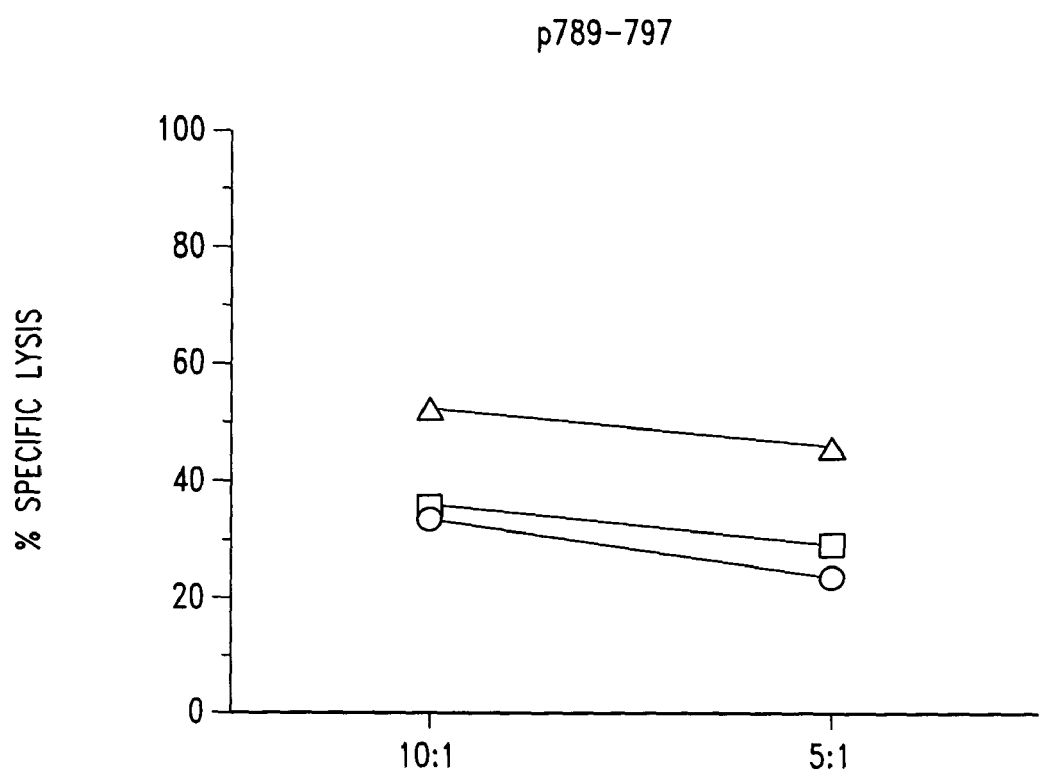

Low doses of IL-2 added late to culture were used to maintain lymphocyte proliferation. Within the present disclosure, standard conditions for expanding in vivo primed CTL following secondary sensitization in vitro usually have included IL-2 at 5-10 U/ml on day 2 of stimulation. Under primary in vitro immunization conditions, similar concentrations of IL-2 induced expansion of nonspecifically lytic NK and T cells, presumably due to the predominance of NK cells and AMLR responsive cells relative to peptide-specific CTL. For in vitro priming, the T cell culture received no IL-2 for the first 10 days, with only 1 unit/ml administered on day +2 after the second IVS. Thereafter, IL-2 at 2 U/ml could be administered on day +2 and day +4 of the 7 day stimulation cycle. T cells were stimulated with peptide on irradiated PBL as APC every 7 days. Evaluation for specific lytic function was performed after the fourth IVS and revealed specific lytic activity but substantial non-specific lytic NK and T cell activity. Routine $^{51}$Cr release assay performed after the tenth IVS (FIG. 4) revealed greater than 50% lysis for both bulk T cell lines. Lysis against control targets of K562 and Daudi was less than 2%.

Example 3

Antibodies Directed against HER-2/neu Protein can be Detected in the Sera of Patients with Breast Cancer A. Antibodies Directed Against p185(HER-2/neu) Protein and p105(HER-2/neu) Extracellular Domain were Detected in the Sera of Some Breast Cancer Patients The sera of 20 patients with breast cancer were analyzed. The 20 patients were participants from the Fred Hutchinson Cancer Research Center, Division of Epidemiology WISH study. The patient population consisted of women recently diagnosed with breast cancer, generally less than 3 months from surgery. Their age was less than 55 and their HER-2/neu tumor status was unknown. Anti-p185 antibody was found in 55% of the group as evidenced by bands corresponding to the positive control.

Figure 5:
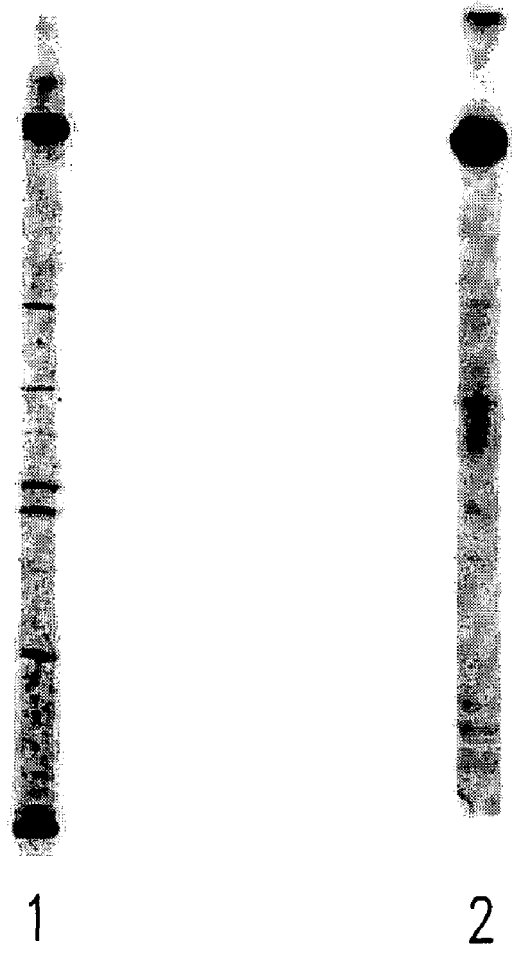
FIG. 5 pictorially illustrates that antibodies are detectable against $p185^{HER-2/neu}$ in the sera of a breast cancer patient. Lane 1 represents the immunoblot of p185 using a HER-2/neu positive breast cancer patient's sera (1:1000 dilution) as primary antibody. The blot was analyzed as described further below. Lane 2 represents the control strip from that experiment developed with c-neu antibody.

Antibody analysis was based on a modification of standard Western blotting techniques (Laemmli, *Nature* 227: 680-685, 1970; Burnett, *Anal. Biochem.* 112:195-203, 1981). A 7.5% SDS polyacrylamide gel was poured with a single 12 cm long comb in the stacking gel to create a "trough." Two immunoprecipitated SKBR3 membrane preparations, described above, were dissolved in loading buffer and layered across the trough. The gel was then run in standard fashion resulting in a band of equally distributed proteins across the gel. The protein was transferred to nitrocellulose (Amersham Hybond) for subsequent immunoblotting and development by chemiluminescence methods (Amersham ECL). Once protein transfer was complete, the nitrocellulose was cut lengthwise into 25 equal strips and placed in a 25 well incubation tray. The nitrocellulose strips were then blocked with Tris buffered saline and 1% bovine serum albumin (TBS BSA) for 1 hour. This allows for analysis of 23 patients with 2 control strips. Patient sera is used as primary antibody, and after blocking, the strips are incubated for 24 hours at 4° C. with sera diluted 1:200 and 1:400 in TBS BSA. The second antibody is a goat antihuman HRP conjugate which will interact with the chemiluminescent developing reagent (Amersham ECL) resulting in light emission which can be photographed. A control strip is developed with c-neu Ab3 antibody previously described in a similar fashion with this assay both IgA and IgG antibody specific for p185 were detected. Patient sera identified the same p185 band (FIG. 5) as did the known HER-2/neu-specific antibody, providing evidence that some patients have existent antibody immunity to HER-2/neu.

Figure 6:
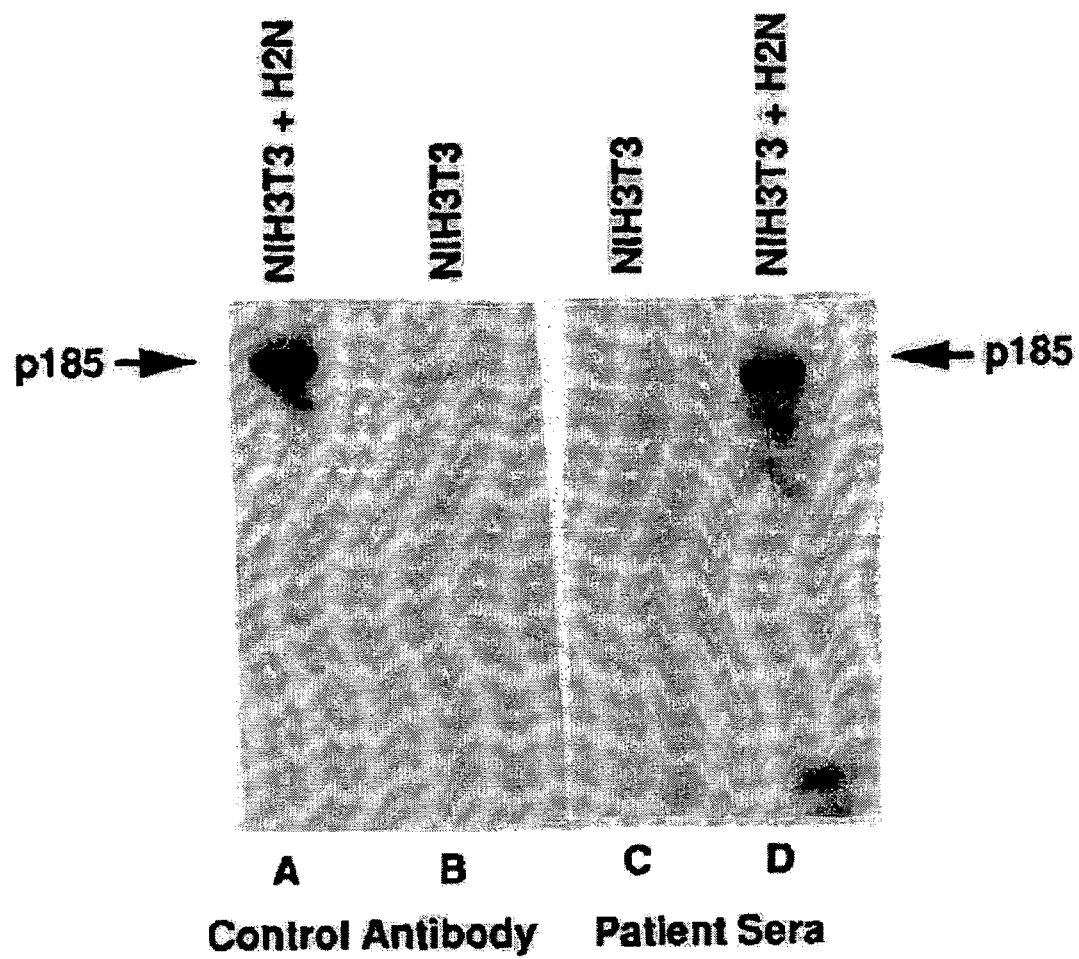
FIG. 6 pictorially shows that antibodies in the sera of a breast cancer patient identify the same p185 band as does a known HER-2/neu-specific antibody ("control antibody"). A membrane preparation from NIH3T3 cells (a murine cell line) that had been transfected with HER-2/neu cDNA ("NIH3T3+H2N") was tested against control antibody (lane A) or patient sera (lane D). Similarly, a membrane preparation from untransfected cells ("NIH3T3") was tested against control antibody (lane B) or patient sera (lane C).

To validate these responses patient sera was tested against a murine cell line (NIH 3T3) that had been transfected with HER-2/neu cDNA. As a negative control, untransfected cells were used. Membrane preparations were prepared from the two cell lines and patient sera was used as primary antibody as previously described. The patient sera identified the same p185 band as did the known HER-2/neu-specific antibody. That band was present in the cells that contained HER-2/neu, but undetectable in the cells that did not contain HER-2/neu (FIG. 6).

Figure 7:
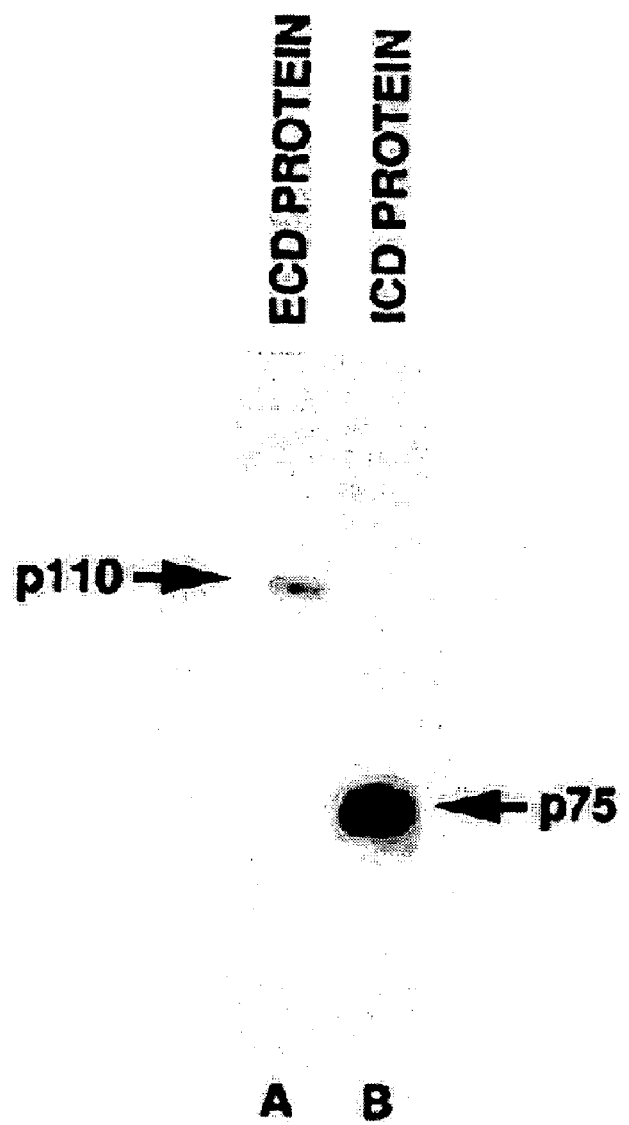
FIG. 7 pictorially illustrates that some breast cancer patients have antibodies directed to both the extracellular and intracellular domain of the HER-2/neu protein. Sera of breast cancer patients is tested against the extracellular domain ("ECD protein") or the intracellular domain ("ICD protein"), in lanes A and B, respectively.

Recombinant proteins of the extracellular and intracellular domain portions of HER-2/neu were obtained. The extracellular protein (110 kD) and intracellular protein (75 kD) were resolved on a 7.5% SDS-PAG gel and incubated with patient sera as primary antibody as previously described. The sera identified both proteins proving that some patients have antibodies directed to both the extracellular and intracellular domain of the HER-2/neu protein (FIG. 7).

B. Seven Normal Individuals Showed No Evidence of Antibody to HER-2/neu Protein

In studies to determine the extent to which detection of antibody to HER-2/neu is specific for malignancy, sera from seven normal individuals was obtained and analyzed in identical fashion as described above. There was no evidence of antibodies directed toward any HER-2/neu protein.

C. The Sera of Three Patients with Known HER-2/neu Positive Tumors Contained Antibodies Against p185 and p105

Sera from breast cancer patients whose HER-2/neu tumor status is known was collected and analyzed to determine the extent to which antibody to HER-2/neu correlates with the presence of HER-2/neu-positive tumors. Three patients with overexpression of p185$^{HER-2/neu}$ protein in their primary tumor were analyzed. Antibodies against p185 were detected in all three. The antibody detected in our studies was IgG. Immunoglobulin class switch from IgM to IgG or IgA require T cell help often directed against different epitopes on the same protein molecule.

Example 4

Peptide Based Vaccines Elicit Immunity to HER-2/neu

A. Materials and Methods
1. Animals
Rats used in this study were Fischer strain 344 (CDF (F-344)/CrlBR) (Charles River Laboratories, Portage Mich.). Animals were maintained at the University of Washington Animal facilities under specific pathogen free conditions and routinely used for experimental studies between 3 and 4 months of age.

2. Antigens

Nine peptides were constructed, derived from the amino acid sequence of the rat neu protein. The peptides, 15-18 amino acids in length, were highly homologous to the human HER-2/neu peptide sequence. These peptides were chosen based on an increased probability of interaction with human Class II MHC molecules. This theoretical potential was evaluated by the use of a protein sequence analysis package, TSites, that incorporates several computer algorithms designed to distinguish potential sites for T cell recognition (Feller and de la Cruz, Nature 349:720-721, 1991). Several peptides identified from the rat sequence were predicted to have potential for class II interaction with both human and murine MHC. Nine peptides were chosen for immunization of the rats (Table 5). Eight of the nine were in areas of 100% homology with human neu. The remaining peptide had greater than 80% homology with human neu (Yamamoto et al., Nature 319:230-234, 1986). The peptides were synthesized and purified by H. Zabrowski (University of Washington, Seattle, Wash.), then dissolved in phosphate-buffered saline (PBS), pH 7.4, to give 2 mg/ml stock solutions. Prior to aliquoting, peptides were sterile filtered, then stored at −70° C.

TABLE 5

Peptides from the Rat neu Protein for Immunization

| Rat Sequence | Amino Acids | Protein Domain | Homology to Human neu |
|---|---|---|---|
| p 45–59 | HLDMLRHLYQGCQVV (Seq. ID No. 30) | ECD | 100% |
| p 98–112 | PLQRLRIVRGTQLFE (Seq. ID No. 31) | ECD | 100% |
| p 323–337 | NQEVTAEDGTQRCEK (Seq. ID No. 56) | ECD | 100% |
| p 332–349 | TQRCEKCSKPCARVCYGL (Seq. ID No. 60) | ECD | 100% |
| p 433–447 | RIIRGRILHDGAYSL (Seq. ID No. 67) | ECD | 80% |
| p 781–795 | GVGSPYVSRLLGICL (Seq. ID No. 44) | ICD | 100% |
| p 788–802 | SRLLGICLTSTVQLV (Seq. ID No. 45) | ICD | 100% |
| p 932–946 | PAREIPDLLEKGERL (Seq. ID No. 49) | ICD | 100% |
| p 1171–1185 | TLERPKTLSPGKNGV (Seq. ID No. 54) | ICD | 100% |

ECD = extracellular domain
ICD = intracellular domain

3. Immunization

One group of rats was immunized with a mixture of extracellular domain (ECD) peptides and one group with a mixture of intracellular domain (ICD) peptides. The final group received adjuvant alone. Peptides were administered at a final concentration of 100 µg each in a total volume of 200 µl. The animals underwent 3 immunizations each 14-16 days apart with either CFA or IFA as adjuvant (Sigma ImmunoChemicals, St. Louis, Mo.). 16 days after the third immunization sera was obtained for assessment of immune response.

4. Cell Lines

Two cell lines were used as a source of neu proteins. SKBR3, a human breast cancer cell line that is a marked overexpressor of HER-2/neu (American Type Culture Collection, Rockville, Md.), was maintained in culture in 10% fetal bovine serum (FBS) (Gemini Bioproducts, Inc., Calabasas, Calif.) and RPMI. DHFR-G8, an NIH/3T3 cell line cotransfected with cneu-p and pSV2-DHFR (American Type Culture Collection, Rockville, Md.), was used as a source of non-transforming rat neu protein (Bernards et al., Proc. Natl. Acad. Sci. USA 84:6854-6858, 1987). This cell line was maintained in 10% FBS and Dulbecco's modified Eagle's medium with 4.5 g/L glucose. DHFR-G8 cells were passaged through the same medium supplemented with 0.3 µM methotrexate at every third passage to maintain the neu transfectant.

5. Preparation of Cell Lysates

Lysates of both SKBR3 and DHFR-G8 were prepared and used as a source of protein for both ELISA and immuno-precipitation studies. Briefly, a lysis buffer consisting of tris base, sodium chloride and Triton-X (1%) pH 7.5 was prepared. Protease inhibitors were added; aprotinin (1 µg/ml), benzamidine (1 mM) and PMSF (1 mM). 1 ml of the lysis buffer was used to suspend $10^7$ cells. The cells were vortexed for 15 seconds every 10 minutes for an hour until disrupted. All procedures were performed on ice in a 4° C. cold room. After disruption the cells were microfuged at 4° C. for 20 minutes. Supernatant was removed from cell debris and stored in small aliquots at −70° C. until used. Presence of human and rat neu in the lysates was documented by Western blot analysis.

6. ELISA for Rat Antibody Responses 96 well Immulon 4 plates (Baxter SP, Redmond, Wash.: Dynatech Laboratories) were incubated overnight at 4° C. with an IgG2a murine monoclonal antibody directed against rat neu (kindly provided by Dr. M. Green) at a concentration of 10 µg antibody per ml. After incubation, all wells were blocked with PBS and 1% bovine serum albumin (BSA) (Sigma Chemical Co., St. Louis, Mo.), 100 µl/well for 4 hours at room temperature. The plate was washed with PBS/0.5% Tween and protein was added. Rows of wells were coated with alternating PBS/1% BSA and DHFR-G8 lysate ($10^8$ cells/20 ml PBS), 50 µl/well, overnight at 4° C. After washing, the plate was incubated with rat sera at the following dilutions: 1:25, 1:50, 1:100, 1:200. The sera was diluted in PBS/1% BSA/1% FBS/25 µg/ml mouse IgG/0.01% $NaN_3$ and then serially into PBS/1% BSA. 50 µl of diluted sera was added/well and incubated 1 hour at room temperature. Sheep anti-rat Ig horseradish peroxidase (HRP) was added to the wells at a 1:7,500 dilution in PBS/1% BSA and incubated for 45 minutes at room temperature (Amersham Co., Arlington Heights, Ill.). Isotype assays were performed similarly with rabbit anti-rat IgG and sheep anti-rat IgM HRP antibodies as the second step antibody at a concentration of 1:5000 (Serotec Ltd., Oxford, England). Control wells consisting of varying dilutions of c-neu-Ab-1, a rabbit polyclonal antibody directed against the kinase portion of human neu which also has reactivity to rat neu (Oncogene Science, Uniondale, N.Y.), were used as a positive control. These wells received a second step antibody of goat-anti rabbit HRP at a 1:5000 dilution (Amersham Co.). Following the final wash, TMB (Kirkegaard and Perry Laboratories, Gaithersburg, Md.) developing reagent was added. Color reaction was read at an optical density of 640 nm until the positive control wells reached 0.3 OD. The reaction was stopped with 1N HCl and the optical density was read at 450 nm. The OD of each serum dilution was calculated as the OD of the neu coated wells minus the OD of the PBS/1% BSA coated wells. A pool of 5 normal rat sera was run on each plate as a negative control.

7. Immunoprecipitation

Experimental rat sera was used to immunoprecipitate human neu from the SKBR3 cell line and rat neu from the DHFR-G8 cell line. A commercially prepared IgG1 mouse monoclonal antibody, c-neu-Ab-3, which cross reacts with both human and rat neu, was used as the positive control antibody in the immunoprecipitation (Oncogene Science). Sera from 5 pooled normal rats and 2 rats immunized with adjuvant alone and no peptide antigens were used as 2 negative controls. 1 ml of DHFR-G8 or SKBR3 lysate was incubated with 75 μl of rat sera or 10 μl (1 μg) of neu specific monoclonal antibody and 15 μl of protein A+G (Oncogene Science). The solution was rocked gently overnight at 4° C. After this incubation, the agarose was pelleted and washed twice in a tris HCl/EDTA buffer (1M Tris HCl pH 7.5, 0.25 M EDTA, and 5M NaCl), then twice in the same buffer with NP-40 added to a 0.5% concentration. The immunoprecipitates were analyzed by Western blot as described above using c-neu-Ab-1 (Oncogene Science) as the primary antibody. This antibody is a neu specific polyclonal rabbit antibody which cross reacts with both human and rat neu.

8. ELISA for Peptide Epitope Analysis 96 well Immulon 4 plates (Dynatech Laboratories) were incubated overnight at 4° C. with peptides at a concentration of 10 μg/well diluted in PBS alternating with rows of PBS/1% BSA. After incubation, all wells were blocked with PBS/1% BSA, 100 μl/well for 4 hours at room temperature. The plate was washed with PBS/0.5% Tween. After washing, the plate was incubated with rat sera at the following dilutions: 1:50 and 1:100. The sera was diluted in PBS/1% BSA/1% FBS/25 μg/ml mouse IgG/0.01% NaN$_3$ and then serially into PBS/1% BSA. 50 μl of diluted sera was added/well and incubated 1 hour at room temperature. Sheep anti-rat HRP was added to the wells at a 1:7,500 dilution in PBS/1% BSA and incubated for 45 minutes at room temperature. Following the final wash, the TMB developing reagent was added. Color reaction was read at an optical density of 640 nm until the reading on the most reactive well reached 0.3 OD. The reaction was stopped with 1N HCl and the optical density was read at 450 nm. The OD of each serum dilution was calculated as the OD of the peptide coated wells minus the OD of the PBS/1% BSA coated wells. A pool of 5 normal rat sera was run with each peptide at the same dilutions as the experimental sera as a negative control.

9. Western Blot Analysis for Rat Antibody Responses

Immunoprecipitates of SKBR3 and DHFR-G8 were used as a source of human and rat neu proteins in the Western assays. Recombinant human ECD and ICD (kindly provided by Drs. B. Groner and N. Lydon) were used to evaluate antibody responses to the neu domains. 7.5% polyacrylamide gels were electrophoresed in the Pharmacia Phast System (Pharmacia LKB Biotechnology AB, Uppsala, Sweden). After transfer to nitrocellulose (Hybond-C, Amersham Co.) the neu proteins were identified by immunoblot in a similar manner. All control blots were developed by using the IgG1 mouse monoclonal primary antibody, c-neu-Ab-3 (Oncogene Science). This antibody cross reacts with both rat and human neu. The primary antibody was used in a 1:1000 dilution with tris-buffered saline/1% BSA/0.1% Nonidet P-40. A polyclonal rabbit antimouse HRP-conjugated second antibody (Amersham Co.) was used in a 1:10,000 dilution. The blot was then developed using a chemiluminescent reaction (Amersham ECL). Identically run experimental blots were analyzed with rat sera as primary antibody. The sera were used in a 1:500 dilution with tris-buffered saline/1% BSA/0.1% Nonidet P-40 in an overnight incubation with the blot a 4° C. Secondary antibody, goat-anti rat HRP conjugate (Amersham Co.) was used at a 1:5000 dilution. The blots were developed with ECL detection reagents and exposed to Hyperfilm-ECL (Amersham Co.). The film was developed and examined for reaction to human and rat neu as well as the ICD and ECD domains of the protein. Sera from 5 pooled normal rats and 2 rats immunized with adjuvant alone and no peptide antigens were used as 2 negative controls.

10. T Cell Proliferation Assays

For analysis of neu peptide specific responses: Fresh spleen or lymph node cells were harvested by mechanical disruption and passage through wire mesh and washed. $2 \times 10^5$ spleen cells/well and $1 \times 10^5$ lymph node cells/well were plated into 96-well round bottom microtiter plates (Corning, Corning, N.Y.) with 6 replicates per experimental group. The media used consisted of EHAA 120 (Biofluids) with L-glutamine, penicillin/streptomycin, 2-mercaptoethanol, and 5% FBS. Cells were incubated with 25 μg/ml of the various peptides. The group incubated with the peptide mix received 25 μg of each of the peptides. After 4 days, wells were pulsed with 1 μCi of [$^3$H]thymidine for 6-8 hours and counted. Data is expressed as a stimulation index (SI) which is defined as the mean of the experimental wells divided by the mean of the control wells (no antigen). For analysis of neu protein specific responses: Spleen or lymph node cells were cultured for 3 in vitro stimulations. At the time of analysis $1 \times 10^5$ cultured spleen or lymph node T cells were plated into 96 well microtiter plates as described above. Cells were incubated with 1 μg/ml immunoaffinity column purified rat neu (from DHFR-G8 cells as the source of rat neu). After 4 days, wells were pulsed with 1 μCi of [$^3$H] thymidine for 6-8 hours and counted. Data is expressed as a stimulation index which is defined as the mean of the experimental wells divided by the mean of the control wells (no antigen).

11. Rat T Cell Culture

Spleen and lymph nodes from immunized rats were harvested into single cell suspensions. PBMC were isolated by Ficoll/Hypaque density gradient centrifugation (Histopaque-1083, Sigma Diagnostics, St. Louis, Mo.). Cells were washed and resuspended in bulk culture of $3 \times 10^7$ cells in 6 well plates. The media used consisted of EHAA 120 (Biofluids) with L-glutamine, penicillin/streptomycin, 2-mercaptoethanol, and 10% FBS. A mix of the immunizing peptides were added directly to culture at a concentration of 10 μg/ml of each peptide. The cultures were restimulated on the peptide mix every 14 days with syngeneic spleen that had been preincubated with the peptide mix for 2 hours, irradiated to 1000 rads, and then washed. Stimulator to effector ratio was 1:1 in each culture. After the second week in culture, media was supplemented with 50% Con A conditioned media. At the end of 3 in vitro stimulations, cells were >98% CD3+.

Figure 8:
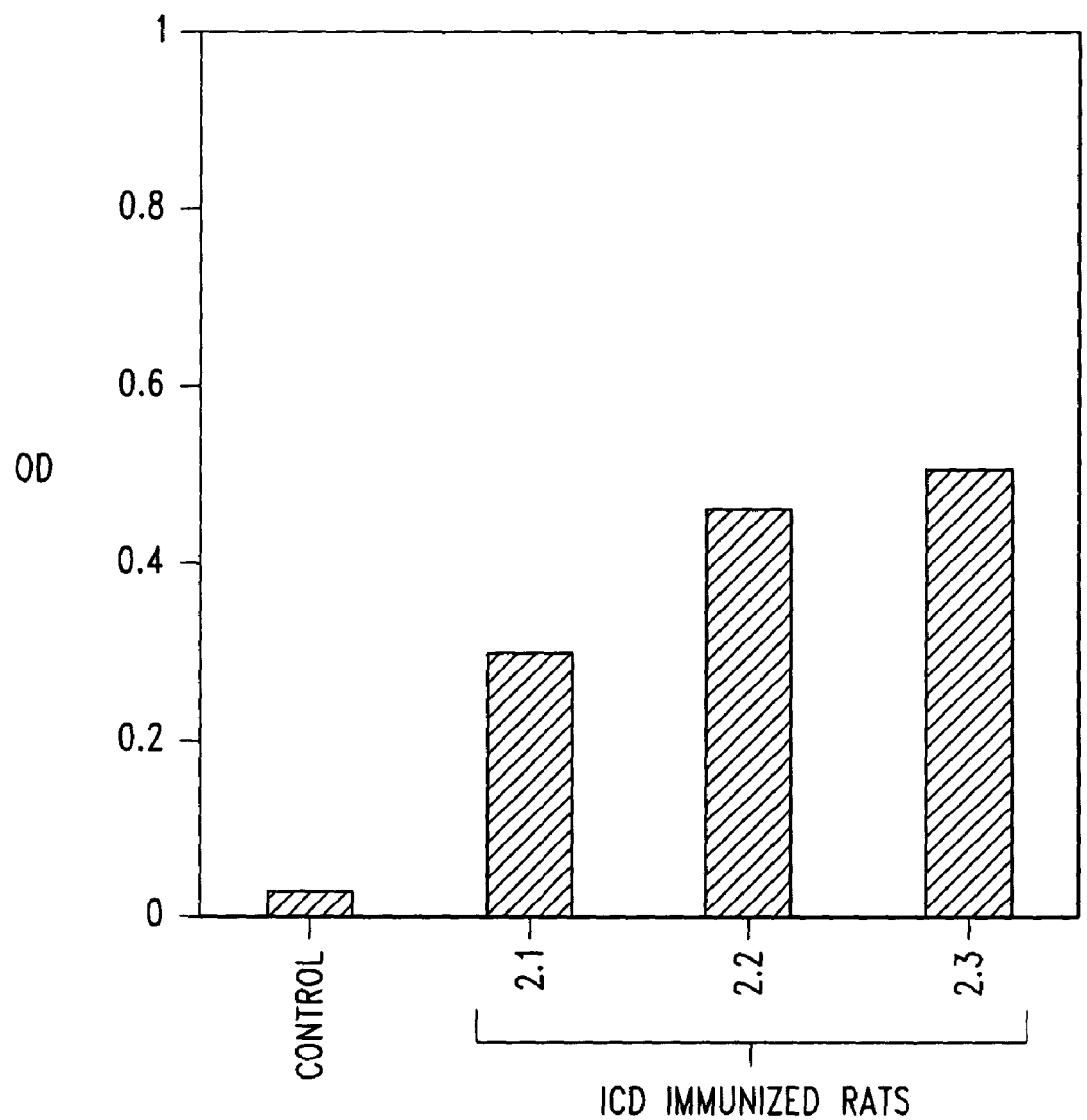
FIG. 8 graphically illustrates that rats immunized with peptides derived from the intracellular domain (ICD) portion of rat neu protein develop antibody responses to neu protein. An ELISA was performed to evaluate peptide immunized animals for antibody responses to non-transforming rat neu protein. Each sera was analyzed at a 1:25, 1:50, 1:100, and 1:200 dilution. The OD value shown is that of the background wells subtracted from the wells coated with neu protein. All data shown is at a rat sera concentration of 1:25. Control sera was derived from an animal immunized with adjuvant alone. Antibody responses titered with decreasing serum concentrations. Results were reproducible in 3 separately run assays.

B. Rats Immunized with Peptides Derived from the ICD Portion of Rat Neu Protein Develop Antibody Responses to Neu Protein Rats were immunized with mixtures of either 4 ICD peptides or 5 ECD peptides. Following the third immunization, serum and T cells from immunized rats were assessed for immunity to neu peptides and protein. Initial experiments assessed rats immunized with ICD peptides for antibody responses to whole neu protein. Serum antibody responses were analyzed by ELISA (FIG. 8). The results demonstrate that immunization to ICD peptides elicited antibody to whole neu protein. Sera was analyzed at 1:25, 1:50, 1:100, and 1:200 dilution. Results at the 1:25 dilution are depicted (FIG. 8). Neu specific antibody responses titered rapidly and at a 1:200 dilution the experimental sera demonstrated the same level of response as control. Isotype analysis revealed that the antibody responses were predominantly IgG (data not shown).

Figure 9:
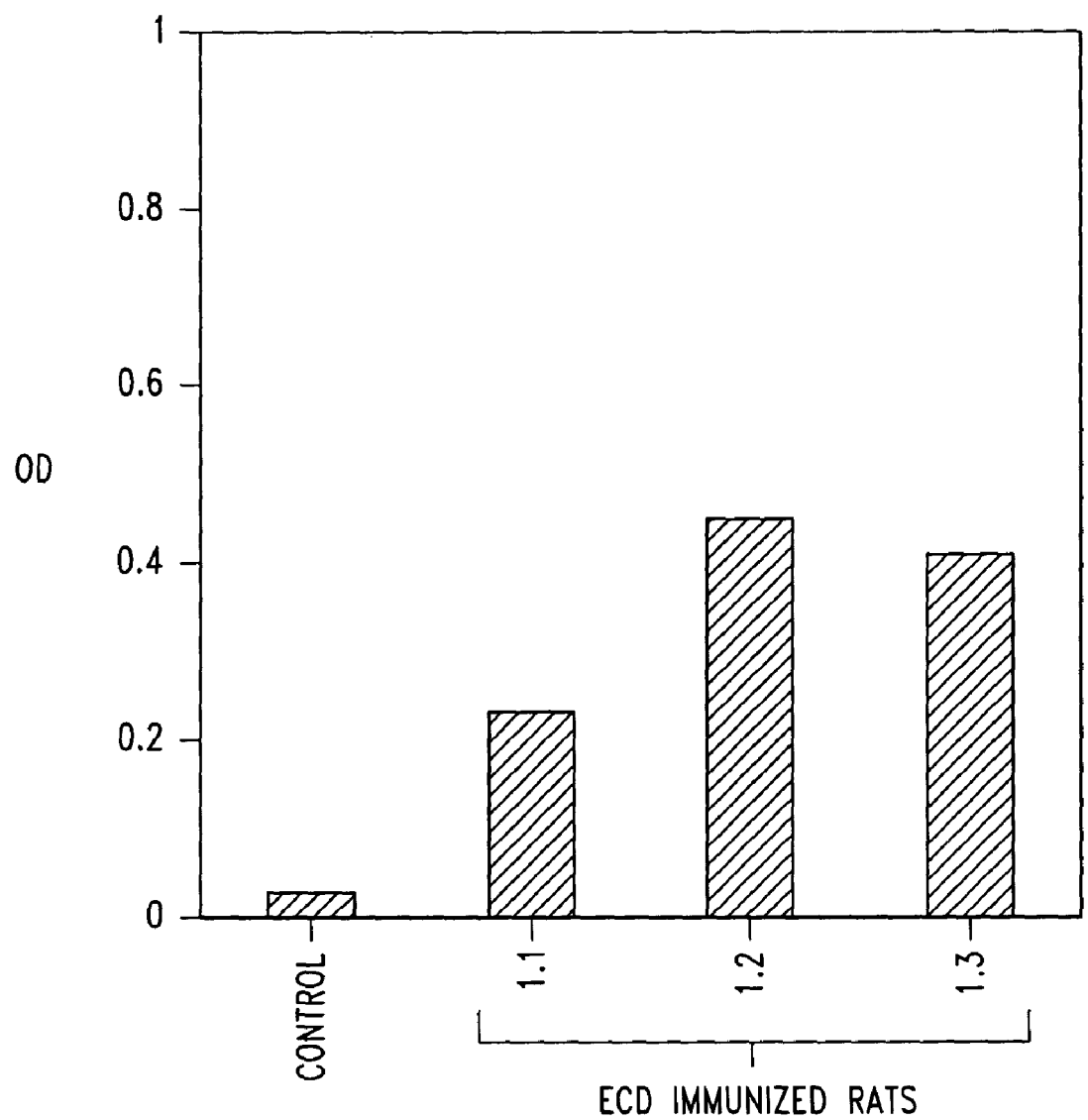
FIG. 9 graphically illustrates that rats immunized with peptides derived from the extracellular domain (ECD) portion of rat neu protein develop antibody responses to neu protein. ELISA evaluation was performed as described in FIG. 8. All data shown is at a rat sera concentration of 1:25. Control sera was derived from an animal immunized with adjuvant alone. Antibody responses titered with decreasing serum concentrations. Results were reproducible in 3 separately run assays.

C. Rats Immunized with Peptides Derived from the ECD Portion of Rat Neu Protein Develop Antibody Responses to Neu Protein Immunizations with ECD peptides were performed in an identical fashion as with ICD peptides. ELISA performed on sera from rats immunized with ECD peptides revealed the generation of antibody responses to whole neu protein (FIG. 9). The responses were equivalent to responses elicited by immunization with ICD peptides. These responses were predominantly of the IgG subtype (data not shown).

Figure 10A:
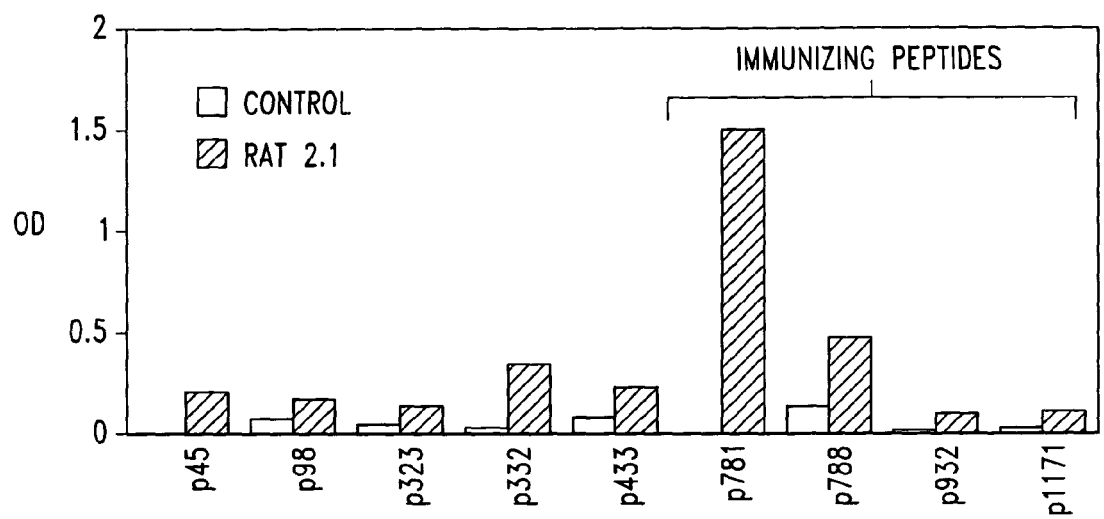
FIG. 10 graphically shows that epitope analysis of ICD antibody responses demonstrates dominant B cell epitopes as well as "determinant spreading" between domains. ELISA analysis for peptide epitopes was performed. Each animal's sera was evaluated at dilutions of 1:25, 1:50, 1:100, and 1:200 for each peptide analyzed. Antibody responses titered with decreasing serum concentrations. All data shown is at a rat sera concentration of 1:50. Control sera analyzed was pooled sera from 5 non-immunized animals. Results were reproducible in 3 separately run assays.
Figure 10B:
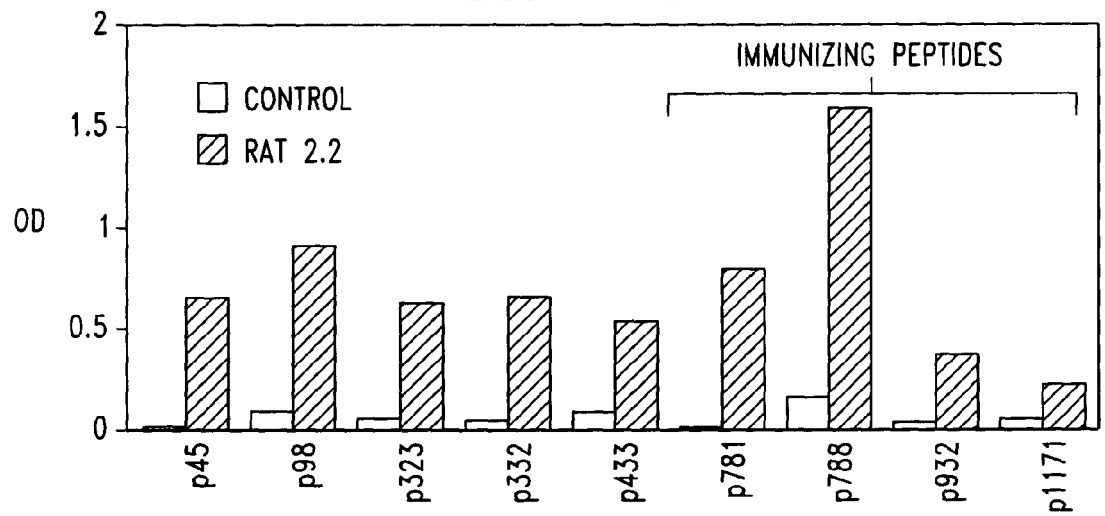
Figure 10C:
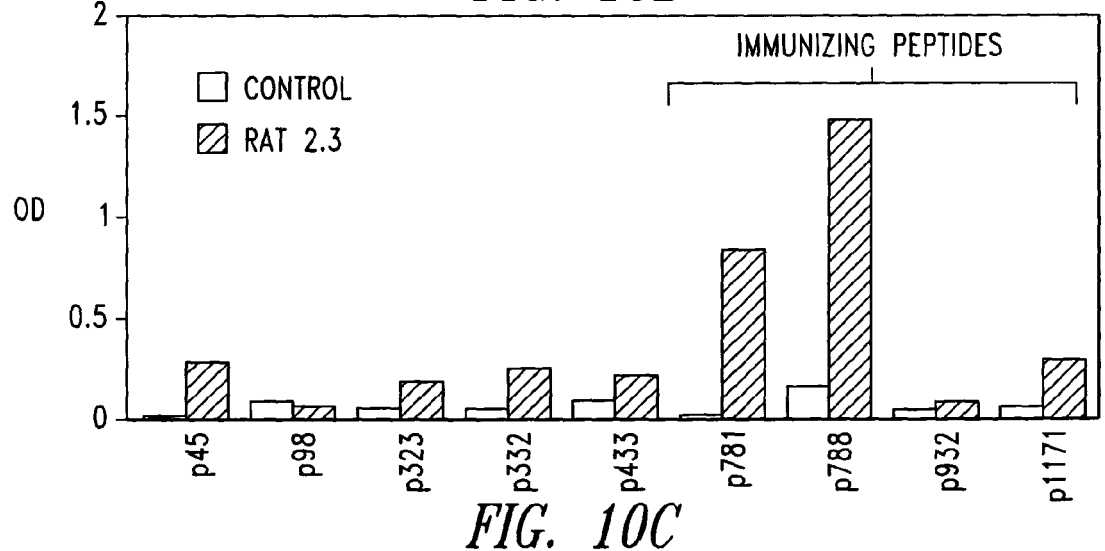

D. Epitope Analysis of ICD Antibody Responses Demonstrates Dominant B Cell Epitopes as well as "Determinant Spreading" Between Domains Mixtures of peptides had been used above for immunization. To determine which peptides in the mixture were the predominant B cell epitopes, sera from rats immunized with ICD peptides was analyzed by ELISA for responses to individual peptides. Responses to both ICD and ECD peptides were evaluated with the presumption that responses to the ECD peptides would be non-existent. Results (FIG. 10) revealed different responses in each rat. All rats had marked antibody responses to the overlapping p781 and p788 ICD peptides, although the relative levels of responses varied between animals. Responses to p932 and p1171 were observed, but were relatively weak. Surprisingly, rats immunized to the mixture of ICD peptides displayed significant antibody responses to ECD peptides. Responses in individual rats varied. Rat 2.2 had substantial responses to all five ECD peptides evaluated. Rats 2.1 and 2.3 had weaker responses. Thus, immunization to ICD peptides elicited antibody responses to ICD peptides as well as "determinant spreading" with the generation of antibody responses to the ECD portion of the molecule. Rats immunized with adjuvant alone did not develop T cell responses to any tested peptide.

Figure 11A:
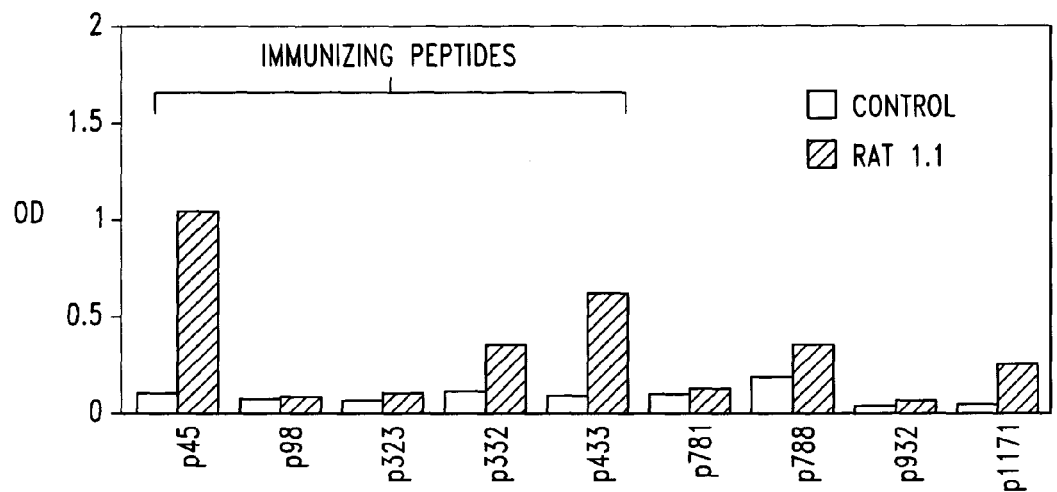
FIG. 11 graphically shows that epitope analysis of ECD antibody responses demonstrates dominant B cell epitopes. ELISA analysis for peptide epitopes was performed. Each animal's sera was evaluated at dilutions of 1:25, 1:50, 1:100, and 1:200 for each peptide analyzed. Antibody responses titered with decreasing serum concentrations. All data shown is at a rat sera concentration of 1:50. Control sera analyzed was pooled sera from 5 non-immunized animals. Results were reproducible in 3 separately run assays.
Figure 11B:
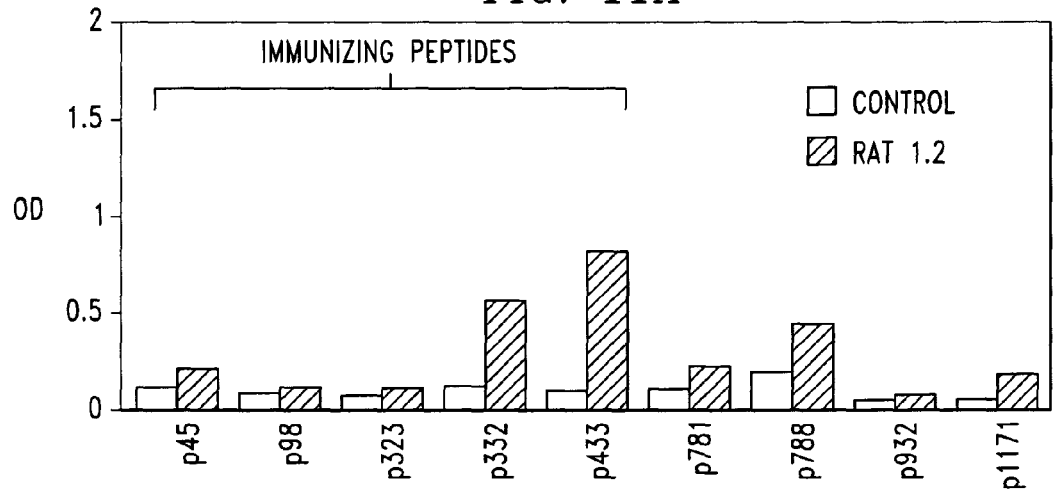
Figure 11C:
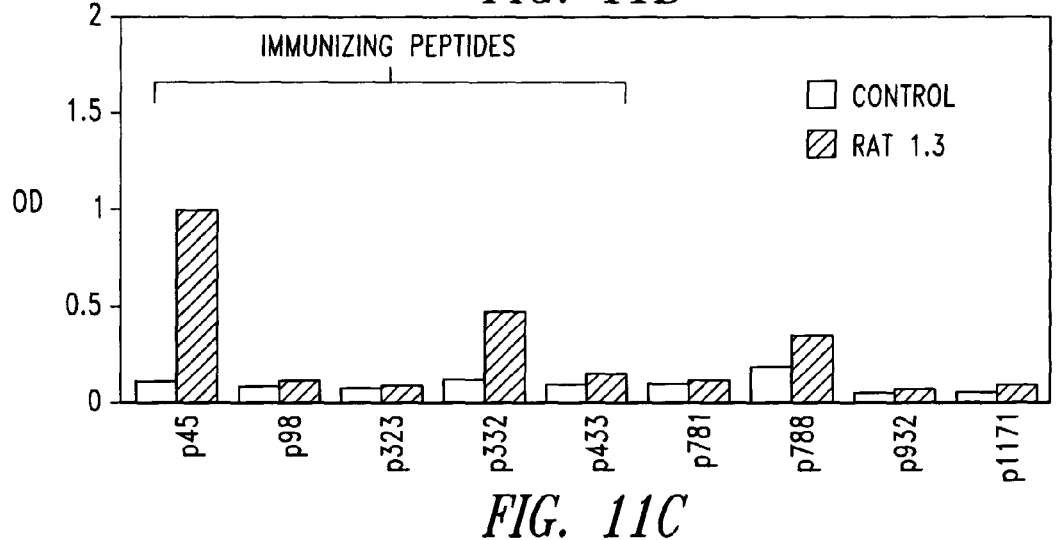

E. Epitope Analysis of ECD Antibody Responses Demonstrates Dominant B Cell Epitopes Determination of the dominant B cell epitopes in ECD peptide immunized animals was performed in an identical fashion. Again, the relative responses to individual peptides differed between each animal. Rats immunized with ECD peptides developed substantial responses to p45, p332, and p433 and minimal responses to p98 and p323 (FIG. 11). The dominant epitope was p45 in rats 1.1 and 1.3, but was p433 in rat 1.2. As with immunization to ECD peptides, determinant spreading was observed. All rats developed antibody to p788 in the ICD and rats 1.1 and 1.2 responded to p1171. The magnitude and extent of "determinant spreading" appeared to be less in the animals immunized with the ECD peptides than those immunized with the ICD peptides. However, only a limited number of potential epitopes were examined.

Figure 12:
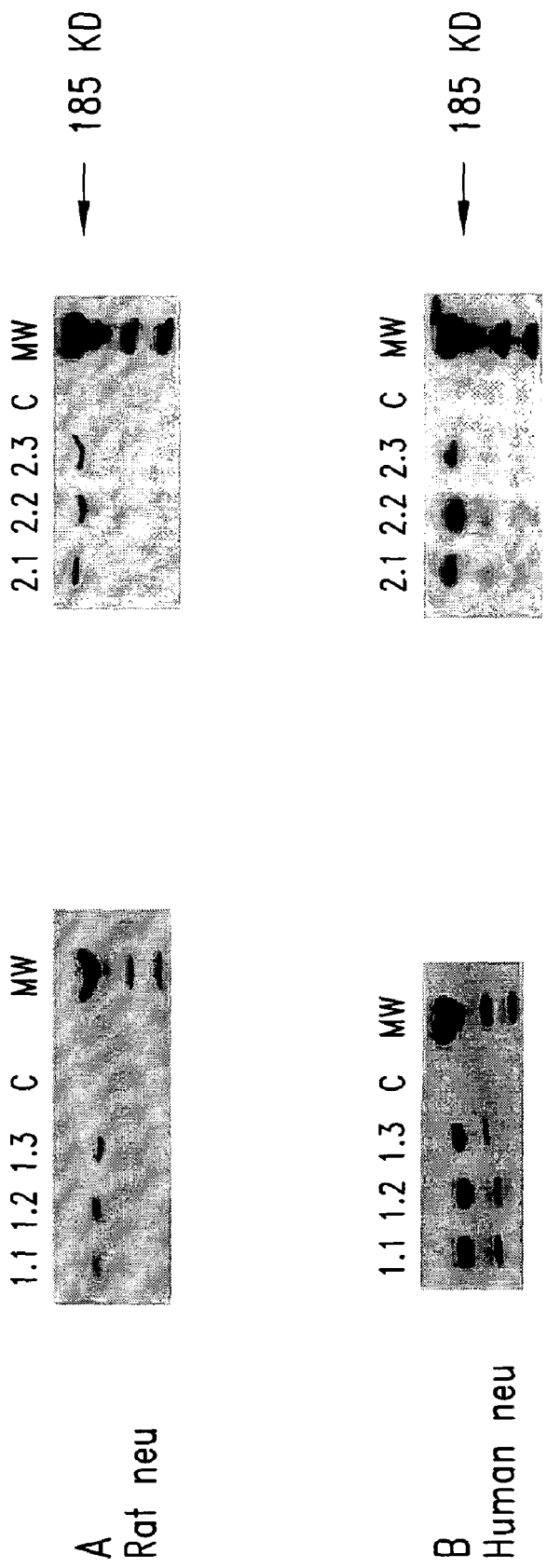
FIG. 12 pictorially illustrates that antibodies elicited by immunization to either ICD or ECD peptides are specific for and can immunoprecipitate both rat neu protein and human HER-2/neu protein. Panel A shows the results of an immunoprecipitation experiment with immunized rat sera and lysates of DHFRG-8. Each sera was able to immunoprecipitate rat neu from the cell lysates. The immunoprecipitates were resolved on a 7.5% SDS-acrylamide gel and transferred to nitrocellulose. The blots were probed with primary antibody, c-neu-Ab-3, at a 1:1000 dilution. Control sera of an animal immunized with the adjuvant alone showed no evidence of reactivity to rat neu. Panel B depicts the results of an immunoprecipitation experiment with immunized rat sera and lysates of SKBR3, a source of human neu. Immunoblotting was performed in an identical manner and all experimental animal sera were able to immunoprecipitate human neu. The control sera, again, showed no evidence of reactivity.

F. Antibodies Elicited by Immunization to either ICD or ECD Peptides are Specific for and can Immunoprecipitate Both Rat Neu Protein and Human HER-2/neu Protein The above experiments showed that immunization to neu peptides could elicit antibody responses to whole rat protein and peptides, as determined by ELISA. Verification of the antibody responses to protein observed by ELISA was performed by assessing the ability of immune sera to immunoprecipitate rat neu protein from lysates of DHFRG-8, an NIH-3T3 cell line transfected with non-transforming rat neu. Results showed that sera from rats immunized with either ECD or ICD peptides could immunoprecipitate rat neu (FIG. 12, Panel A).

The immunizing rat neu peptides were homologous with the human HER-2/neu protein sequence. Thus, the anti-peptide antibodies elicited should be reactive to both rat and human peptides. To determine whether the antibodies elicited were also specific for human HER-2/neu protein, experiments evaluated the ability of sera from peptide immunized rats to immunoprecipitate HER-2/neu from lysates of SKBR3, a human breast cancer cell line that overexpresses HER-2/neu. Sera from all rats immunized with ICD or ECD peptides could immunoprecipitate HER-2/neu protein while the control sera did not (FIG. 12, Panel B).

Figure 13:
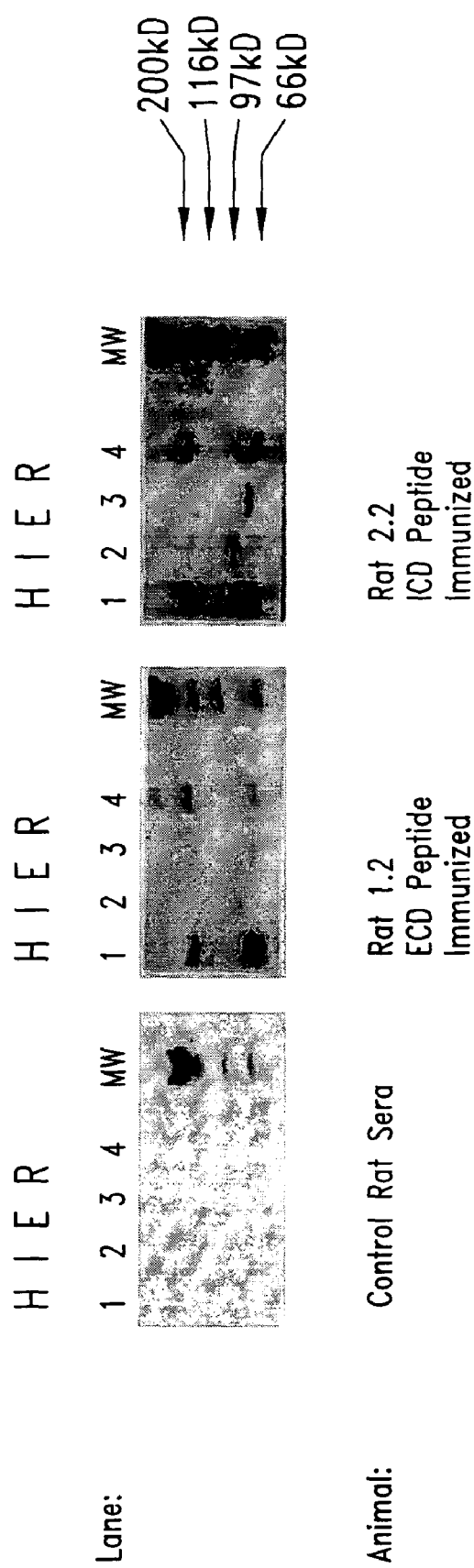
FIG. 13 pictorially illustrates that B cell epitopes that are cross reactive between human and rat neu are present in both domains of the protein. Shown here are the results of Western blot analysis of protein domain epitope mapping from representative animals in each immunized group. Animal 1.2 was immunized with the ECD group of peptides, animal 2.2 with the ICD group of peptides, and the control animal was immunized with adjuvant alone. Proteins were electrophoresed. After transfer to nitrocellulose the blots were incubated for 18 hours in rat sera at a 1:500 dilution. Antibody responses were detected with a second step goat anti-rat Ig HRP antibody at a dilution of 1:5000. Responses were detected to both human and rat neu as well as to both human ICD and ECD domain recombinant proteins. Antibody responses to these proteins could not be detected in the control animal which was immunized with adjuvant alone. Although data are shown here for animals 1.2, 2.2, and control, all animals in each group had the same pattern of response.

G. B cell Epitopes that are Cross Reactive Between Human and Rat Neu are Present in Both Domains of the Protein Antibody elicited by immunization to ICD and ECD peptides immunoprecipitated both rat and human neu protein. To further evaluate the protein domains recognized, sera from rats immunized with ICD and ECD peptides was evaluated by Western analysis for reactivity against human recombinant ECD and ICD as well as whole human and rat neu immunoprecipitated protein. Sera from animals immunized with either ICD or ECD peptides recognized both domains and whole protein from both species (FIG. 13). Control animals had no evidence of antibodies directed against either domain. These results verify not only the phenomenon of "determinant spreading" suggested in the peptide epitope analysis, but also demonstrate human and rat cross reactive epitopes in both domains.

Figure 14A:
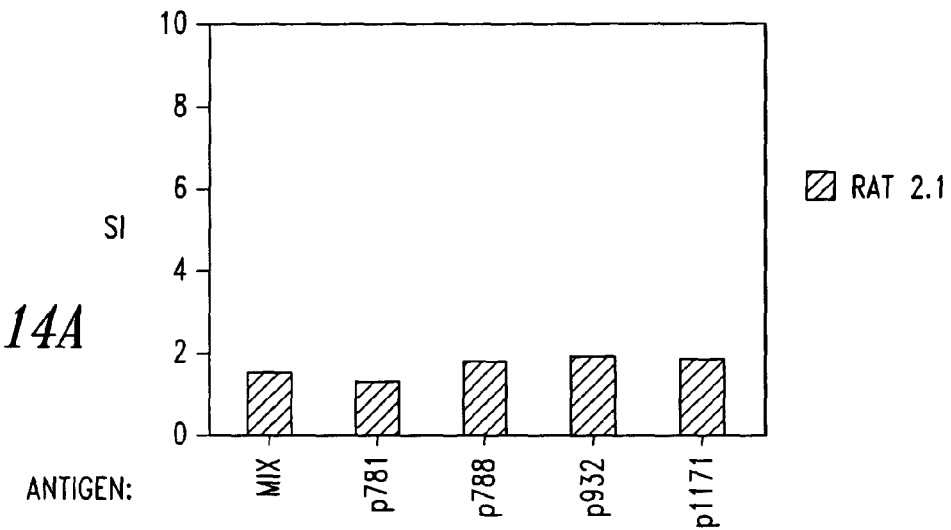
FIG. 14 graphically illustrates that immunization of rats with ICD peptides elicits neu peptide-specific T cell responses. $2\times10^5$ immunized spleen cells were incubated with 25 µg/ml of the various peptides. The "Mix" group consisted of 25 µg/ml each of the immunizing peptides. A proliferation assay was performed. Each experimental group was done in 6 well replicates. The data is expressed in terms of a stimulation index (SI) which is the mean of the experimental wells divided by the mean of the control (no antigen) wells. Stimulation indices greater than 2 are considered to be indicative of a primed response. Animals immunized with adjuvant alone showed no stimulation index greater than 0.9 to any of the tested peptides (data not shown).
Figure 14B:
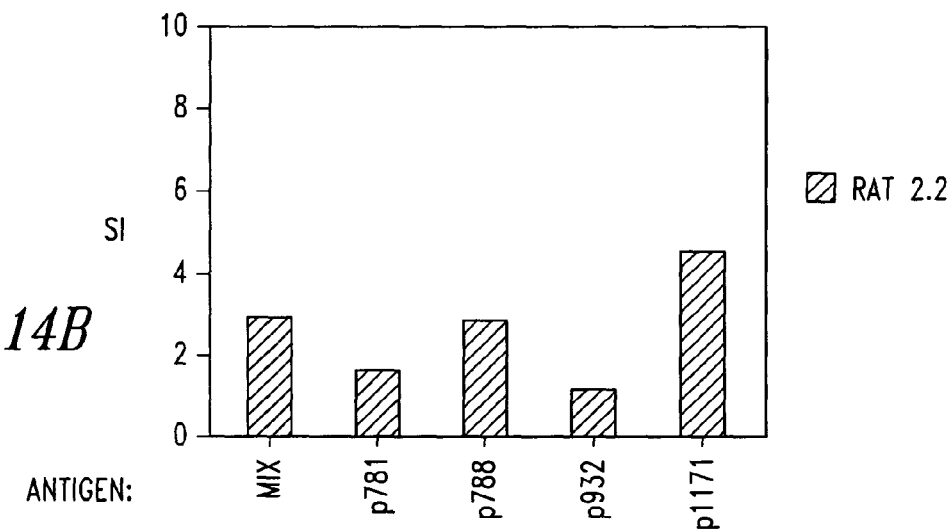
Figure 14C:
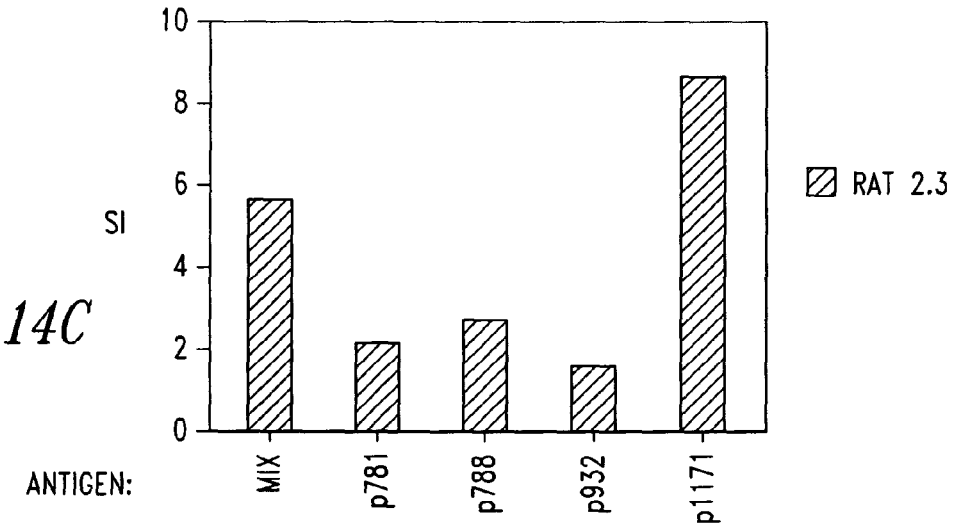

H. Immunization of Rats With ICD Peptides Elicits Neu Peptide-Specific T Cell Responses The above-detected antibody responses were IgG implying that T cell help was present and operative in immunoglobulin class switch. Spleen and lymph nodes cells were evaluated for proliferative responses to the immunizing peptides. Proliferative T cell responses to the immunizing peptides were observed, but the relative responses between individual rats were varied (FIG. 14). A stimulation index of >2 was arbitrarily chosen as the cut off of significance. Rat 2.1 did not have any proliferative response greater than SI of 2 to the mixture of immunizing ICD peptides or to individual peptides. Rats 2.2 and 2.3 had SI>2 to the mixture of ICD peptides with the dominant response to p1171 in both rats.

Figure 15:
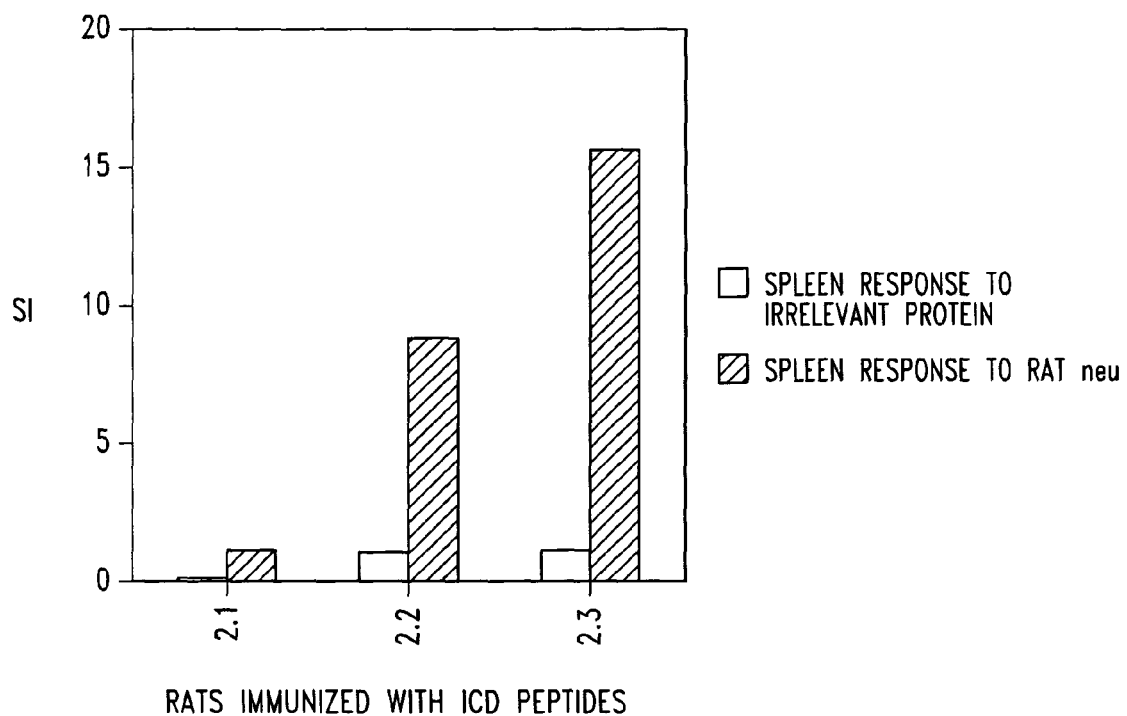
FIG. 15 graphically illustrates that immunization of rats with ICD peptides elicits neu protein-specific T cell responses. $1\times10^5$ cultured T cells derived from immunized spleen were incubated with $1\times10^5$ syngeneic spleen as APC (antigen presenting cells) and 1 µg/ml of purified rat neu protein. Each experimental group was done in 6 well replicates. The data is expressed in terms of a stimulation index which is the mean of the experimental wells divided by the mean of the control (no antigen) wells. Stimulation indices greater than 2 are considered to be indicative of a primed response. Wild type ras protein was the irrelevant protein used in the assay.

I. Immunization of Rats With ICD Peptides Elicits Neu Protein-Specific T Cell Responses Peptide specific T cell lines were derived by repeated in vitro stimulation of spleen cells from peptide immunized mice by a mixture of the immunizing peptides. After 40 days the cultured cells were greater than 98% CD3+. The cultured T cells from 2 of the 3 immunized rats demonstrated substantial responses to protein with SIs of 9 and 16 (FIG. 15). The SI from the third rat was >2. No responses to control protein were observed.

Figure 16A:
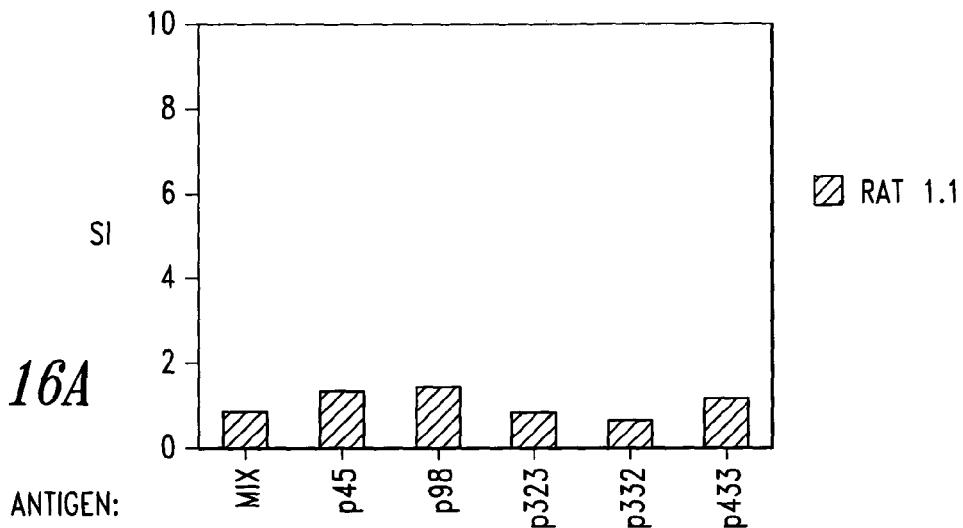
FIG. 16 graphically shows that immunization of rats with ECD peptides elicits only weak peptide-specific T cell responses. $2\times10^5$ immunized spleen cells were incubated with 25 µg/ml of the various peptides. The "Mix" group consisted of 25 µg/ml each of the immunizing peptides. Each experimental group was done in 6 well replicates. The data is expressed in terms of a stimulation index which is the mean of the experimental wells divided by the mean of the control (no antigen) wells. Stimulation indices greater than 2 are considered to be indicative of a primed response. Animals immunized with adjuvant alone showed no stimulation index greater than 1.0 to any of the tested peptides (data not shown).
Figure 16B:
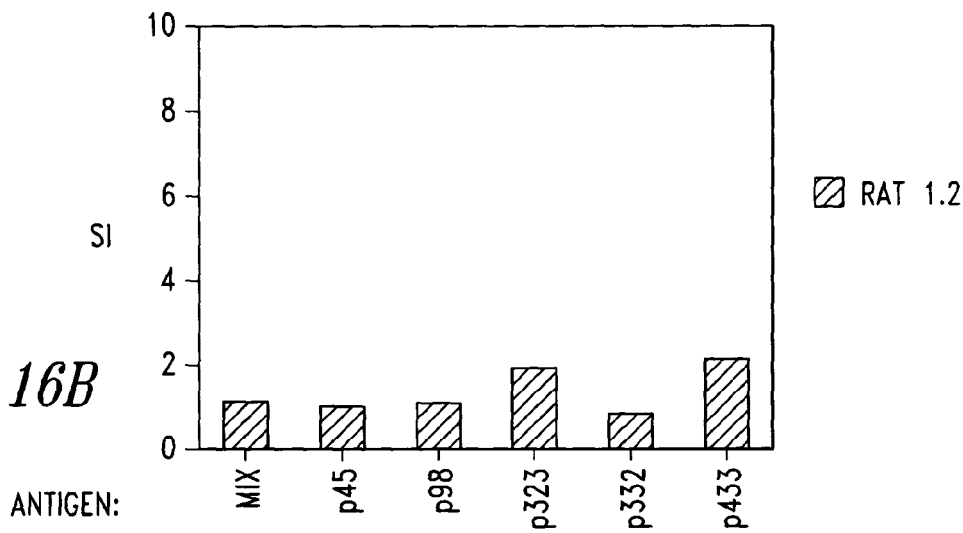
Figure 16C:
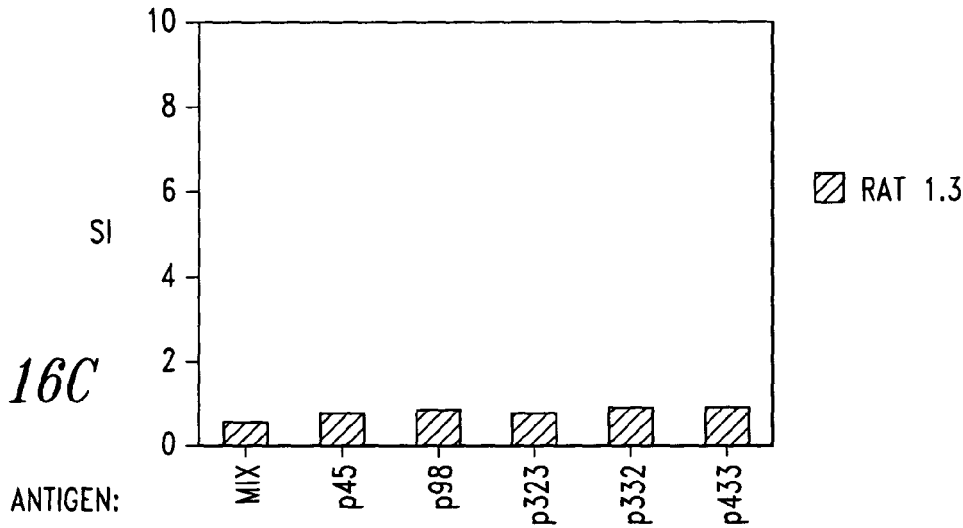

J. Immunization of Rats With ECD Peptides Elicits Only Weak Peptide-Specific T Cell Responses A similar analysis was performed with T cells derived from animals immunized with the ECD peptides. Unlike the responses observed from the animals immunized with the mixture of ICD peptides, animals immunized with ECD peptides exhibited only weak proliferative responses to the mixture of ECD peptides as well as to individual peptides (FIG. 16). Only one of three rats displayed SI of 2.0 or greater to peptides.

Figure 17:
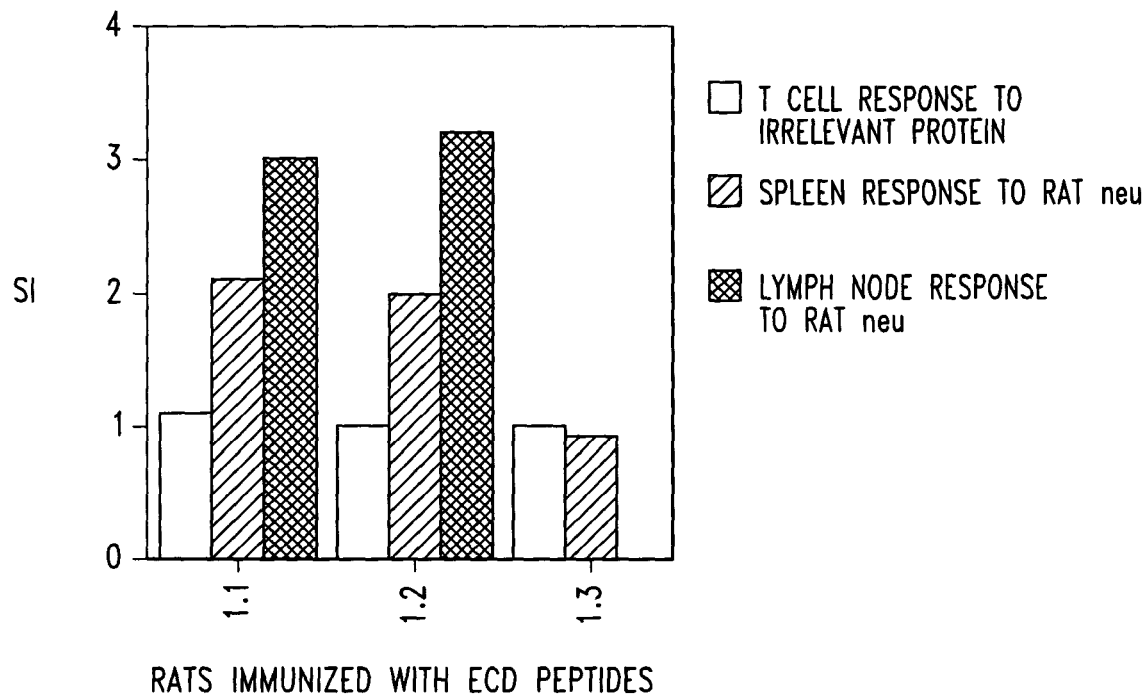
FIG. 17 graphically shows that immunization of rats with ECD peptides elicits weak, but positive, responses to neu protein. $1\times10^5$ cultured T cells derived from immunized spleen or lymph nodes were incubated with $1\times10^5$ syngeneic spleen as APC and 1 µg/ml of purified rat neu protein. Each experimental group was done in 6 well replicates. The data is expressed in terms of a stimulation index which is the mean of the experimental wells divided by the mean of the control (no antigen) wells. Stimulation indices greater than 2 are considered to be indicative of a primed response. Wild type ras protein was the irrelevant protein used in the assay.

K. Immunization of Rats with ECD Peptides Elicits Weak, but Positive Responses to Neu Protein Both splenic and lymph node T cells derived from ECD peptide immunized rats were analyzed for responses to rat neu protein (FIG. 17). Splenic T cells exhibited low level responses, whereas responses were greater for lymph node derived T cells. Proliferative responses were not the same for all animals tested. The maximum SI for spleen derived T cell lines was 2.1, whereas the maximum SI for lymph node derived T cells was 3.

From the foregoing, it will be evident that, although specific embodiments of the invention have been described herein for purposes of illustration, various modifications may be made without deviating from the spirit and scope of the invention.

The invention claimed is:

1. An isolated peptide consisting of the amino acid sequence of His-Leu-Tyr-Gln-Gly-Cys-Gln-Val-Val (Seq. ID No. 1).

2. An isolated peptide consisting of the amino acid sequence of Pro-Leu-Gln-Pro-Glu-Gln-Leu-Gln-Val (Seq. ID No. 2).

3. An isolated peptide consisting of the amino acid sequence of Cys-Leu-Thr-Ser-Thr-Val-Gln-Leu-Val (Seq. ID No. 7).

4. An isolated peptide consisting of the amino acid sequence of Val-Leu-Val-Lys-Ser-Pro-Asn-His-Val (Seq. ID No. 9).

5. An isolated peptide consisting of the amino acid sequence of Gln-Leu-Met-Pro-Tyr-Gly-Cys-Leu-Leu (Seq. ID No. 15).

* * * * *